(12) United States Patent
Franzen et al.

(10) Patent No.: US 7,255,835 B2
(45) Date of Patent: Aug. 14, 2007

(54) SINGLE PASS ATTENUATED TOTAL REFLECTION FOURIER TRANSFORM INFRARED MICROSCOPY APPARATUS AND METHOD FOR IDENTIFYING PROTEIN SECONDARY STRUCTURE, SURFACE CHARGE AND BINDING AFFINITY

(75) Inventors: Stefan Franzen, Apex, NC (US); Simon E. Lappi, Carrboro, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/234,343

(22) Filed: Sep. 4, 2002

(65) Prior Publication Data

US 2003/0157725 A1 Aug. 21, 2003

Related U.S. Application Data

(60) Provisional application No. 60/317,209, filed on Sep. 4, 2001.

(51) Int. Cl.
| | |
|---|---|
| G01N 21/03 | (2006.01) |
| G01N 21/13 | (2006.01) |
| G01N 33/552 | (2006.01) |
| G01N 21/35 | (2006.01) |
| G01N 21/01 | (2006.01) |
| G01N 33/543 | (2006.01) |
| G01N 33/48 | (2006.01) |

(52) U.S. Cl. .................. 422/82.11; 250/339.07; 250/339.08; 250/339.1; 250/339.11; 250/339.12; 422/68.1; 422/82.05; 422/82.09; 436/86; 436/87; 436/91; 436/92; 436/93; 436/94; 436/95; 436/96; 436/97; 436/98; 436/99; 436/171; 436/501; 436/518; 436/524; 436/527

(58) Field of Classification Search .......... 250/338.1, 250/339.07, 339.08, 339.1, 339.11, 339.12; 422/68.1, 81, 82.05, 82.09, 82.11; 436/501, 436/518, 524, 527, 52, 86–87, 91–99, 171
See application file for complete search history.

(56) References Cited

U.S. PATENT DOCUMENTS 3,896,312 A * 7/1975 Brown et al. ............... 250/343

(Continued)

FOREIGN PATENT DOCUMENTS

GB 2335922 * 10/1999

(Continued)

OTHER PUBLICATIONS

Ockman, N. Biopolymers 1978, 17, 1273-1284.*

(Continued)

*Primary Examiner*—Arlen Soderquist
(74) *Attorney, Agent, or Firm*—Jenkins, Wilson, Taylor, & Hunt, P.A.

(57) ABSTRACT

Apparatus and method for acquiring an infrared spectrum of a sample having or suspected to have an amide I band, an amide II band, an amide III band, an amide A band, an OH stretching region or a combination thereof. A representative method includes providing a sample; providing an internal reflecting element (IRE) with a functionalized tip; contacting the sample with the IRE to form a sample-IRE interface; directing a beam of infrared (IR) radiation through the IRE under conditions such that the IR radiation interacts with the sample-IRE interface once; recording a reflectance profile over a range of preselected frequencies, whereby an infrared spectrum of the of a sample having or suspected of having an amide I band, an amide II band, an amide III band, an amide A band, an OH stretching region or a combination thereof, disposed in an aqueous solution is acquired. Representative apparatus includes an internal reflecting element (IRE) comprising a reflection face located on the IRE at a region of intended contact between the IRE and a solublized sample; an infrared radiation source for supplying an evanescent wave of infrared radiation and directing the same from the outside of the IRE to the inside thereof so as to cause the infrared radiation to be incident on the reflection face, wherein the infrared radiation is reflected from the reflection face once; a sample cell; a functionalized tip comprising a surface-immobilized probe that partially or completely fills the volume exposed to the evanescent wave; and a detector for detecting the once-reflected infrared radiation.

15 Claims, 13 Drawing Sheets

U.S. PATENT DOCUMENTS

| | | | | |
|---|---|---|---|---|
| 3,902,807 | A * | 9/1975 | Fleming et al. | 356/300 |
| 4,365,303 | A * | 12/1982 | Hannah et al. | 702/28 |
| 4,602,869 | A * | 7/1986 | Harrick | 356/244 |
| 5,172,182 | A * | 12/1992 | Sting et al. | 356/244 |
| 5,210,418 | A * | 5/1993 | Harrick et al. | 250/339.07 |
| 5,347,364 | A * | 9/1994 | Kawasaki et al. | 356/445 |
| 5,362,445 | A * | 11/1994 | Miyahara et al. | 422/82.09 |
| 5,437,840 | A * | 8/1995 | King et al. | 422/82.08 |
| 5,470,757 | A * | 11/1995 | Gagnon et al. | 436/164 |
| 5,506,416 | A * | 4/1996 | Rizvi | 250/339.06 |
| 5,633,724 | A * | 5/1997 | King et al. | 356/445 |
| 5,710,713 | A * | 1/1998 | Wright et al. | 702/23 |
| 6,054,711 | A * | 4/2000 | Bruening et al. | 250/339.08 |
| 6,141,100 | A * | 10/2000 | Burka et al. | 356/451 |
| 6,274,872 | B1 * | 8/2001 | Katerkamp | 250/458.1 |

FOREIGN PATENT DOCUMENTS

| | | | |
|---|---|---|---|
| JP | 8-233728 | * | 9/1996 |
| WO | 99/05509 | * | 2/1999 |

OTHER PUBLICATIONS

Mookherji, T. Applied Spectroscopy 1982, 36, 323-325.*
Kellner, R. et al, Mikrochimica Acta 1984, 2, 61-74.*
Chittur, Krishnan K. et al, Journal of Colloid and Interface Science 1986, 111, 419-433.*
Oda, K. et al, Optics Communications 1986, 59, 361-365.*
Wragg, J. L. et al, Review of Scientific Instruments 1988, 59, 89-91.*
Heise, H. M. et al, Analytical Chemistry 1989, 61, 2009-2015.*
Bremer, P. J. et al, Biofouling 1991, 3, 89-100.*
Millot, J.-M. et al, Analytica Chimica Acta 1994, 295, 233-241.*
Kaneko, F. et al, Journal of Chemical Physics 1996, 105, 4812-4822.*
Oberg, K. A. et al, Analytical Biochemistry 1998, 256, 92-106.*
Charvat, A. et al, Spectrochimica Acta, Part A 1999, 55, 1553-1567.*
Boncheva, M. et al, Langmuir 1999, 15, 4317-4320.*
Boese, M. et al, Spectroscopy of Biological Molecules: New Directions, European Conference on the Spectroscopy of Biological Molecules, 8th, Enschede, Netherlands, 1999, 41-42, Editors: Greve, J. et al, Kluwer Academic Publishers, Dordrecht, Neth.*
Vigano, C. et al, Journal of Biological Chemistry 2000, 275, 10962-10967.*
Marrero, H. et al, Biophysical Journal 1987, 52, 629-635.*
Nocentini, M. et al, Mikrochimica Acta 1988, 1, 343-347.*
Story, G. M. et al, ACS Symposium Series 1990, 447, 225-236.*
Ford, C, G., Nature 1966, 212, 72.*
Parker, F. S. et al, Analytical Biochemistry 1967, 18, 414-422.*
Buerner, K., Fresenius' Zeitschrift fuer Analytische Chemie 1968, 243, 68-79.*
Toda, S. et al, Spectrochimica Acta 1970, 26A, 937-943.*
Goormaghtigh, E. et al, European Journal of Biochemistry 1991, 195, 421-429.*
Lu, D. R. et al, Journal of Colloid and Interface Science 1991, 144, 271-281.*
Jordanov, B. et al, SPIE 1992, 1575, 416-417.*
Ishida, K. P. et al, Applied Spectroscopy 1993, 47, 584-589.*
Ernst-Fonberg, M. L. et al, Biochimica et Biophysica Acta 1993, 1164, 273-282.*
Remmele, R. L., Jr. et al, Biopolymers 1994, 34, 365-370.*
Bauer, H. H. et al, Biochemistry 1994, 33, 12276-12282.*
Nabet, A. et al, Biochemistry 1994, 33, 14792-14799.*
de Jongh, H. H. J. et al, Biochemistry 1995, 34, 172-179.*
Chernyshova, I. V. et al, Applied Spectroscopy 1995, 49, 665-671.*
de Jongh, H. H. J. et al, Analytical Biochemistry 1996, 242, 95-103.*
Soga, I. et al, Langmuir 1998, 14, 4266-4271.*
Di Noto, V. et al, Vibrational Spectroscopy 1998, 18, 1-15.*
George, A. et al, Proceedings—Indian Academy of Sciences, Chemical Sciences 1999, 111, 121-131.*
Lewis, L. et al, Applied Spectroscopy 1999, 53, 375-380.*
Ishida, K. P. et al, Journal of Colloid and Interface Science 1999, 213, 513-524.*
Dobson, K. D. et al, Spectrochimica Acta Part A 1999, 55, 1395-1405.*
Nishikawa, Y., Applied Spectroscopy 1999, 53, 1054-1060.*
Muller, G. et al, Applied Spectroscopy 1999, 53, 1551-1555.*
Babaei, A. et al, Applied Spectroscopy 2000, 54, 496-501.*
Bryson, E. A. et al, European Journal of Biochemistry 2000, 267, 1390-1396.*
Brooksby, P. A. et al, Analytical Chemistry 2001, 73, 1155-1160.*
Pevsner, A. et al, Applied Spectroscopy 2001, 55, 788-793.*

* cited by examiner

Attenuated Total Reflection Cell for FTIR Microscopy

SEQUENCE LISTING

```
<160> NUMBER OF SEQ ID NOS: 4

<210> SEQ ID NO 1
<211> LENGTH: 6
<212> TYPE: DNA
<213> ORGANISM: Artificial
<220> FEATURE:
<223> OTHER INFORMATION: Self-complementary hexamer 1 used in NMR
      studies

<400> SEQUENCE: 1 cgtacg                                                              6

<210> SEQ ID NO 2
<211> LENGTH: 6
<212> TYPE: DNA
<213> ORGANISM: Artificial
<220> FEATURE:
<223> OTHER INFORMATION: Self-complementary hexamer 2 used for NMR
      studies

<400> SEQUENCE: 2
```

```
cgatcg                                                          6

<210> SEQ ID NO 3
<211> LENGTH: 12
<212> TYPE: DNA
<213> ORGANISM: Artificial
<220> FEATURE:
<223> OTHER INFORMATION: Self-complementary dodecamer used for NMR
      studies

<400> SEQUENCE: 3
cgcaaatttg cg                                                   12

<210> SEQ ID NO 4
<211> LENGTH: 8
<212> TYPE: DNA
<213> ORGANISM: Artificial
<220> FEATURE:
<223> OTHER INFORMATION: Self-complementary octamer used for NMR
      studies

<400> SEQUENCE: 4 ggtgcacc                                                        8
```

SINGLE PASS ATTENUATED TOTAL REFLECTION FOURIER TRANSFORM INFRARED MICROSCOPY APPARATUS AND METHOD FOR IDENTIFYING PROTEIN SECONDARY STRUCTURE, SURFACE CHARGE AND BINDING AFFINITY

CROSS REFERENCE TO RELATED APPLICATIONS

This application is based on and claims priority to U.S. Provisional Patent Application Ser. No. 60/317,209, filed Sep. 4, 2001, herein incorporated by reference in its entirety.

TECHNICAL FIELD

The present invention relates generally to FTIR-ATR spectroscopic methods and techniques, and specifically to optimizing performance for detection of structure and binding of DNA and protein samples. The methods include automated and high throughput FTIR-ATR procedures.

ABBREVIATIONS

| | |
|---|---|
| ATR | attenuated total reflectance |
| FTIR | Fourier transform infrared spectroscopy |
| FTIR-ATR | attenuated total reflection Fourier transform infrared |
| IgG | immunoglobulin G |
| IR | infrared |
| IRE | internal reflecting element |
| MCT | mercury cadmium tellurium |
| NiNTA | nickel-nitrilotriacetic acid |
| PCR | principal component regression |
| PDMS | polydimethylsiloxane |
| PLS | partial least squares |
| PTFE | polytetrafluoroethylene |
| SEC | standard error of calibration |
| S/N | signal-to-noise |
| UV | ultraviolet |

BACKGROUND ART

The sequencing of the human genome presents enormous opportunities for the determination of the mechanisms of many protein-based diseases. However, the interpretation and application of acquired genetic data will rely, at least in part, on an ability to determine protein secondary, tertiary and quaternary structure. Although the Human Genome Project can potentially unlock the amino acid sequence of many proteins, the activity of a protein is not determined only its amino acid sequence. Higher order structure plays an equally important, if not more important, role. Indeed, the prediction of secondary structure based on primary sequence is one of the most important problems in biology.

A goal of protein folding research efforts has been to solve various forms of protein structure by analyzing the primary amino acid sequence and thus to allow an interpretation of human genome sequence data in terms of protein structure. Teichmann et al., (2000) Bioinformatics 16:117-24; Zhang & Zhang, (2000) Biopolymers 53: 539-49. This effort, however, is far from complete and currently available technology is expected to rely heavily on the field of proteomics to determine the structure and function of the vast number of proteins now known only by their primary amino acid sequence. Preferably, techniques that provide rapid access to secondary structure information can be combined with known primary sequence information and homology modeling to gain structural information on a large number of proteins. Teichmann et al., (2000) Bioinformatics 16:117-24.; Zhang & Zhang, (2000) Biopolymers 53: 539-49.

Infrared (IR) spectroscopy is well established as a valuable technique for assessing protein secondary structure in solution. One particular form of IR spectroscopy, Fourier transform infrared spectroscopy (FTIR), has become an especially preferred form of IR spectroscopy for the study of protein secondary structure. FTIR has great utility in the rapid determination of secondary structure because it offers accurate, high-resolution spectra with excellent sensitivity and signal-to-noise (S/N) ratios, as compared to other forms of infrared spectroscopy. Kumosinski & Unruh, (1994) in ACS Symposium Series 576, Molecular Modeling: From Virtual Tools to Real Problems, (Kumosinski & Liebman, eds.) pp. 71-98; Susi & Byler, (1986) Method. Enzymol. 130: 290-311. Over the last thirty years, these properties of FTIR have been increasingly recognized and FTIR has developed into a reliable and accurate technique for the identification of structural features of a variety of sample, including protein secondary structure. Susi & Byler, (1986) Method. Enzymol. 130: 290-311; Byler & Susi (1986) Biopolymers 25: 469-87; Jencks, (1986) Method. Enzymol. 6 (125): 914-29; Douseeau & Pezolet, (1990) Biochem. 29: 8771-79; Purcell & Susi, (1984) J. Biochem. Bioph. Meth. 9: 193-99; Miyazawa, (1960) J. Chem. Phys. 32(6): 1647-52; Krimm, (1962) J. Mol. Biol. 4: 528-40; Krimm & Abe, (1972) Proc. Nat. Acad. Sci. 69 (10): 2788-92; Miyazawa et al., (1956) J. Chem. Phys. 24(2): 408-18.

Proteins are known to have nine characteristic absorption bands in the mid-infrared region (approximately 1250 $cm^{-1}$ to 1850 $cm^{-1}$) that yield conformational insight and are known as the amide A, B, and I-VII bands. Susi & Byler, (1986) Method. Enzymol. 130: 290-311; Susi (1972) Method. Enzymol. 26 Pt.C: 455-72. The secondary structure of proteins has primarily been characterized by the frequency of the amide I and II bands. Susi & Byler, (1986) Method. Enzymol. 130: 290-311; Jencks, (1986) Method. Enzymol. 6 (125): 914-29; Miyazawa (1960) J. Chem. Phys. 32(6): 1647-52; Krimm (1962) J. Mol. Biol. 4: 528-40; Krimm & Abe, (1972) Proc. Nat. Acad. Sci. 69(10): 2788-92; Miyazawa et al., (1956) J. Chem. Phys. 24(2): 408-18; Susi, (1972) Method. Enzymol. 26 Pt. C: 455-72. The characterization of protein samples almost exclusively by the amide I and amide II bands of the protein's IR spectrum, is due to limitations imposed by the presence of large solvent bands of both water ($H_2O$) and deuterium oxide ($D_2O$) that obscure regions of the infrared spectrum where additional informative bands can be observed. In effect, the solvent bands overlap the other bands present in a sample, which, therefore, cannot be clearly observed.

There is, however, a volume of information that can be used to derive structural information about a sample by analyzing the shape and position of bands in the amide I region of the spectrum. Studies have indicated that the quantity and quality of various amide I band frequencies are indicative of the presence of α-helices, β-sheets and random coil structures. Yang et al., (1985) Appl. Spectrosc. 39(2): 282-87; Byler & Susi, (1986) Biopolymers 25: 469-87; Susi & Byler, (1988) Appl. Spectrosc. 42(5): 819-25; Matsui & Tanaka, (1987) Appl. Spectrosc. 41(5): 861-65; Jakobsen et al., (1986) Biopolymers 25: 639-54; Wasacz et al., (1987) Biochem. 26: 1464-70. Often, however, conventional IR techniques cannot identify this information due to overlap of solvent signals with protein signals.

Attenuated total reflectance (ATR) is a technique useful for spectrally analyzing liquids having absorptions that are too strong for conventional transmission analysis. This condition is commonly encountered in the infrared (IR) region of the spectrum, which is the spectral region that encompasses the fundamental frequencies of most molecular vibrations. ATR has also found some application in the ultraviolet (UV) and visible regions for the analysis of dyes and other strongly absorbing water-soluble substances.

Water is an ideal solvent for biological samples. However, when used in transmission FTIR experiments it causes serious errors in the amide I region (1630-1690 $cm^{-1}$) due to the strong absorption of $H_2O$ at about 1640 $cm^{-1}$. Susi & Byler, (1986) *Method. Enzymol.* 130: 290-311; Byler & Susi, (1986) *Biopolymers* 25: 469-87; Jencks, (1986) *Method. Enzymol.* 6 (125): 914-29; Douseeau & Pezolet, (1990) *Biochem.* 29: 8771-79; Susi, (1972) *Method. Enzymol.* 26 Pt.C: 455-72. The absorption of water masks the absorption of a protein to such an extent that cell pathlengths of less than 6 microns must be used when analyzing a protein in an aqueous solution. Dousseau & Pezolet, (1990) *Biochem.* 29: 8771-79; Chittur, (1998) *Biomaterials* 19: 357-69. Furthermore, only the amide II region (1480-1575 $cm^{-1}$) can be reliably obtained in most protein spectra in which the protein is disposed in an aqueous solution. Polytetrafluoroethylene and other spacers are not generally available in thicknesses of less than 6 microns, thus limiting options for transmission FTIR experiments in aqueous solution. Because $H_2O$ signals can mask the amide I region, deuterium oxide ($D_2O$) is often used as a solvent. The strong D-O-D and H—O—H bending modes, however, still obscure the spectral regions from 1150-1250 $cm^{-1}$ and 1600-1800 $cm^{-1}$, respectively. Jencks, (1986) *Method. Enzymol.* 6 (125): 914-29.

In theory, both the amide I and amide II protein bands can be resolved, if spectra in both $H_2O$ and $D_2O$ solvents are obtained. The deuterium exchanged amide I and amide II bands are referred to as amide I' and amide II' bands in the spectroscopy literature. However, the exchange of proteins in $D_2O$ for the determination of spectra is tedious and can compromise the integrity of the sample. There are at least two notable problems associated with the use of $D_2O$: first, hydrogen atoms within the protein exchange with deuterium over wide range of time scales unless the protein is fully denatured (Susi, (1972) *Method. Enzymol.* 26 Pt.C: 455-72; Powell et al., (1986) *Appl. Spectrosc.* 40(3): 339-44; Nabet & Pezolet, (1997) *Appl. Spectrosc.* 51(4): 466-69; Dousseau et al., (1989) *Appl. Spectrosc.* 43(3): 538-42); and second, bands due the species H—O-D, D-O-D, and H—O—H are all present upon the introduction of $D_2O$ unless an absolutely complete exchange of hydrogen for deuterium, a process known as "deuteration", is achieved. Jencks, (1986) *Method. Enzymol.* 6 (125): 914-29. The exchange of N—H with N-D also shifts the amide II' band from 1550 to 1450 $cm^{-1}$ (Jencks, (1986) *Method. Enzymol.* 6 (125): 914-29; Dousseau et al., (1989) *Appl. Spectrosc.* 43(3): 538-42) and the presence of H—O-D in solution overlaps the amide II' and amide A' regions.

For reasons of convenience, the majority of FTIR structural investigations have focused on secondary structure information acquired from protein spectra of the amide I' band in $D_2O$ solution. The current state of the art for FTIR investigation of secondary structure requires placing proteins between two salt windows (typically these windows are fashioned of calcium fluoride or other salt) and orienting the windows so that they are separated by a thin pathlength space. An IR spectrum is subsequently acquired. Typical pathlength spaces are on the order of 6 to 25 microns. Barium fluoride, zinc selenide and other materials are also used for manufacturing windows.

These windows, however, can be costly and fragile and can have short lifespans. Additionally, such cells have the associated drawbacks that it is difficult to inject a sample into the ultrathin pathlength and to extract a sample from the ultrathin pathlength. Sample recovery can be a primary concern when the sample comprises a quantity of protein that is difficult to purify. A viable alternative to the traditional IR techniques is the use of the FTIR-ATR techniques. However, even certain FTIR-ATR techniques have drawbacks when the technique is used to study protein in aqueous solution. For the bending mode of water, there is typically an absorbance of 0.04 per reflection. Thus, for a typical waveguide with about 20 reflections, the absorbance of water is about 0.8 in the region of the amide I band. Solvent subtraction is possible but tedious in this case. In the region of the amide A band, the absorbance of the symmetric OH stretch is 0.16 per reflection. Thus, for a typical waveguide, the absorbance is about 3.2, prohibiting observation in this region. Multi-pass FTIR-ATR techniques that can be useful to acquire a spectrum from non-aqueous samples cannot, therefore, be effectively applied to protein samples which are best disposed in aqueous buffer to maintain sample integrity.

Thus, what is needed is a method that permits the observation of the spectral bands of a sample that appear in the IR region of the spectrum. A desirable method would be inexpensive, accurate and would eliminate the need for specialized equipment. Such a method would be easily automated for rapid data acquisition and analysis of many samples.

SUMMARY OF THE INVENTION

A solublized sample infrared spectrum measuring apparatus is disclosed. In a preferred embodiment, the apparatus comprises: (a) an internal reflecting element (IRE) comprising a reflection face located on the IRE at a region of intended contact between the IRE and a solublized sample; (b) an infrared radiation source for supplying an evanescent wave of infrared radiation and directing the same from the outside of the IRE to the inside thereof so as to cause the infrared radiation to be incident on the reflection face, wherein the infrared radiation is reflected from the reflection face once; (c) a sample cell; (d) a functionalized tip comprising a surface-immobilized probe that partially or completely fills the volume exposed to the evanescent wave; and (e) a detector for detecting the once-reflected infrared radiation.

A method of acquiring an infrared spectrum of a sample having or suspected to have an amide I band, an amide II band, an amide III band, an amide A band, an OH stretching region or a combination thereof, wherein the sample is disposed in an aqueous solution, is also provided. The method comprises: (a) providing a sample; (b) providing an internal reflection element (IRE) comprising a functionalized tip; (c) contacting the sample with the IRE to form a sample-IRE interface; (d) directing a beam of infrared (IR) radiation through the IRE under conditions such that the IR radiation interacts with the sample-IRE interface once; (e) recording a reflectance profile over a range of preselected frequencies, whereby an infrared spectrum of the sample having or suspected of having an amide I band, an amide II band, an amide III band, an amide A band, an OH stretching region or a combination thereof, wherein the sample is disposed in an aqueous solution is acquired.

A method of generating a library of IR spectra of protein samples in the frequency range of 50 to 3700 cm$^{-1}$ by employing single pass ATR and a functionalized tip is additionally disclosed. In a preferred embodiment, the method comprises: (a) providing a plurality of protein samples; (b) providing an internal reflecting element (IRE) comprising a functionalized tip; (c) contacting the sample with the IRE to form a sample-IRE interface; (d) directing a beam of IR radiation through the IRE under conditions such that the IR radiation interacts with the sample-IRE interface once; (e) recording the reflectance profile over the frequency range of 50 to 3700 cm$^{-1}$; (f) repeating steps (c) through (e) for each sample; and (g) compiling the absorbance profile of each sample in a computer database, whereby a library of IR spectra of protein samples in the frequency range of 50 to 3700 cm$^{-1}$ is generated.

A single-pass FTIR-ATR method of identifying secondary structure present in one or more solublized samples having or suspected to have secondary structure is also disclosed. The method comprises: (a) providing one or more solublized samples; (b) providing an internal reflecting element (IRE) comprising a functionalized tip; (c) contacting an IRE with one of the solublized samples to form a sample-IRE interface; (d) directing a beam of IR radiation through the IRE under conditions such that the IR radiation interacts with the aqueous solution-IRE interface once, thereby generating a reflectance profile using single-pass FTIR-ATR; (e) recording the reflectance profile over a preselected frequency range, the reflectance profile comprising observed frequencies; (f) repeating steps (c) through (e) for each of the solublized samples; and (g) correlating one or more observed frequencies with frequencies indicative of secondary structure composition, whereby secondary structure present in one or more solublized samples having or suspected to have secondary structure is identified using single-pass FTIR-ATR.

A single-pass FTIR-ATR method of identifying a degree of hydration of a first sample disposed in an aqueous solution is also disclosed. In a preferred embodiment, the method comprises: (a) providing first and second samples; (b) acquiring a single-pass ATR IR spectrum of a second sample when it is fully hydrated to generate a hydrated spectrum; (c) acquiring a single-pass ATR IR spectrum of the second sample when it is fully dehydrated to generate a dehydrated spectrum; (d) acquiring one or more single-pass ATR IR spectra of the second sample when it is partially hydrated to generate one or more partially hydrated spectra; (e) generating a mathematical algorithm correlating a degree of hydration of the second sample with spectral features of the hydrated, partially hydrated and dehydrated IR spectra; (f) acquiring a single-pass ATR IR spectrum of the first sample; and (g) applying the algorithm of step (e) to the spectrum of the first sample, whereby a degree of hydration of a first sample disposed in an aqueous solution is identified.

A method of generating a calibration model for determining secondary structure in a test sample is also disclosed. In a preferred embodiment, the method comprises: (a) providing a plurality of samples having a known type and amount of secondary structure, wherein the known type and amount of secondary structure is representative of the secondary structure to be determined in a test sample; (b) contacting an internal reflecting element (IRE) with one of the plurality of samples to form a sample-IRE interface; (d) directing a beam of IR radiation through the IRE under conditions such that the IR radiation interacts with the sample-IRE interface once, thereby generating a reflectance profile; (e) recording the reflectance profile at a preselected frequency; (f) repeating steps (b) through (e) for each of the plurality of samples; and (g) disposing the spectra in a computer database.

A method of detecting a binding event between a probe and a sample is disclosed. In a preferred embodiment, the method comprises: (a) providing a functionalized tip probe disposed on an internal reflecting element (IRE); (b) directing a beam of infrared radiation through the IRE under conditions such that the infrared radiation interacts with the probe once, thereby generating a probe reflectance profile; (c) recording the probe reflectance profile at a preselected frequency; (d) contacting an IRE with one of the plurality of samples to form a probe-sample-IRE interface; (e) directing a beam of infrared radiation through the IRE under conditions such that the infrared radiation interacts with the probe-sample-IRE interface once, thereby generating a probe-sample reflectance profile; (f) recording the probe-sample reflectance profile at a preselected frequency (g) comparing the spectrum of the probe reflectance profile with the probe-sample reflectance profile; and (h) detecting a binding event between a probe and a sample through the comparing of step (g).

In the above embodiments, it is preferable that the infrared radiation source is an FTIR microscope or a device that contains focusing optics to permit the utilization of FTIR radiation in a typical FTIR bench in the geometry shown in FIG. 13. It is also preferable that the IRE comprises a material selected from the group consisting of a germanium crystal and a zinc selenide crystal. When the IRE is an ATR objective, it is preferable that the ATR objective comprises a material selected from the group consisting of a germanium crystal and a zinc selenide crystal. The functionalized tip preferably comprises a material selected from the group consisting of a DNA oligomer and repeat sequences thereof, an RNA oligomer and repeat sequences thereof, a protein, a peptide, a small molecule, a DNA oligomer comprising one or more modified nucleic acids and repeat sequences thereof, an RNA oligomer comprising one or more modified nucleic acids and repeat sequences thereof, a protein comprising one or more modified amino acids and repeat sequences thereof and a peptide comprising one or more amino acids and repeat sequences thereof., which can be disposed on a scaffold structure. It is preferable that a sample cell comprises a milled polytetrafluoroethylene (PTFE) block, a microfluidic cell or a microfluidic channel. It is also preferable that samples be provided in volumes of about 50 picoliters. It is also preferable that the recording in the above be performed digitally. Optionally, the sample cell maintains the sample at a constant selectable temperature.

Accordingly, it is an object of the present invention to provide a single-pass ATR method to acquire the IR spectrum of a sample. It is another object of the present invention to provide a solublized protein infrared spectrum measuring apparatus. These and other objects are achieved in whole or in part by the present invention.

Some of the objects of the invention having been stated hereinabove, other objects will be evident as the description proceeds, when taken in connection with the accompanying drawings as best described hereinbelow.

DETAILED DESCRIPTION OF THE INVENTION

I. Definitions

Figure 1:
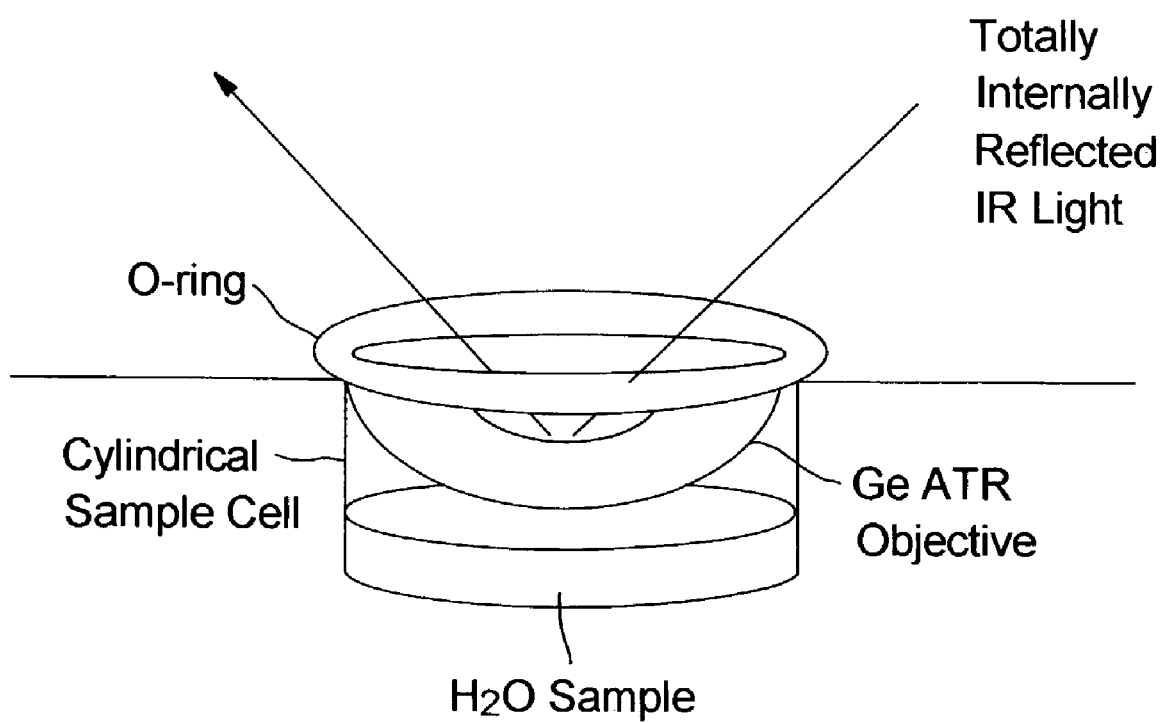
FIG. 1 is a schematic perspective view depicting the geometry of a single-pass attenuated total reflection cell and a functionalized tip.

Following long-standing patent law convention, the terms "a" and "an" mean "one or more" when used in this application, including the claims.

As used herein, the term "active volume" means a defined space from which spectral data can be acquired. In a preferred embodiment, an "active volume" is the space on which a beam of infrared light from an FTIR source is focused.

As used herein, the term "amino acid sequence" means an oligopeptide, peptide, polypeptide, or protein sequence, and fragments thereof, and naturally occurring or synthetic molecules. Where "amino acid sequence" is recited herein to refer to an amino acid sequence of a synthetic peptide or a naturally occurring protein molecule, amino acid sequence, and the like, the term is not meant to limit the amino acid sequence to the complete, native amino acid sequence associated with a protein molecule, but is intended to encompass variations on the native amino acid sequence as well.

As used herein, the term "aqueous" means comprising a water component. Thus an "aqueous solution" is a solution that comprises a water component. The terms "aqueous" and "aqueous solution" specifically encompass the inclusion of water, deuterium oxide or both as a water component.

As used herein, the term "detecting" means confirming the presence of a target entity by observing the occurrence of a detectable signal, such as an electrical, radiological or spectroscopic signal that will appear in the presence of the target entity. The term "detecting" also includes the use of infrared spectroscopy and microscopy techniques, such as Fourier transform infrared microscopy, attenuated total reflectance spectroscopy and attenuated total reflectance-Fourier transform infrared microscopy. "Detecting" an event or the presence of a compound can be done directly or indirectly. Thus, the term "detecting" broadly means identifying the presence or absence of an event, compound, molecule, etc.

As used herein, the term "FTIR-based instrument" means any instrument comprising an infrared radiation source. Representative, but non-limiting examples of FTIR-based instruments include FTIR microscopes and FTIR spectrometers.

As used herein, the term "functionalized tip" means a structure comprising a DNA oligomer, an RNA oligomer, a protein, a peptide, a small molecule, one or more modified amino acids, one or more modified nucleic acids and combinations thereof, which is associated with an IRE. The functionalized tip preferably contacts the sample during data acquisition. The exact composition of a functionalized tip can vary with nature of the experiment to be performed.

As used herein, the term "functionalized tip probe" means a chemical entity that exhibits a property to be identified in a sample. For example, if a study of a sample's charge is to be performed, a suitable functionalized tip probe can be a charged species. Or, if a DNA-protein interaction is to be investigated, a functionalized tip probe can comprise DNA or a protein. Protein-protein interactions, interactions involving DNA and/or RNA can also be performed, in which case, a suitable functionalized tip probe can comprise any suitable DNA or RNA oligomer. Peptide nucleic acids, as well as proteins and oligonucleotides comprising modified nucleic acids and amino acids, can be employed as components of a functionalized tip probe.

As used herein, the term "interact" means detectable interactions between molecules, such as can be detected using, for example, scanning transmission microscopy, fluorescence microscopy, Fourier transform infrared microscopy and/or attenuated reflectance Fourier transform infrared microscopy. The term "interact" is also meant to include "binding" interactions between molecules. Interactions can be, for example, nucleic acid-nucleic acid, protein-protein, protein-nucleic acid, protein-solvent or nucleic acid-solvent in nature.

As used herein, the terms "internal reflection element" and "IRE" are used interchangeably with the terms "objective" and "ATR objective" and mean a crystal, prism or other structure that will admit incoming radiation and reflect the radiation at least once from a surface on the interior of the element, preferably following interaction of the radiation with a sample in contact with the reflecting surface. Following such a reflectance, the radiation can be re-reflected or emitted from the element. Preferably an internal reflection element (IRE) comprises a germanium crystal, a zinc selenide crystal or other high index of refraction material capable of transmitting IR or visible light.

As used herein, the term "isolated" means oligonucleotides and/or peptide nucleic acids substantially free of other nucleic acids, proteins, lipids, carbohydrates or other materials with which they can be associated, such association being either with cellular material or in a synthesis medium. The term can also be applied to polypeptides, in which case the polypeptide will be substantially free of nucleic acids, carbohydrates, lipids and other undesired polypeptides.

As used herein, the term "isotopic" refers to a mass change, which does not produce any atomic instability that may lead to radioactive decay.

As used herein, the term "labeled" means the covalent, noncovalent or ionic attachment of a moiety capable of detection by electrochemical, spectroscopic, radiologic or other methods to a molecule.

As used herein, the term "modified" means an alteration from an entity's normally occurring state. An entity can be modified by removing discrete chemical units or by adding discrete chemical units. The term "modified" encompasses detectable labels as well as those entities added as aids in purification. Any variation from the normally occurring state, regardless of degree, is encompassed by the term "modified".

As used herein, the term "multi-pass ATR" means an attenuated total reflectance technique in which radiation incident on an internal reflectance element having two or more reflection faces disposed within the IRE experiences two or more interactions with a reflection face before exiting the IRE. Such interactions are typically referred to as "bounces" or "passes". Application of multi-pass ATR generates a multi-pass ATR spectrum. Typically, the IRE is in contact with a sample, the incident radiation is IR radiation and the exiting radiation subsequently interacts with a detector.

As used herein, the terms "polypeptide", "protein", "gene product" and "peptide" are used interchangeably and mean any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to an expressed gene product or a synthesized chemical entity.

As used herein, the term "reflectance profile" means a representation of the frequency and intensity of radiation detected by a detector following at least one reflectance of the radiation from a surface.

As used herein, the term "reflecting surface" means a surface capable of reflecting incident radiation. Reflection from a reflecting surface need not be total and it is contemplated that some incident radiation can interact with a material disposed in a space outside the material embodying a reflecting surface. Indeed, the technique of attenuated total internal reflection (ATR) is based on the principle that an evanescent wave interacts with a sample that is within one fifth of one wavelength of the dielectric boundary. Preferably the reflecting surface is disposed in an IRE. In this case, it is also preferred that the IRE comprises a germanium crystal, a zinc selenide crystal or other high index of refraction material capable of transmitting IR or visible light.

As used herein, the term "secondary structure" means the alpha-helical, beta-sheet, random coil, beta turn structures and helical nucleic acid structures that occur in proteins, peptide nucleic acids, compounds comprising modified nucleic acids, compounds comprising modified amino acids and other types of compounds as a result of, at least, the compound's composition.

As used herein, the term "single-pass ATR" means an attenuated total reflectance technique in which radiation incident on an internal reflectance element (IRE) having one or more reflection faces disposed within the IRE experiences only one interaction with a reflection face before exiting the IRE. Such interactions are typically referred to as "bounces" or "passes". Application of single-pass ATR generates a single-pass ATR spectrum. Preferably, the IRE is in contact with a sample, the incident radiation is IR radiation and the exiting radiation subsequently interacts with a detector.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

II. General Considerations

The single-pass FTIR-ATR method of the present invention has been shown to have adequate signal-to-noise ratio and much higher sample-to-sample reproducibility than other techniques. A major advantage of single-pass FTIR- ATR is that the $H_2O$ or $D_2O$ spectrum can be easily subtracted across the spectral range. The quality of the spectra obtainable, combined with the ease of sample loading, provides a completely new range of possible experimental configurations. The single-pass FTIR-ATR method of the present invention allows the replacement of demountable thin pathlength cells with a simple injection onto a stage below the crystal permitting easy sample recovery. Thus, the single-pass FTIR-ATR method of the present invention is suited to automation, microfluidic applications including rapid mixing, and reliable temperature control over very small sample volumes.

The simplicity of this technique also allows the use of an autosampler such as those routinely used for HPLC or GC. These innovations enable the single-pass attenuated total reflection FTIR method of the present invention to be automated for analysis of batch processes in real time with minimal operator contact. The use of microfluidic delivery as described herein can be used alone or as a component of a complete automation of the single-pass attenuated total reflection-FTIR method. The low solvent backgrounds achievable with the present invention offer the further advantages in that comparisons need not be made for partially deuterated proteins and, for the first time, the amide I, II, and A bands of protein samples can be observed simultaneously. In fact, the observation of the amide A band is almost impossible with other spectroscopic techniques. The present invention can facilitate the development of an information technology to accompany the new range of spectral data and has utility for both pharmaceutical and bioinformatics/proteomics industries.

FTIR spectra of proteins in aqueous solution can be obtained using an FTIR microscope or as a standard FTIR bench accessory, both in a single-pass ATR configuration, as disclosed herein. In one embodiment of the present invention, a germanium crystal, zinc selenide crystal or other material is at the focus of a Cassagranian objective in an FTIR microscope, such as a UMA500 microscope (available from BioRad Inc. of Cambridge, Mass.). The use of a single-pass ATR geometry in a FTIR microscope presents a significant advance over currently available techniques in art for FTIR-ATR analysis of proteins in solution. In one experimental configuration disclosed herein, protein solutions comprising aqueous buffers are injected onto a cylindrical sample well that is milled in a PTFE block. The described experimental configuration is shown in FIG. 1. Background spectra of the buffer or solution in which a sample of interested is disposed can be acquired either before or after a spectrum of a sample is acquired.

This approach can be contrasted with current multi-pass FTIR-ATR methods. In multi-pass FTIR-ATR, the cell geometry can change upon disassembly, and thus lead to changes in the pathlength for each sample. Therefore, sample-to-sample variability in multi-pass FTIR-ATR is much more of a concern than in the single-pass configurations described herein. Powell et al., (1986) *Appl. Spectrosc.* 40(3): 339-44. It has been stated that an external method for sample loading and unloading needs to be developed to avoid changes in pathlength and deviations in the angle of incidence. Powell et al., (1986) *Appl. Spectrosc.* 40(3): 339-44. The apparatus and methods of the present invention offer a solution to this and other problems.

Another disadvantage of multi-pass FTIR-ATR is that this technique imposes requirements on sample volumes and preparation, specifically that for effective multi-pass FTIR-ATR measurements, a uniform sample must be distributed over a large area (about 4 square centimeters). Thus, multi-pass FTIR-ATR also has requirements on sample properties (i.e. that the sample be uniform) and sample volumes (i.e. that the sample be uniform over a large area).

The configuration disclosed in the present invention solves this and other problems. For example, a spectrum obtained by single-pass FTIR-ATR is highly reproducible, which offers an advantage over multi-pass FTIR-ATR. Additionally, the absorption of pure water is less than 0.3 absorbance units and therefore, reliable subtraction of spectral features due to the presence of water can be achieved. This advantage, in turn, justifies the use of one or more algorithms to effectively subtract background water signals from protein spectra; some appropriate algorithms are provided in the literature and incorporated herein by reference. Chittur, (1998) *Biomaterials* 19: 357-69; Powell et al., (1986) *Appl. Spectrosc.* 40(3): 339-44; Jongh et al., (1996) *Anal. Biochem.* 242: 95-103.

Attenuated total reflection (ATR) spectroscopy employing a germanium crystal, a zinc selenide crystal or other suitable material as an internal reflection element in a Fourier-transform infrared spectrometer has been used in the art to identify an amide I line shape in aqueous solution. This type of multi-pass FTIR-ATR has been used to study the conformation and orientation of adsorbed proteins, also known as protein films. Chittur, (1998) *Biomaterials* 19: 357-69; Powell et al., (1986) *Appl. Spectrosc.* 40(3): 339-44; Jongh et al., (1996) *Anal. Biochem.* 242: 95-103. Since the penetration depth of infrared light having a 6-micron wavelength is approximately 600 nm, the effective path length is very short, which has enabled analysis of samples disposed in aqueous solution. Most FTIR-ATR studies, however, are performed on proteins gels or films. Chittur, (1998) *Biomaterials* 19: 357-69; Jongh et al., (1996) *Anal. Biochem.* 242: 95-103. Even under conditions in which a protein sample is adsorbed on a surface, it has proven difficult to obtain a spectrum of the amide A band. Moreover, it has also been difficult to monitor the fully hydrated protein due to interference from an aqueous solvent. These and other disadvantages of multi-pass FTIR-ATR are overcome by the single-pass FTIR-ATR techniques disclosed in the present invention.

III. Equipment Useful for Obtaining Infrared Spectra

Figure 13:
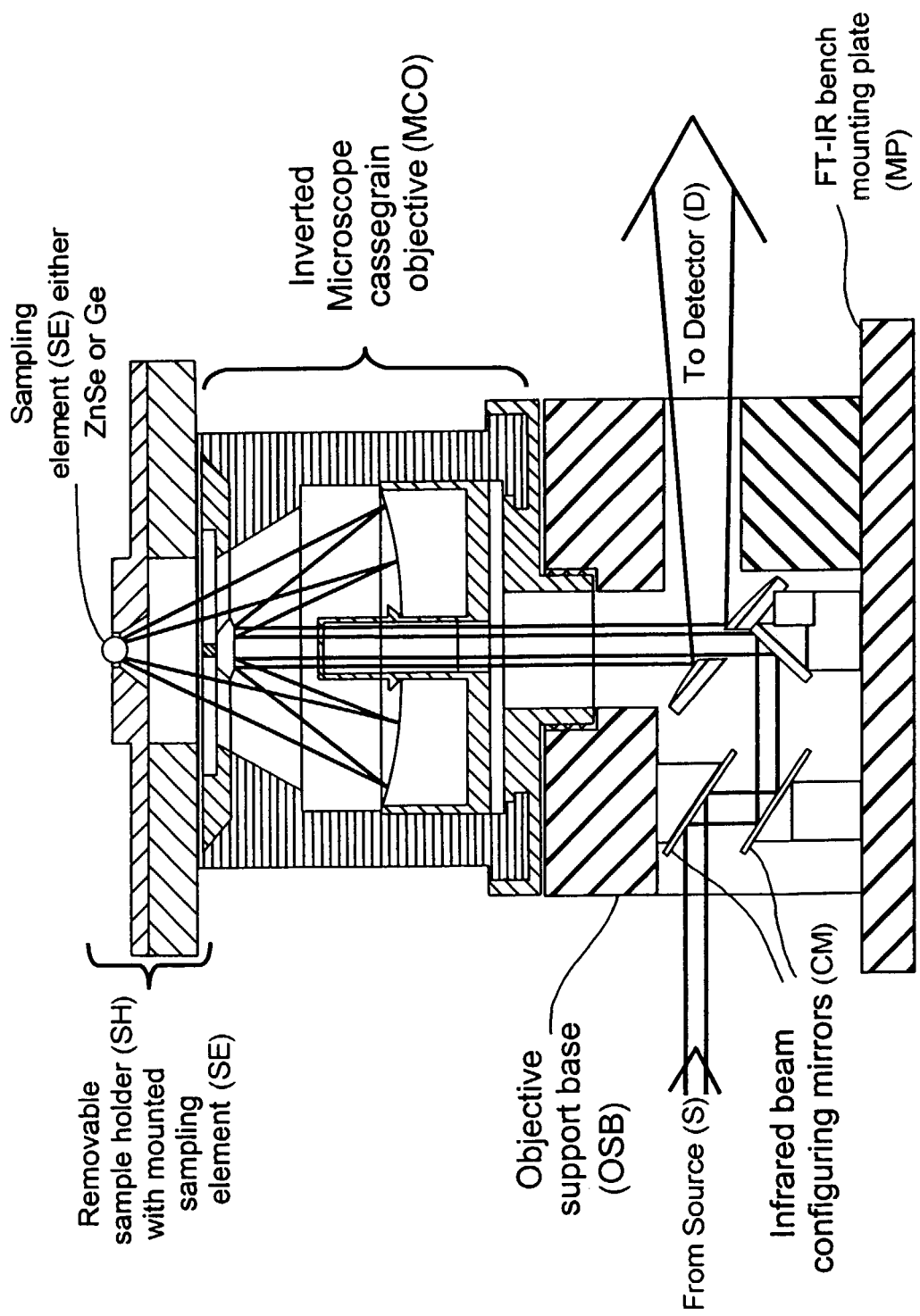
FIG. 13 is a schematic view of a possible bench accessory configuration, which uses the same optical elements as that of the infrared microscope.

The present invention can be used to obtain infrared spectra over a wide spectral range, however the range of 50-3700 $cm^{-1}$ is often of particular interest because spectra can be acquired over this range using commercially available equipment in conjunction with the disclosure of the present invention. There is no need for specialized equipment to be designed or manufactured, although it might be desirable to manufacture a unique sample cell depending on the sample and experiment. For example, vitrophilic proteins are preferably studied using a sample cell comprising polytetrafluoroethylene (PTFE) sold under the registered trademark TEFLON® by E. I. DuPont De Nemours & Co. of Wilmington, Del. or other material, as described herein below. Equipment useful for acquiring infrared spectra in the range of 50-3700 $cm^{-1}$ includes, but is not limited to, an ATR IRE; an FTIR microscope or a conventional bench accessory as shown in FIG. 13; a sample cell; and appropriate data processing equipment. This equipment is described in further detail below.

III.A. Suitable Internal Reflecting Elements

Attenuated total reflection (ATR) spectroscopy is predicated on the concept that, when light traveling within a medium impinges upon an interface between that medium and a medium of lower refractive index, it either passes into the second medium or is totally internally reflected, depending on whether the quantity $[n_1/n_2 \sin \theta_i]$ is less than or greater than one. In this relationship, $n_1$ and $n_2$ are the refractive indices of the first and second media, respectively, and $\theta_i$ is the angle of incidence. If $n_1/n_2 \sin \theta_i$ is greater than one, total internal reflection occurs. Although the internal reflection is referred to as total, the light, during the reflection process, penetrates a short distance into the second medium. The depth of penetration depends in a predictable fashion on the refractive indices of the two media and the angle of incidence, and is typically on the order of tenths of the wavelength of the light. If the incident light includes a wavelength absorbed by a constituent of the second medium, light of such wavelength will be partially absorbed or attenuated during reflection due to the penetration of the light into the second medium. This effect is referred to as attenuated total reflection. Due to the very shallow penetration of the light into the second medium, ATR is a useful technique for measuring absorbance by strongly absorbing materials. ATR has also been particularly useful for measuring absorbance of material deposited on a surface. Attenuated total reflection spectroscopy is widely used to collect an absorption spectrum from samples that are too opaque for direct absorption measurements.

In practice, one surface of an internal reflecting element (IRE) is placed in contact with a test sample. An incident beam of radiation is directed through the IRE so that it is totally internally reflected at the boundary between the IRE and the test sample. Some of the energy of the incident radiation is absorbed by the test sample through evanescent coupling. The amount of absorption is representative of the molecular structure and/or the molecular species found in the test sample. The reflected radiation, therefore, includes information from which an absorption spectrum for the test sample can be acquired.

IREs utilizing total internal reflection or attenuated total reflection principles are commonly found in optical systems designed to analyze samples by assessing the optical constants of the sample and by establishing the physical and chemical composition thereof. Examples of IREs disposed in various optical systems are shown, for example, in U.S. Pat. Nos. 4,602,869 and 3,393,603. In the present invention, a germanium crystal and a zinc selenide crystal are two preferred embodiments of an IRE.

Over the years, a variety of ATR-based devices have been developed. ATR probes (i.e. IREs) generally fall into categories based, at least in part, on their geometries. Common ATR probe geometries include those employing cylindrical ATR rods, such as those described in U.S. Pat. No. 5,051,551, and those employing conical and hemispherical elements. The geometry of the element can influence the type and amount of information obtainable in a given experiment. In the context of the present invention, IRE geometry is preferably, but not necessarily, hemispherical.

In the context of the present invention, consideration must be given to the angle of incidence, i.e. the angle at which incident light impinges on an IRE. The angle of incidence is defined as the angle between the ray direction and the normal to the surface. A 45-degree angle of incidence is often convenient for a multi-pass FTIR-ATR element. That angle is usually appropriate for the analysis of organics in the IR region. For the high index. ATR materials available for use in the IR region, it is sufficiently above the critical angle to avoid significant data distortion. Higher angles can be used, however, and can be useful in grazing angle experiments, such as those described in the present disclosure. Thus, the angle of incidence and the composition of an element can be varied to optimize the parameters for a given experiment. Such variables will depend on the nature of the experiment. In the present invention, a germanium or zinc selenide ATR element can be used and for this composition, a suitable angle of incidence can be 14.5 degrees from surface normal.

III.B. Suitable FTIR Instruments

Researchers have been turning increasingly to infrared microscopy as a problem-solving adjunct to Fourier-transform infrared (FTIR) spectroscopy. The combined technique uses a microscope attachment to an FTIR spectrophotometer to acquire transmission or reflectance spectra of regions or particles less than 10 microns in diameter. One reason for the recent adoption of this technique by researchers is that detailed chemical information can be acquired from very small sample volumes and/or highly localized regions. Another reason for increased interest in the technique by researchers is the recent availability of low-cost benchtop FTIR spectrophotometers having high quality optics.

An FTIR microscope can have multiple uses. For example, FTIR microscopes permit microscopic observation in the visual range (i.e. operation in visual mode), yet also facilitate infrared analysis of the sample, using the modulated output beam of an interferometer spectrometer. The visual mode can also be used to move a sample into place for use of the IR analytical beam. Additionally, the microscope permits IR analysis of a sample in either the transmission mode or the reflectance mode. In transmission mode, the IR beam is monitored before and after it interacts with a sample, and those observations are compared. In transmission mode, the geometry of the system is such that a detector is place on the opposite side of the sample from the incident IR beam and provides a measure of IR light transmitted through the sample.

The reflectance mode employs the same concept, but a different geometry. In reflectance mode, a detector is typically positioned on the same side of the sample as the incident light, however the geometry is such that the detector is oriented at an angle from the normal equal to the incident angle from normal of the IR beam. In a multi-pass experiment, these angles are typically 45 degrees.

A suitable FTIR microscope for practicing the present invention will permit the movement and orientation of a sample by visual inspection. A suitable instrument will also, obviously, permit IR transmission or reflectance analysis of the sample. In the context of the present invention, analysis in reflectance mode is desirable because, as described hereinbelow, the present invention employs an ATR crystal oriented at the focal point of the IR analysis beam to assist in obtaining an IR spectrum of a protein, peptide or other sample. It is also preferable that the FTIR microscope be adapted to permit onboard analysis of acquired spectra or, in lieu of such onboard equipment, equipment that will permit transport of acquired data to a workstation where it can be treated and analyzed. Suitable FTIR microscopes are available commercially, such as the UMA500 microscope, which is available from BioRad, Inc. of Cambridge, Mass.

III.C. Suitable Sample Cells and Delivery Devices

Considerations for sample placement and orientation in an instrument developed concurrently with the evolution of the field of spectroscopy. Although procedures and equipment for placing and orienting samples in a spectrophotometer in order to acquire the sample's spectrum are established for infrared spectrometers, parallel developments have also taken place in UV spectrometers, visible light spectrometers, near infrared spectrometers, far infrared spectrometers, Raman spectrometers and fluorescence spectrometers to achieve the same goals.

In order to acquire spectra of liquids, solids and pastes, several methods have been developed. Devices known as demountable cells and sealed cells have been traditionally employed. In a typical demountable cell, two suitable windows of IR transmitting material, such as sodium chloride, are held in place by a retaining ring which is itself held in position by a number of bolts disposed on a mounting plate that fits into the cell slide of an FTIR spectrometer. The cell slide insures that the sample held between the windows will be in the energy beam (i.e. the IR radiation beam) of the spectrometer. The cell is loaded by placing sample-containing liquid between the windows, placing the windows on the plate, attaching the retainer ring to upright bolts, placing a nut on each bolt and tightening down to the desired level. A demountable cell can be employed to acquire spectra of liquids or pastes but not solids. The pathlength in a demountable cell can be varied by increasing the length of a spacer element disposed between the two windows.

Sealed cells, on the other hand, are not capable of disassembly. Sealed cells typically comprise windows and a spacer element, which can comprise lead. Sealed cells have a fixed pathlength, usually between 0.015 mm and 1 mm, although pathlengths of 5 mm and up to 10 mm can be purchased, depending on the material and geometry of the cell. Sealed cells are traditionally used to obtain spectra of liquids.

Both sealed cells and demountable cells have their drawbacks. For acquiring spectra of liquid samples, which is an aspect of the present invention, sample volume can be of primary concern. Both sealed and demountable cells can require a significant volume of a solution in order to eliminate dead volumes and acquire reliable and accurate spectra. Often, biological samples such, as proteins and peptides, can only be isolated in small quantities. Sealed cells and demountable cells have the disadvantage that comparatively larger volumes are required to generate useful spectra.

Sample recovery is often a concern when spectra of biological samples are desired. Biological samples are often difficult to purify in large quantities and thus, it is highly desirable to preserve as much of the sample as possible following data acquisition. One method of preserving sample volume is by decreasing the amount of sample present in a sample cell. Unlike other sample cells requiring a large volume of sample, the present invention takes this approach and requires a very low sample volume (and a very small amount of material) in order to acquire a spectrum. Following data acquisition, the sample can be easily removed from a sample cell and placed in a container for storage. Thus, the apparatus and methods of the present invention offer the advantage that, in practice, there will be very little loss of sample.

In one embodiment, the present invention solves the above described, and other, problems by employing a milled block as a sample cell. PTFE, such as that sold under the registered trademark TEFLON® by E. I. DuPont De Nemours & Co. of Wilmington, Del., is preferable for the manufacture of a sample cell. PTFE can be used because the present invention uses ATR and there is no requirement for the transmission though a sample cell. The properties of PTFE (again preferably that sold under the registered trademark TEFLON® by E. I. DuPont De Nemours & Co. of Wilmington, Del.) are well known and are amenable to biological samples.

The present invention also addresses the problem of sample size by enabling configurations that require significantly smaller sample volumes than do prior art cells and holders. The effective sample volume required for a configuration of the present invention is very small, since the focal spot size of the interferometer's infrared light beam in a suitable crystal (e.g. a zinc selenide or germanium crystal) is about 30 microns. The invention, including functionalized tip and microfluidic delivery, can be immediately applied to a currently available FTIR microscope objective. However, an apparatus can also adapt the radiation in a typical FTIR bench to a device that contained the essential optical elements without the expense of using the FTIR microscope optics. This is a separate attachment that can be placed in the sample compartment of a typical FTIR bench, such as shown in FIG. 13. The ability of the present invention to accommodate small sample volumes can be highly desirable and beneficial where only small quantities of a sample are available.

Additionally, the apparatus and method of the present invention, an embodiment of which is presented in FIG. 1, enables a sample to be fully recovered. This ability is imparted in part by the design of the sample cell, which does not require that the sample be placed between windows. instead, the present invention permits injection of the sample into, for example, a small, depressed structure disposed beneath an ATR crystal. There is no need for sealing or additional modifications to the sample cell or geometry. The configuration of the present invention is in contrast with solution cells, which are sealed. The present invention can also obviate the need for vacuum grease or other sealant material, which is typically placed on the spacer to seal the cell. The use of a sealant such as vacuum grease can make it difficult to recover the sample and can increase the chance of inadvertently introducing a contaminant into the sample volume.

Preferably, the sample cell of the present invention is disposed so as to be compatible with a robotic injection system, whereby sample injection, sample removal and cleansing of the sample cell between measurements can be automated. Alternatively, the sample cell can comprise a microfluidic cell, which can be used for easy sample introduction and removal.

Yet another sample delivery option facilitated by the present invention is the use of a microfluidic channel. A microfluidic channel is a channel disposed on a substrate through which a liquid sample is free to pass. The precise dimensions of a microfluidic channel can vary with the requirements of an experiment. It is preferable that a microfluidic channel be situated and dimensioned so as to allow one or more functionalized tip probes to interact with sample as it progresses down the length of the microfluidic channel. A microfluidic channel can comprise an element of a system by which sample is continuously applied to a functionalized tip probe. Alternatively, sample can be applied at a point where sample flow is directed towards a functionalized tip probe and sample that has not associated with the functionalized tip probe can be recovered at a point where sample flow is directed away from a functionalized tip probe.

Figure 4:
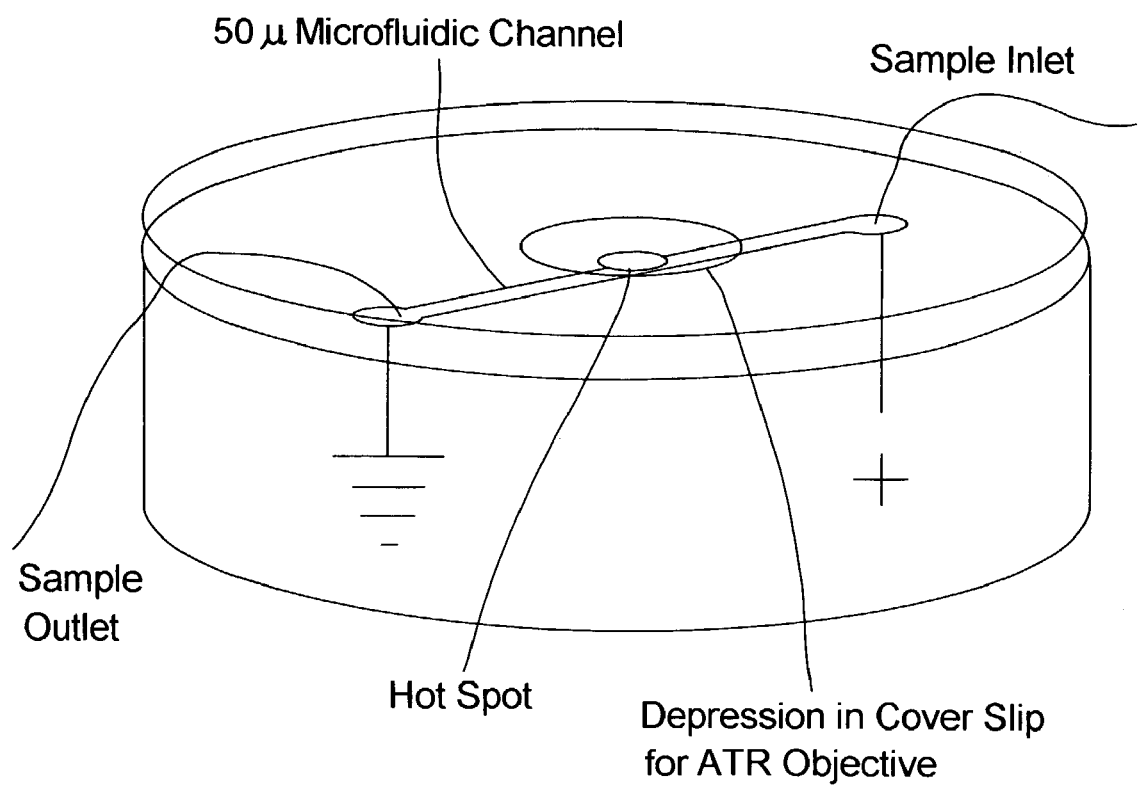
FIG. 4 is a schematic perspective view depicting a microfluidic sample cell suitable for use in accordance with the present invention.

When a microfluidic channel is employed delivery and recovery of the sample can be followed by a rinsing step. In a preferred embodiment, a microfluidic sample cell or device can be constructed by etching a channel 50 microns wide and 10 microns deep on a silicon wafer, as shown in FIG. 4. In this embodiment, the 50 micron wide by 10 micron deep channel can be made in a sample cell substrate (i.e. a silicon wafer) by lithography. Two small reservoirs can be adapted to provide the sample inlet and outlet via connections of polypropylene tubing bonded to a cover. A depression in the cover can be made that matches the curvature of the IRE, which is a germanium crystal in the depicted configuration. The active volume of the ATR objective (i.e. the focal point) is centered on the channel, so that the absorption signal is due entirely to the sample solution that is flowing through the channel, The active volume is denoted by the term "hot spot" in FIG. 4.

The driving force for the protein flow through the channel can be an electrically-driven electroosmosic process. In FIG. 4, an electrically-driven electroosmotic configuration is depicted as a positive electrode and ground attached to the inlet and outlet, respectively. The microfluidic channel shown in FIG. 4 is driven by electroosmotic flow, although other driving methods, such as pressure, are possible. A suitable cover slip can be fashioned of silicon, PTFE (preferably that sold under the registered trademark TEFLON® by E. I. DuPont De Nemours and Company, Wilmington, Del.), or other suitable substrate. The cover slip can have a depression that accommodates the IRE and allows it to contact the flowing solution, while leaving no gap for the solution to escape.

The microfluidic device shown has the advantage that extremely small volumes of sample can be delivered to the focal point of an IRE, thereby taking full advantage of the technique. By way of example, if the focal point of an IRE is taken to be 50 microns in diameter and the penetration depth of the evanescent wave to be 2 microns, the volume delivered in a channel of dimensions 50 microns by 10 microns is approximately 25 picoliters. Thus, the use of small volumes is concurrent with the automation of the techniques of the present invention.

A syringe can also-be employed to deliver sample to a functionalized tip. A syringe can be employed to apply sample directly to the tip itself, or a syringe can be employed to direct a stream of liquid sample into a microfluidic channel.

III.D. Suitable Data Processing Equipment

Mathematical and statistical operations that are performed in the course of practicing the present inventive methods can be performed using any suitable computational equipment. For example, a commercially available personal computer can be used as a platform for software that can facilitate the acquisition of data, the calculation of difference spectra and perform spectral and other analysis. Computers networked with an FTIR instrument can be employed to acquire data on one machine and process it on another. Suitable data acquisition and management software packages can be designed and written de novo or can be purchased. Suitable commercially available software packages can include SCANTRAQ BASIC™ software package available from FTG Software Associates of Princeton, N.J. and GRAMS/32™ Version 5.2 software package, available from ThermoGalactic of Salem, N.H.

III.E. Functionalized Tip

A suitable IRE can comprise a functionalized tip, which can circumvent many problems commonly associated with acquiring data. Generally, a functionalized tip of the present invention can comprise a chemical entity having a desired property, which acts as a functionalized tip probe. This functionalized tip probe can be associated with the IRE. It is preferable that the functionalized tip probe be associated with the IRE at a location at which the functionalized tip probe can interact with a sample. In practice, the functionalized tip makes it possible to study a variety of sample properties, which will be dependent on the nature of the functionalized tip probe selected.

An advantage of the functionalized tip is its ability to circumvent the need to accommodate small sample volumes. Delivery of small volumes (e.g. <100 picoliters) is nearly impossible using current technology. Generally, the use of a microfluidic channel or similar structure in conjunction with a functionalized tip circumvents the problems associated with handling small volumes, while at the same time making use of the small active volume for the focus of the FTIR-ATR objective.

III.E.1. Properties that can be Studied Using a Functionalized Tip

As discussed further hereinbelow, some of the properties that can be studied by employing a functionalized tip probe can include identification of the overall charge of a sample and the affinity of a sample for the functionalized tip probe. When the functionalized tip probe is a DNA oligomer, affinity studies can include identifying the affinity of a DNA binding protein for the probe, the affinity of a DNA or RNA oligo for the probe, or the affinity of a protein or oligo comprising a modified amino acid or nucleic acid for the probe. Depending on the design of the functionalized tip probe, the functionalized tip can detect interactions between the functionalized tip probe and virtually any sample, based on affinity.

III.E.2. Operation of a Functionalized Tip

Figure 5A:
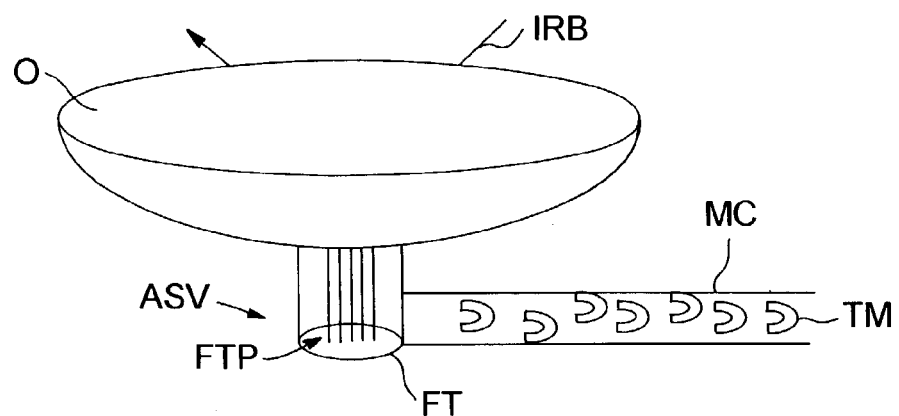
FIG. 5A is a schematic diagram depicting a preferred embodiment of a functionalized tip in accordance with the present invention.
Figure 7:
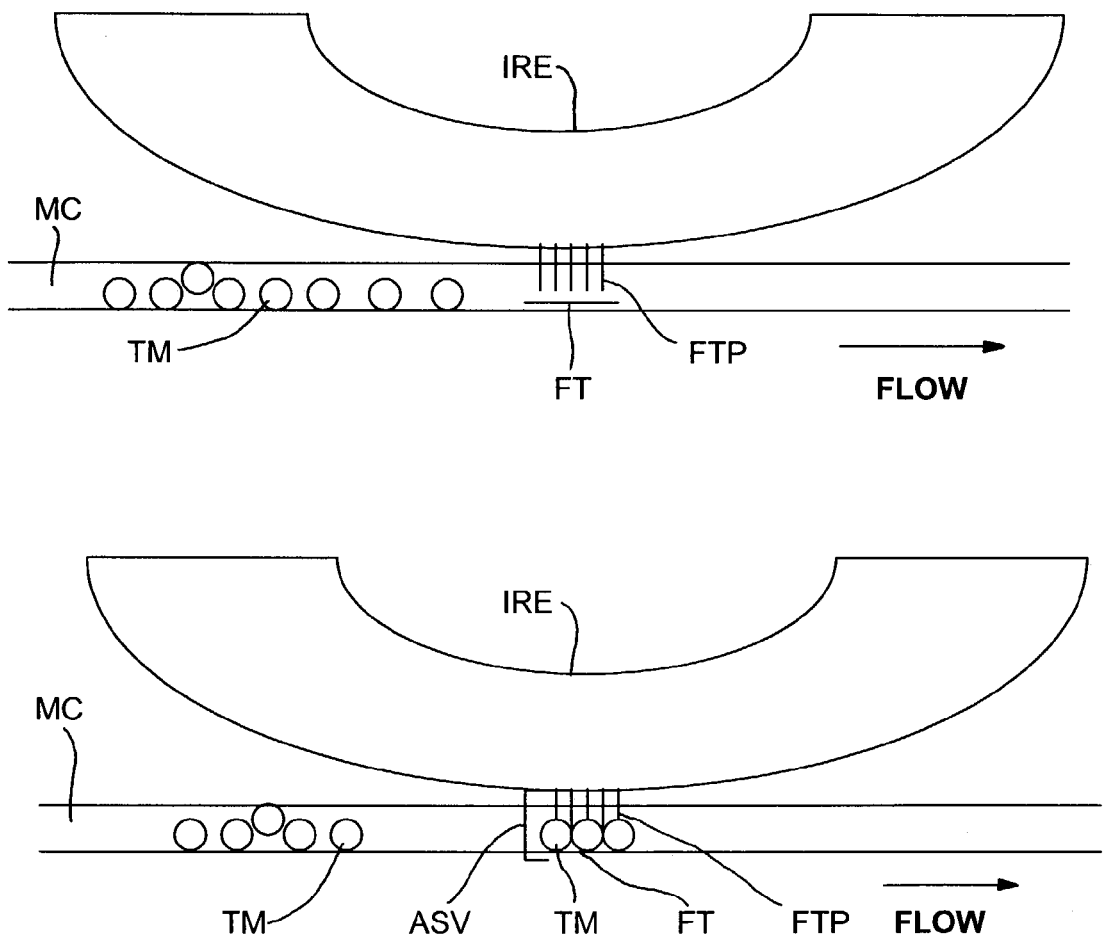
FIG. 7 is a schematic diagram depicting the use of a functionalized tip in conjunction with a microfluidic channel.

In preferred embodiments, such as those shown in FIGS. 5A and 7, a liquid sample impinges on a functionalized tip probe FTP. A sample can be applied via a microfluidic channel MC (or syringe) disposed so as to direct the flow of sample to functionalized tip probe FTP. Target molecules TM in the sample that can favorably interact with functionalized tip probe FTP preferably becomes associated with probe FTP, while target molecules TM that do not interact favorably with functionalized tip probe FTP do not associate with probe FTP and are washed from the region of probe FTP, as shown in FIG. 7. Following the association of the sample with functionalized tip probe FTP to form an active sample volume ASV, a single pass FTIR-ATR spectrum of the sample can be acquired and analyzed in accordance with the methods of the present invention. The capture of sample from the liquid stream is one way of effectively concentrating the sample to form an active sample volume ASV, thereby providing a high signal-to-noise ratio. By employing a functionalized tip FT in conjunction with the single pass FTIR-ATR methods of the present invention, as little as femtomoles of sample can be studied in the active sample volume ASV.

III.E.3. Functionalized Tip Probe Design and Application

The functionalized tip can employ, for example, a charged surface or a surface-attached sugar, small molecule, protein or DNA molecule that serves as a binding site for the target molecule of interest (usually a protein), although other chemical entities will be apparent to those of skill in the art upon consideration of the present disclosure. These chemical entities can be associated with the IRE of a single-pass FTIR-ATR apparatus and method of the present invention. In this way the tip itself becomes a probe of protein properties as well as structure.

In an preparation for an experiment in which it is desired to study the surface charge on a protein delivered by syringe or microfluidic device to the functionalized tip, negatively charged surfaces can be prepared, for example, with carboxylate self-assembled monolayers and positively charged surfaces, for example, can be prepared with amine-terminated self-assembled monolayers. In this representative approach, neutral surfaces with enhanced biocompatibility can also be prepared using, for example, alcohol terminated or polyethylene glycol terminated self-assembled monolayers. Positively charged proteins (e.g. cytochrome c or bovine serum albumin) are attracted to negatively charged surfaces and give a single pass FTIR-ATR signal. Conversely, such proteins are repelled by a positively charged surface. Thus, a comparison of the data acquired from two or more tips, each of which is functionalized with a chemical entity having a different charge profile, can-be employed to determine the protein's surface electrostatic charge.

The specificity of a functionalized tip can be increase by employing particular molecules attached to its surface. For example, carbohydrates, proteins, and DNA can be used in a spectroscopic binding assay. The single pass FTIR-ATR signal will differ from the background if a protein binds to the surface-attached molecule. The surface-attachment concept can be expanded to include multiple repeat sequences of DNA. This geometry permits a large number of binding sites to be concentrated in the active volume of the ATR crystal to maximize the signal. The functionalized tip, in conjunction with the single pass FTIR-ATR apparatus and methods of the present invention can provide high quality spectra of DNA binding proteins of all types, including transcription factors, polymerases, telomerase, telomeric binding proteins and other DNA binding proteins.

In a similar fashion, an appropriately prepared functionalized tip can be employed to study RNA and RNA binding proteins. In this application the self-assembly properties of DNA can be used to generate multiple repeat structures and can include loops, hairpins, and junctions. Thus, the binding of proteins to structures other than B-form linear DNA can also be measured.

Figure 9:
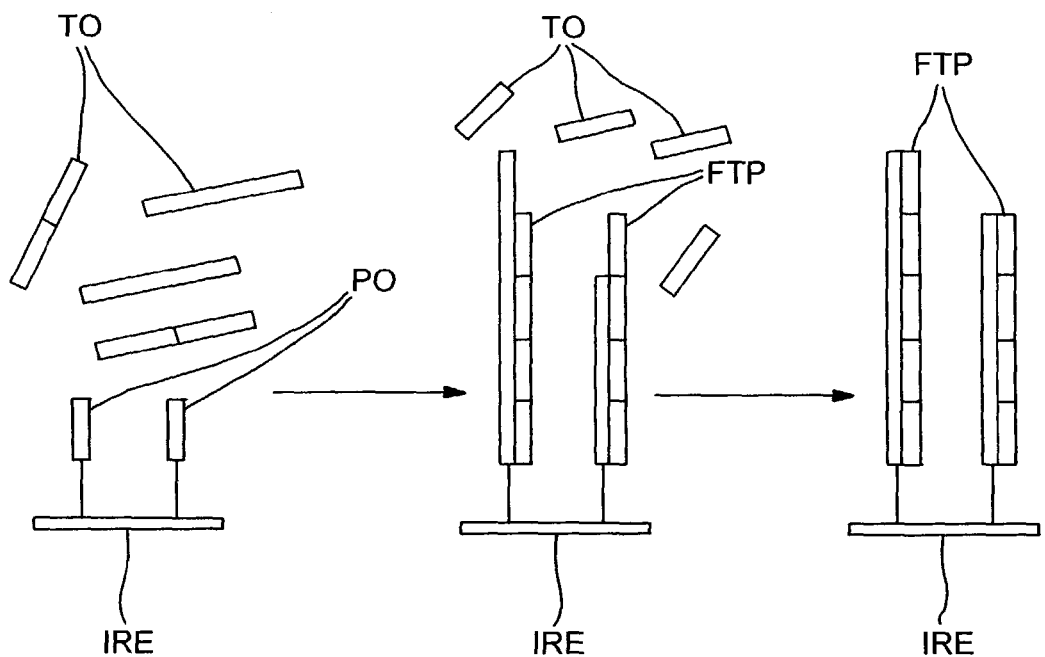
FIG. 9 is a schematic diagram depicting a preferred method of generating multiple repeat oligonucleotide structures.

A preferred method of generating multiple repeat oligonucleotide structures is depicted in FIG. 9. In FIG. 9, primer oligomers are attached to a site, for example internal reflecting element IRE. Next, template oligos TO are added and allowed to hybridize with the primers PO and themselves. T4 ligase (or other suitable ligase) is then added to join oligos TO to form a functionalized tip probe FTP, and unassociated oligos are washed away. Finally, probes FTP are capped with single stranded oligos and joined using T4 ligase.

When proteins and carbohydrates are studied, a suitable technique can employ the attachment of a sugar, oligosaccharide, peptide or protein at various points on a polymeric chain of association sites at which a sample can associate with the protein or carbohydrate. In a preferred embodiment, these sites can be prepared using DNA as a scaffold or synthetic methods can be employed. Additionally, as presented in FIG. 5B, a similar scaffold structure can be employed to support a plurality of protein binding sites BS.

Figure 8:
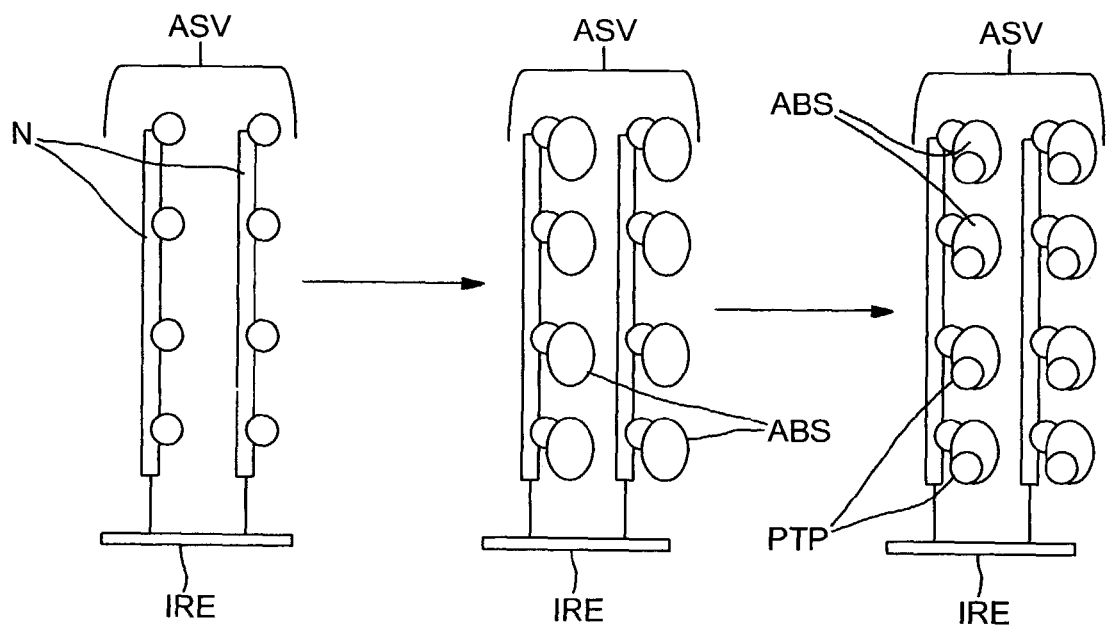
FIG. 8 is a schematic diagram depicting a preferred method of forming polymeric polyethylene glycol nickel-nitrilotriacetic linkers.

In another embodiment depicted schematically in FIG. 8, multiple repeat units of the nickel-nitrilotriacetic (NiNTA) acid binding site ABS for polyhistidine tagged proteins PTP can be employed to functionalize the active volume ASV of the FTIR-ATR objective IRE with binding sites for a protein of interest. In this embodiment, polyethylene glycol NTA polymers N can be synthesized and associated with active volume ASV. Subsequently, nickel can be associated with the polymers to generate one or more NiNTA binding sites ABS, which will be recognized by histidine-tagged proteins PTP, which are known to associate with nickel atoms.

Figure 5B:
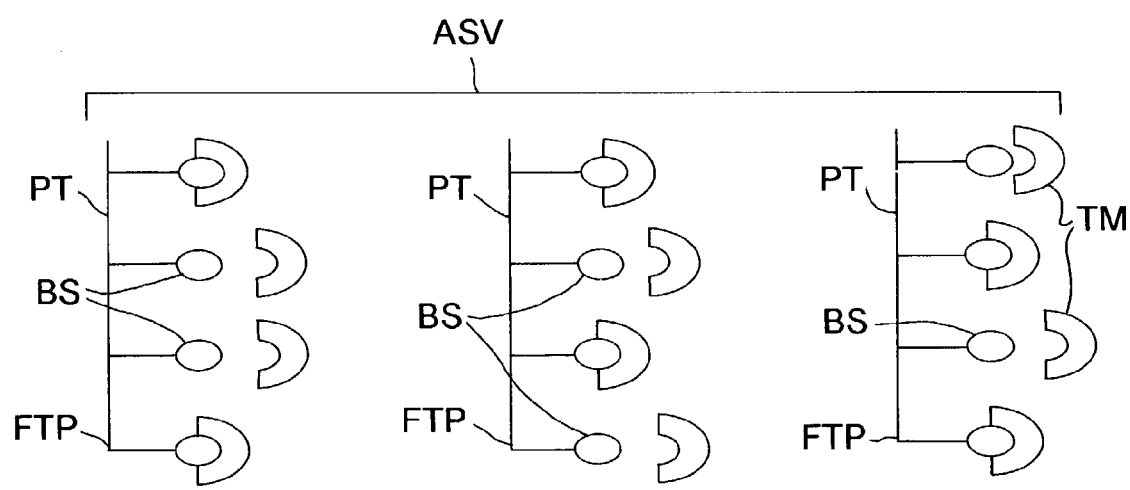
FIG. 5B is a schematic diagram depicting the use of a functionalized tip to study protein-protein interactions.

Referring again to FIGS. 5A and 5B, the addition of a protein sample comprising target molecules TM is shown schematically using a microfluidic channel MC. Target molecules TM (represented by horseshoe-shaped objects) bind to binding sites BS (represented by ovals). Binding sites BS comprise a functionalized tip probe molecule and can be a protein, oligonucleotide, carbohydrate or other small molecule ligand known or suspected to associate with a target molecule TM. A polymeric tether PT holds multiple repeat binding sites to form and maintain functionalized tip probe FTP within about one micron of the surface of objective O, as depicted in FIGS. 5A and 5B. When multiple repeat binding sites BS are employed, a preferable spacing for probe FTP is 10-30 nm. In this arrangement, 30-100 copies of binding site BS can be located on each polymer PT that resides within active volume ASV (i.e. the volume from which a single pass FTIR-ATR spectrum is acquired via a single pass of an infrared beam IRB in accordance with the present invention).

IV. Procedure for Generating a Spectrum

The methods for acquiring an IR spectrum, analyzing an IR spectrum and generating information about secondary structure disclosed in the present invention generally employ single-pass FTIR-ATR techniques. Single-pass techniques permit convenient spectral subtraction of water from a composite spectrum to reveal the amide A or N—H stretching region of the spectrum (3200 to 3500 $cm^{-1}$), the aliphatic amino acid region of the spectrum (2800 to 3000 $cm^{-1}$) and all remaining protein bands in the 2800 $cm^{-1}$ to 50 $cm^{-1}$ region of the spectrum.

In practice, subtraction of the water spectrum from a composite spectrum can be achieved by comparing the spectra obtained from samples comprising a target sample (i.e. a target protein) at varying sample concentrations and subsequently performing a singular value decomposition to determine the spectral components that can be attributed exclusively to the target sample. In multi-pass FTIR-ATR, however, aqueous solvents can be problematic because a solvent signal can build up with each pass, or "bounce", of the irradiating IR radiation and ultimately dominate the spectral contributions of a sample. On the other hand, the single-pass methods disclosed in the present invention, limit solvent contributions to a spectrum by limiting the extent of interaction of incident radiation with a solvent to one pass and thus, only one interaction. Thus, single-pass methods of acquiring an IR spectrum can be desirable because there is a minimal chance for solvent buildup due to the single bounce of the IR radiation.

The procedure for acquiring a single-pass IR spectrum follows generally established methods that will be apparent to those of skill in the art of spectroscopy upon consideration of the present disclosure. The specific details of the procedure are governed by the parameters of the equipment and the nature of the experiment, but a general methodology is described herein below. Additionally, the disclosed general methodology can be adapted to the various properties of the sample under study and other pertinent experimental considerations.

IV.A. Sample Preparation

Sample preparation will vary with the nature of the sample, but can proceed generally as follows. A sample can first be isolated and purified. In a preferred embodiment, the sample is a protein. Suitable isolation and purification methods can be tailored to a given protein and will be known to those of skill in the art. An appropriate purification scheme for a given sample can be found, for example, in the relevant literature. When no established protein purification protocol exists, general strategies of protein purification known to those of skill in the art can be employed in the present invention. See, e.g., Harris & Angal (eds.), (1989) *Protein*

*Purification Applications: A Practical Approach*, IRL Press; Janson & Rydén (eds), (1998) *Protein Purification: Principles, High Resolution Methods, and Applications,* 2nd ed., Wiley-Liss, New York.

Sample purity can be a significant concern, since even slight impurities can lead to false and/or artifactual features in an acquired spectrum. Thus, it is preferable that a sample is substantially pure before introduction to a sample cell. The methods of the present invention, however, facilitate a background subtraction operation, which can be performed as needed to remove background signal. For example, a background subtraction can be performed where the buffer in which the sample is disposed is known.

FTIR generally benefits form relatively high sample concentrations. Therefore, following purification of a sample, a sample can be further concentrated as desired using standard sample concentration methods. For example, if a sample comprises protein, the sample can be concentrated using a pressurized filter apparatus such as the AMICON™ filtration apparatus, available from Millipore Corp. of Bedford, Mass. When using pressurized filtration apparatus, a desired pressure can be supplied by nitrogen, argon or other inert gas. When filtration approaches such as pressure filtration and gel filtration chromatography are employed, an appreciation of the size of the protein being purified can also be helpful, in order to choose a filtration matrix with an appropriate pore size. Other methods of protein concentration, such as partial lyophilization or evaporation of solvent by exposure to a nitrogen gas stream, can be used if such methods are known or suspected not to compromise the integrity of a sample.

As noted, when acquiring an IR spectrum by employing the present inventive methods, it can be advantageous to be able to concentrate the sample, such as in a dry nitrogen atmosphere, in order to increase the signal intensity. In an automated microfluidic delivery system, such as that described herein, concentration of a sample can be accomplished by stopping the flow and lowering the cell away from the IRE by a few microns, using a stepper motor. The surface tension of the liquid sample draws the sample out with the IRE through a hole as indicated by the identified spot in the microfluidic system depicted in FIG. 4. After waiting several seconds, the sample becomes more concentrated in the dry nitrogen atmosphere so that higher quality spectra can be obtained. This method can be automated under computer control to prevent drying of the sample to a film.

When a desired level of evaporation has been achieved, or the sample has been concentrated to a desired amount, the sample can be re-immersed in the microfluidic channel. As described herein, one of the advantages of the single-pass FTIR-ATR methods of the present invention is that proteins that are soluble in aqueous solutions at the level of 5 mg/ml can be observed directly in solution. The solution can be subsequently concentrated, and the concentration process (i.e. the degree of hydration) can be continuously monitored via the infrared absorption bands for signs of change due to denaturation or dehydration of the sample. This creates a robust method for obtaining high quality spectra of very small amounts of sample. For example, if a protein sample has a concentration of 5 mg/ml, a molecular weight of 25,000 and a solution volume of 25 picoliters, only 50 femtomoles of this protein need be disposed in the observation region of the cell, as demonstrated by the data depicted in FIGS. 2A and 2B. In addition, this capability can be useful for monitoring protein hydration and denaturation states in protein films using a highly stable environment in which the sample can be cycled between hydrated and dehydrated states.

IV.B. Sample Introduction

Following isolation and concentration (if desired) of the sample, the sample can be introduced into a sample cell. In one embodiment of the present invention, a suitable sample cell can be milled from a block comprising PTFE sold under the registered trademark TEFLON® by E. I. DuPont DeNemours and Company of Wilmington, Del. However, other polymeric materials or even metals can be used. It should be noted that an aspect of the present invention is the absence of any requirement that a sample cell be transparent to IR radiation. As noted hereinabove, an aspect of the present invention is the use of an ATR crystal, which lies on top of or directly under the sample. Thus, a suitable sample cell need only be adapted to accommodate an IRE, which is preferably oriented so as to be flush with the sample.

The absence of any requirement for sample cell transparency allows a sample to be introduced into a variety of sample cells, for example, a depression in a block comprising PTFE sold under the registered trademark TEFLON® by E. I. DuPont DeNemours and Company of Wilmington, Del. under an IRE. This freedom in the selection of a sample cell facilitates selecting a material to which the sample can be easily introduced and from which the sample can be easily recovered. Sample introduction generally involves injecting a sample into a selected sample cell via a syringe, automatic pipetter, or other device; the sample cell is preferably oriented in a location such that it is disposed to be in contact with an IRE when the crystal is in a position for data acquisition. A sample can be conveniently removed from the sample cell in the same way it was introduced, following data acquisition.

In one aspect of the present invention, sample introduction and removal can be automated by fitting the apparatus with an automated robotic sample injection system. Automated injection systems can significantly increase the rate at which spectra can be acquired. Additionally, sample acquisition parameters can be uniform from run to run, due to the internal consistency achievable using an automated injection system.

Alternatively, when a functionalized tip FT is employed, the IRE can be positioned proximate to a microfluidic channel MC, as depicted in FIG. 7. Referring to the upper panel of FIG. 7, a sample comprising target molecule TM can then be passed through microfluidic channel MC (defined by the horizontal tube) toward a functionalized tip probe or probes FTP (the small vertical lines below the IRE). The direction of flow is indicated.

The lower panel of FIG. 7 shows the interaction of the target molecule TM in the sample with a plurality of functionalized tip probes FTP. The use of a plurality of functionalized tip probes can increase the effective concentration for spectrum acquisition by localizing an amount of sample in the active volume ASV. Following an interaction of target molecule TM with one or more functionalized tip probes FTP, a single pass FTIR-ATR spectrum can be acquired and analyzed by employing the single pass FTIR-ATR apparatus and methods of the present invention.

IV.C. Acquiring an IR Spectrum

The exact procedure for obtaining a spectrum can vary with the equipment comprising the experimental configuration. Thus, the specific details for collecting IR spectra and other data can be dependent on the equipment but generally comprise irradiating an IRE, which is disposed above and in contact with a liquid sample, with IR radiation and monitoring the radiation reflected from the IRE. Reflection data can be stored on a suitable medium and/or can be displayed on a computer screen or on chart paper. IREs can be selected so as to facilitate single-pass acquisition of spectra, to the exclusion of multi-pass generated spectra. Preferably the source of IR radiation is an FTIR microscope or an attachment designed to fit in the sample compartment of an FTIR bench or as an external accessory. Representative spectra acquired by employing the methods and apparatus of the present invention are presented in FIGS. 6 and 10-12.

IV.D. Mathematical and Statistical Analysis of an Acquired IR Spectrum

A spectrum acquired using the apparatus and methods of the present invention can initially comprise a signal arising from the interaction of IR radiation with a sample, such as a protein, and the solvent in which the sample is disposed. In order to ascertain a degree of secondary structure present in a sample, it is helpful to mathematically subtract any spectral component attributable to the solvent signal. As noted, a preferred solvent for biological samples, such as proteins, comprises an aqueous buffer. An aqueous buffer can comprise compounds present in addition to the buffer. Phosphate buffered saline (PBS), Tris, HEPES and other compounds are commonly used to buffer solutions comprising biological molecules. Subtraction of the buffer component can be achieved by subtracting a spectrum of the buffer in the absence of a sample from the spectrum of the sample in the presence of buffer (i.e. the composite spectrum).

Signals attributable to water can dominate those regions of an IR spectrum that are the most informative regions for the analysis of biological molecules. Thus, in order to identify a component of a spectrum corresponding to an absorption by a biological molecule, it is often desirable to remove the water component from the sample-solvent composite spectrum. This can be achieved by mathematically subtracting the water component, which will have been spectrally analyzed previously, from the spectrum of the sample in the presence of water. Such a subtraction can be accomplished using the techniques described below.

IV.D.1. Mathematical Subtraction of Signals

The water component can be removed from an IR spectrum by subtracting spectrum of water from the spectrum of a sample in the presence of water. Often, this is problematic because of the significance of the water contribution. Subtraction can also have the undesired effect of removing a degree of the sample contribution as well and can have the effect of removing desirable information from a spectrum. The present invention solves this problem, in part, though the use of single-pass FTIR-ATR methods. Single-pass FTIR-ATR can decrease the overall magnitude of the water contribution and thus minimize the undesirable loss of information when a water spectrum is subtracted from the composite spectrum, which comprises the sample in the presence of water.

A similar procedure can be performed to remove unwanted spectral features arising from the presence of material other than the sample. In this application, a spectrum of the buffer (which can comprise any additional components) can be subtracted from a spectrum acquired from a sample disposed in the buffer.

When performing a spectral subtraction operation, the operation is preferably performed on a computer system. Preferably, the subtraction operation comprises an algorithm that identifies (or allows a user to identify) regions of a composite spectrum for subtraction. After identifying regions to be subtracted, the subtraction is performed to generate a resultant difference spectrum. Preferably the difference spectrum can be presented graphically or tabulated as a function of absorbance at a given wavelength and presented in tabular form.

IV.D.2. Correlation of Protein Structure and Spectroscopy

Identification and quantitation of protein secondary structure has been performed previously via multivariant calibration. Douseeau & Pezolet; (1990) *Biochem.* 29: 8771-79; Chittur, (1998) *Biomaterials* 19: 357-69; Pribic, (1994) *Anal. Biochem.* 223: 26-34. Multivariant calibration generally comprises collecting spectra from protein samples having a known conformation and using these spectra to develop a regression model to facilitate prediction of secondary structure in unknown proteins. The regression model functions essentially as a calibration curve. Various regression models such as classical least squares, principal component regression (PCR), and partial least squares (PLS) are described in the art. Douseeau & Pezolet; (1990) *Biochem.* 29: 8771-79; Chittur, (1998) *Biomaterials* 19: 357-69; Pribic, (1994) *Anal. Biochem.* 223: 26-34; Faber & Kowalski, (1997) *J. Chemometr.* 11: 181-238. PCR and PLS are the preferred regression models, since they are more stable than classical least squares, and they allow for the use of more wavelengths than calibration samples. Faber & Kowalski, (1997) *J. Chemometr.* 11: 181-238; Gemperline, (1997) *Chemometrics Short Course*, pp. 66-75.

PCR is a preferred model for application in the present inventive methods. The first step of PCR involves calculating a principal component model for the calibration samples as shown in Equation 1, where $A_{std}$ corresponds to the absorbance values for the calibration set, U signifies the column-mode eigenvectors, the square root of the diagonal of S represents the eigenvalues, and $V^T$ denotes the row-mode eigenvectors.

$$A_{std} = USV^T \quad \text{(Eqn. 1)}$$

Each calibration standard will have an associated vector, $C_{std}$, which typically indicates concentration, however in the context of the present invention, $C_{Std}$ signifies the secondary structure content.

In order to illustrate such a correlation, the protein ribonuclease A can be used as a specific model protein. Ribonuclease A is known to comprise a 17.7% α-helical component and a 33.1% β-sheet component. Oberg & Fink, (1998) *Anal. Biochem.* 256: 92-106. Therefore, the corresponding conformational content vector for ribonuclease A will contain one of these values, depending upon whether the protein's secondary structure is being solved for α-helical content or the β-sheet content. The extent to which each of these secondary structure forms are present in a protein can be identified by solving one or more equations comprising variables representing these structural components, either simultaneously or one at the time.

A regression vector is calculated once the correct number of factors, which are representative of chemical components, is determined. Such a determination will be based on the eigenvalues extracted from the principal component model (the PCR-generated model). The value of regression vector b can be determined by solving Equation 2. Gemperline, (1997) *Chemometrics Short Course*, pp. 66-75.

$$b = VS^{-1}U^T c_{std} \quad \text{(Eqn. 2)}$$

A prediction step based on the values of known standards (i.e. the percent helical and percent sheet components) can be performed using Equation 3, such that the standard error of calibration (SEC) can be determined.

$$C_{pred} = A_{std}b \quad \text{(Eqn. 3)}$$

The prediction of the unknown conformations of proteins of Equation 4, $C_{pred}$, is analogous to $C_{pred}$ of Equation 3. In Equation 4, $A_{unk}$ represents the absorbance values of the unknown (Gemperline, (1997) *Chemometrics Short Course*, pp. 66-75), whereas in Equation 3, $A_{std}$ represents the absorbance values of the standard (i.e ribonuclease A).

$$C_{pred} = A_{unk} b \qquad \text{(Eqn. 4)}$$

The partial lease squares method (PLS) is analogous to PCR, however, a difference is found in the calculation of the projection vector. Faber & Kowalski, (1997) *J. Chemometr.* 11: 181-238; Gemperline, (1997) *Chemometrics Short Course, pp.* 66-75; Douseeau & Pezolet, (1990) *Biochem.* 29: 8771-79. Both methods can be performed to construct regression vectors for the prediction of secondary structure. The application of PCR and PLS involving the amide I region are disclosed herein; however, the single-pass attenuated total reflection FTIR method can include all of the spectral information in the spectral range of 50 $cm^{-1}$ to 3700 $cm^{-1}$.

IV.D.3. Deconvolution of an Acquired Spectrum

It might also be desirable to determine the intensity of a signal at a certain frequency. Such a value can be calculated using deconvolution techniques known to those of skill in the art. For example, protein and other samples can be analyzed by Fourier self-deconvolution, second derivative spectroscopy, and Gaussian band fitting techniques to determine the frequency components present. Such deconvolution techniques have been repeatedly proved to be reliable techniques for acquiring spectral information from complex spectra.

IV.E. Signal Intensity, Signal-to-Noise and Protein Stability Considerations

Single-pass FTIR-ATR has a lower signal intensity than other methods for a given protein concentration due, in part, to its single interaction with a sample. The effective pathlength in an FTIR-ATR experiment, which is the penetration-depth of an evanescent IR wave, can be less than one micron (one millionth of a meter or about 0.00004 inches) and by the definition of single-pass, there is only one interaction with the sample. This is in contrast to the multiple interactions of multi-pass FTIR-ATR, which can generate a greater signal due to multiple interactions with the sample.

The present invention facilitates the real time observation of various processes, as well as the acquisition of spectra exhibiting various regions that are normally difficult to observe, due to strongly overlapping water signals. In one example of a process that can be observed in real time, the sample dehydration process can be monitored in real time and data recorded at levels that permit qualitative and quantitative analysis. Although analysis of some protein films compared to the analysis of the proteins in aqueous solution reveals no change in secondary structure upon dehydration, it is likely that unstable proteins could denature during dehydration. Jongh et al., (1996) *Anal. Biochem.* 242: 95-103; Oberg & Fink, (1998) *Anal. Biochem.* 256: 92-106. Protein stability is not an absolute necessity for the present invention, due to the ability of the present invention to detect conformational changes in real time as the protein denatures, with a high signal to noise (S/N) ratio. This ability permits a researcher to sufficiently dehydrate a sample for optimum signal enhancement, without disrupting the native secondary structure of the protein. This also permits a spectrum to be acquired under a wide variety of experimental conditions, such as in the presence of different buffers or even in the presence of denaturants or other potentially deleterious compound. Spectra acquired at various levels of hydration can be acquired with high S/N ratios and strong sample signal compared with solvent signal.

V. Automation of the Spectrum Acquisition Process

In the various disclosed embodiments of the present invention, sample delivery, sample removal and data acquisition are preferably automated. As noted throughout the present disclosure, the present invention is directed to acquiring spectra of samples in solution, which are subsequently processed to determine the presence and quantity of secondary structure in the sample. Thus, samples studied using the present invention are preferably in liquid form. This fact makes sample manipulation easier, due to the availability of robot sample transfer systems. It is therefore an aspect of the present invention to provide or modify a commercially available injection system (such as those available from Isco, Inc. of Lincoln, Nebr. and from PerkinElmer Corp. of Wellesley, Mass.) to perform the steps of the present inventive methods in an automated fashion.

In one disclosed embodiment of the present invention, the process of acquiring a spectrum of a sample is automated. Suitable commercially available software packages for automated spectrum acquisition include the WINFIRST™ package available from Thermo Mattson of Madison, Wis., and the AUTOPRO™ software package available from Pike Technologies, Inc. of Madison, Wis. These software packages can be employed to automate spectrum acquisition and can be useful for analyzing large numbers of samples.

In another embodiment, the present invention is fully automated and can comprise an autosampler to inject and remove samples and a spectrum acquisition software package to run an FTIR microscope or FTIR bench accessory. Additionally, the identified software packages can be modified, or software can be written or purchased, to perform the various mathematical and statistical operations that can be performed when acquiring data by employing the present inventive methods. For example, software can be provided and employed to analyze an acquired spectrum, whereby the water component is automatically subtracted from the spectrum and the quality and quantity of secondary structure is subsequently identified using algorithms referred to, incorporated and disclosed herein. In this embodiment, a researcher can simply prepare the autosampler, configure the software and begin the process.

One of the advantages of the apparatus and methods disclosed herein is that they facilitate the acquisition a spectrum in a very short time. This property, coupled with the automation equipment described above, facilitates the analysis of a large number of samples in a short period of time without the need for an operator to oversee or perform the processes. The hardware and software packages described above can be written or purchased and can permit the automation of spectrum acquisition and/or analysis processes. The consistency and rapidity of automated acquisition and analysis also facilitates high throughput sample screening and analysis.

VI. Applications of the Present Invention

The present invention has a range of applications. A representative but non-limiting list of examples includes generation of a spectrum library, performance of high throughput analyses, monitoring chemical reactions and the characterization of proteins, particularly in terms of a protein's secondary structure content. Although these applications are described hereinbelow, additional applications of the present invention will be apparent to those of skill in the art upon consideration of the present disclosure.

VI.A. Generation of an IR Spectral Library

In aqueous solutions, the background absorption of the solvent is large, even in sample cells with thin spacers. Subtraction of water can be extraordinarily difficult if the absorbance of the water bands is larger than 0.5. Difficulties are encountered not only due to the non-linearity of the mercury cadmium tellurium (MCT) detector response, but artifacts due to the large size of the water signals relative to the protein bands can also be present. To circumvent these problems some investigators have employed a multi-pass ATR crystal and allowed the sample to become dehydrated in order to decrease the water background. This process has the significant drawback that the signal is unobservable until the sample is nearly a gel, due to large $H_2O/D_2O$ background signals. Thus, there is no convenient reference to determine the shape of bands in a sample that is fully hydrated. The present invention solves this and other problems, and can thus be used to generate an IR spectrum library comprising various regions of the IR spectrum, including those regions typically masked by a large solvent signal.

Figure 2A:
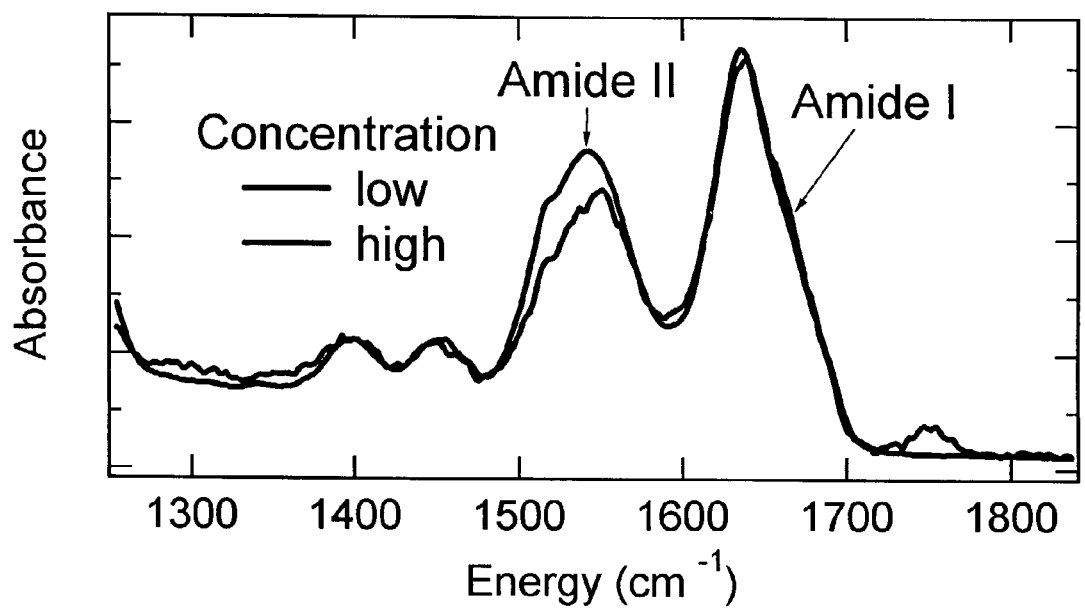
FIG. 2A is a graph of a mid-frequency IR spectrum of a protein comprising β-sheet structure. Low and high protein concentrations were studied using a single-pass FTIR-ATR method of the present invention. Representative spectra are depicted in the figure. Various spectral features are visible.
Figure 2B:
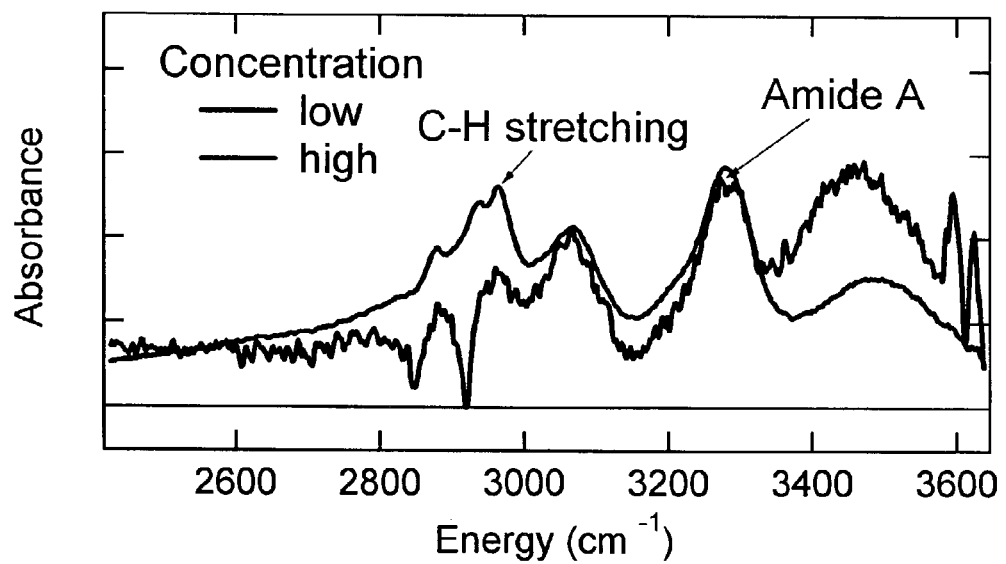
FIG. 2B is a graph of a high-frequency IR spectrum of a protein comprising β-sheet structure. Low and high protein concentrations were studied using a single-pass FTIR-ATR. Representative spectra are depicted in the figure. Various spectral features are visible.

FIGS. 2A and 2B depict both the mid-frequency and high frequency regions, respectively, of the IR spectrum of a β-sheet forming protein, which was acquired by employing an FTIR-ATR method of the present invention. Spectra were acquired from both high and low concentration protein samples. The mid-frequency FTIR spectrum of FIG. 2A comprises the amide I band, the amide II band and at least two other bands. The various features of the high and low concentration spectra depicted in FIGS. 2A and 2B suggest that the present invention can be used to determine changes in protein structure that occur at different degrees of hydration. This ability is important because multi-pass FTIR-ATR microscopy is often performed on proteins that have been dehydrated before acquiring a control spectrum of the protein prior to dehydration.

The bands in the mid-frequency region have been studied extensively, particular the amide I band, which is referred to as the amide I' band when the sample is disposed in $D_2O$. Many studies have been carried out in $D_2O$, because the water bending mode is observed at 1640 $cm^{-1}$, which is the same frequency range where the amide I band appears. However, $D_2O$ spectra do not necessarily represent the true native state of a protein and, as noted, the solvent peak dominates spectra of protein samples disposed in aqueous solutions. The single-pass FTIR-ATR methods of the present invention circumvent this problem because, when single-pass FTIR-ATR is employed, the water bands that overlap the amide I bands are small enough that very good spectra of proteins disposed in aqueous solution can be acquired.

Figure 3A:
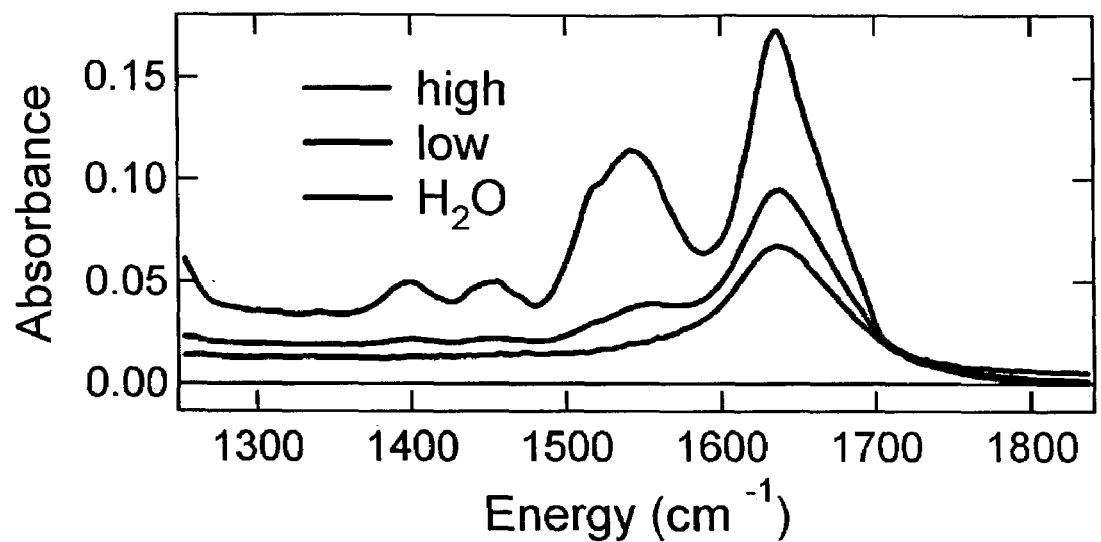
FIG. 3A is a graph of a mid-frequency IR spectrum of a protein comprising β-sheet structure. Low (middle line) and high (upper line) protein concentrations, as well as water (lower line) were studied using a single-pass FTIR-ATR method of the present invention single-pass FTIR-ATR. Representative spectra are depicted in the figure. Various spectral features are visible.
Figure 3B:
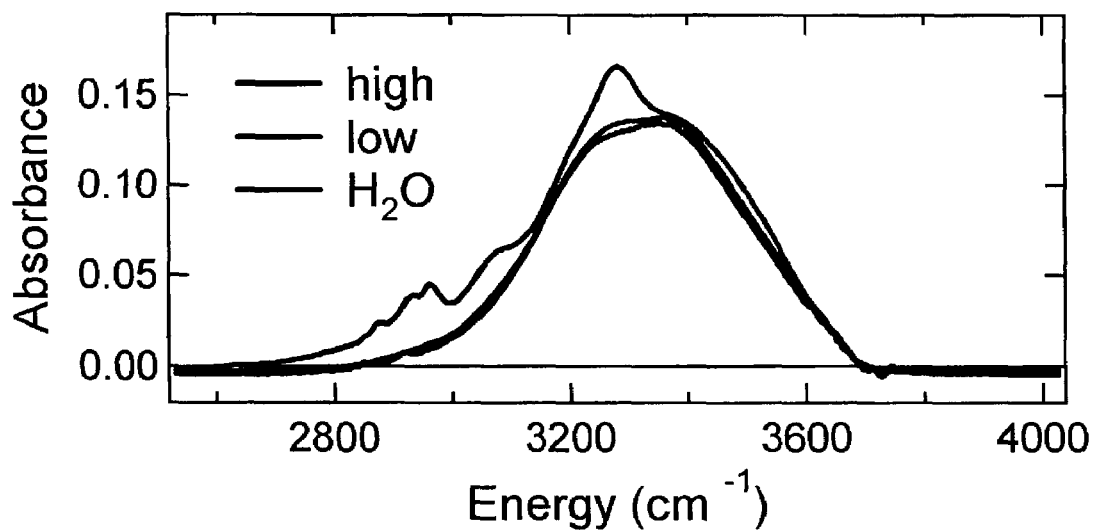
FIG. 3B is a graph of a high-frequency IR spectrum of a protein comprising β-sheet structure. Low (middle line) and high (upper line) protein concentrations, as well as water (lower line) studied using a single-pass FTIR-ATR method of the present invention. Representative spectra are depicted in the figure. Various spectral features are visible.

FIGS. 3A and 3B depict FTIR-ATR spectra of the same protein sample that was studied to generate the spectra of FIGS. 2A and 2B. In FIGS. 3A and 3B, the $H_2O$ background is identifiable and the spectrum is depicted prior to subtraction of the $H_2O$ background. The absorbance units shown on the X-axis in FIGS. 3A and 3B are representative of the measured values. Thus, water can be successfully subtracted from the spectra because the absorbance is only about 0.07 for H—O—H bend (in the region of 1640 $cm^{-1}$) and only about 0.15 for the symmetric and anti-symmetric O—H stretching vibrations (in the regions of 3260 and 3350 $cm^{-1}$, respectively). These small absorbance values can be subtracted from a composite spectrum with the confidence that no significant spectral information will be lost in the subtraction operation. Following the application of these and other mathematical operations and treatments, the resulting spectra can be compiled in a database as a library of IR spectra. Preferably the database is an electronic database and is searchable based on an indexing system that takes into account the various features of a spectrum.

Another aspect of the present invention is to extend the ability to acquire spectra of the amide I, amide II and other IR spectral regions, to encompass the acquisition, analysis, correlation of these and other spectral features with secondary structure, and the compilation of this information. By employing the FTIR-ATR methods disclosed in the present invention, spectra from a range of protein samples can be acquired, analyzed, the spectral features correlated with existent secondary structure, and the information compiled to generate a library of the protein secondary structure components of the proteins when the protein is disposed in an aqueous solution. Kumosinski & Unruh, (1994) in *ACS Symposium Series 576, Molecular Modeling: From Virtual Tools to Real Problems*, (T. Kumosinski & Liebman, eds.) pp. 71-98; Susi & Byler, (1986) *Method. Enzymol.* 130: 290-311; Byler & Susi (1986) *Biopolymers* 25: 469-87; Dousseeau & Pezolet, (1990) *Biochem.* 29: 8771-79; Purcell & Susi, (1984) *J. Biochem. Bioph. Meth.* 9: 193-99; Susi, (1972) *Method. Enzymol.* 26 Pt.C: 455-72; Jongh et al., (1996) *Anal. Biochem.* 242: 95-103; Susi et al., (1985) *J. Biochem. Bioph. Meth.* 11: 235-240.

A number of proteins are commercially available and can be used to generate spectra of proteins representative of proteins comprising various proportions of secondary structure. For example, representative proteins can be selected that comprise significant α-helical content or significant β-sheet content, and proteins can be selected that comprise significant amounts of both. Such spectra can serve as standards or "benchmarks" in a library of IR spectra. The features of such spectra can also contribute to the development of an algorithm correlating structure with spectral features. Representative proteins that comprise significant α-helical structure and can be useful as representative of this form of secondary structure include cytochrome C, myoglobin, concanavalin A, and hemoglobin. The proteins trypsin, immunoglobulin G, α-chymotrypsin, and chymotrypsinogen A comprise significant β-sheet structure and can be used as representative of this form of secondary structure. Proteins that comprise both α-helical and β-sheet structure, such as ribonuclease A, ribonuclease S, lysozyme, and papain, can also be used as representative of their composite heterogeneous secondary structure.

Other information that can be included in an IR spectrum library is a comparison of the IR spectra of proteins acquired using the single-pass FTIR-ATR methods of the present invention with IR spectra of the same proteins acquired in $D_2O$ using conventional FTIR spectroscopy techniques. Such a comparison can be made by obtaining proteins of interest, hydrating them, acquiring spectra and comparing the spectra with those spectra available in the literature or known to those of skill in the art of IR spectroscopy. An error analysis can be carried out to determine the reproducibility of spectra obtained in at least ten replicates for each of three or more samples. Such an error analysis can validate a reliability comparison of spectra acquired when a protein sample is disposed in water in view of protein spectra acquired when the sample is disposed in $D_2O$. This approach facilitates a significant improvement in reproducibility.

In addition, new data on spectral bands that have not been heretofore resolved can be included in an IR spectrum library. Identification of previously unidentified spectral bands can be of great assistance in the identification of a sample and its secondary structure based on its spectrum. In fact, the presentation of such data can form as significant aspect of an IR spectrum library.

The present invention can, therefore, provide the foundation of a database and can be employed in conjunction with a spectral acquisition and/or analysis software package that can accompany both automated and routine use of a single-pass FTIR-ATR instrument. Suitable software packages are commercially available and can include SCANTRAQ BASIC™ software package available from FTG Software Associates of Princeton, N.J. and GRAMS/32™ Version 5.2 software package, available from ThermoGalactic of Salem, N.H. or suitable software can be written to perform desired operations. Furthermore, unique spectral features and structure correlations, as described herein below, can be incorporated into a proteomic/bioinformatic-based approach to deducing tertiary and quaternary structure. A proteomic/bioinformatic-based approach can, for example, be based on the spectral, sequence and secondary structure information that can be generated by the single-pass FTIR-ATR methods disclosed in the present invention.

In yet another aspect of the single-pass FTIR-ATR techniques of the present invention, a spectrum can be acquired from of a protein expressed in cells or genetic recombinants and compared with a previously acquired spectrum in a screening-type procedure. In this embodiment, an IR spectrum library constructed in accordance with the present invention can be used as a basis of comparison. Sample spectra can be acquired as described herein and compared with an IR spectrum database in under a rigid or flexible scheme of comparison. For example, when a researcher desired to ascertain the presence of a given protein in a cell, the identification criteria, i.e. the various spectral features that make a protein's spectrum unique and distinguishable over other protein spectra, can be applied at various degrees of stringency. In other words, if a researcher desired to know whether a given protein is present in a sample, the researcher can apply stringent criteria, which could effectively require an exact overlap of the sample spectrum with a library spectrum.

VI.B. High Throughput Analysis

The single-pass FTIR-ATR methods disclosed in the present invention facilitate high throughput sample analysis by eliminating cumbersome thin pathlength cells, such as those found in demountable cells. The techniques and procedures disclosed herein permit rapid and uncomplicated sample recovery, as well as ready automation of the sample injection, data acquisition and analysis and sample recovery processes. These aspects of the present invention meet the requirements of applications that would benefit from high-speed, accurate analysis of samples.

The above advantages have immediate application in high throughput analysis systems. As the name implies, a key to an effective high throughput analysis system is the ability to analyze many samples very rapidly. Aspects of effective high throughput systems include fast and easy sample introduction, fast and easy sample removal and accurate, reliable and reproducible data acquisition. A high throughput system can involve an operator who performs analyses using equipment having the characteristics described above. In the most efficient high throughput systems, however, the process is automated and operator interaction occurs only during the initiation of the analytic process and in the evaluation and interpretation of the acquired data. Clearly, this arrangement is desirable for the analysis of large numbers of samples. The apparatus and methods of the present invention facilitate such a system.

A high throughput system employing the apparatus and methods of the present invention can be useful for screening a large number of samples for secondary structure content in protein samples. In this embodiment of the present invention, samples to be screened can be prepared by a researcher using protein isolation and purification techniques reported in the literature of incorporating purification strategies and techniques known to those of skill in the art. See, e.g., *Protein Purification Applications: A Practical Approach*, (1989) (Harris & Angal, eds.) IRL Press; *Protein Purification: Principles, High Resolution Methods, Applications*, (1989) (Janson & Ryden, eds.) VCH Publishers. After one or more sample preparation steps, the hardware of a high-throughput system can be configured for automated operation. Following an operator-initiated startup step, the system can continue to acquire spectra and other data for a plurality of samples unattended.

In an automated system, sample introduction can be achieved by means of a robotic sample introduction system. The sample introduction system can operate in conjunction with a sample cell as disclosed herein. Such a sample cell can be configured to maintain preset thermal conditions, as well as facilitate easy sample injection and recovery. Mixing, agitation or concentration of the sample volume can optionally be included, if such a feature is desired and feasible. In an automated system, following sample injection, a computer running a data acquisition and/or analysis software package, can acquire an IR spectrum of a sample. In accordance with the present invention, the sample is preferably in liquid form, and is preferably disposed in an aqueous solution.

Since the sample is preferably disposed in an aqueous solution, it is also preferable to acquire a background spectrum of the sample's liquid component. Such a background sample can also be acquired using automated equipment either before or after samples are analyzed. A spectrum of a sample can be acquired and is preferably stored digitally on a computer or workstation, and more preferably the computer or workstation is controlling or integrated into the sample acquisition process. This data acquisition process can be automated and controlled by computer software. Similarly, the sample removal process can be automated. Samples can be removed and saved for subsequent experiments. The automation of the spectrum acquisition process can permit a plurality of samples to be analyzed automatically and can thus make sample analysis a much more efficient process than it would be, if it were performed manually by a researcher.

An aspect of the present invention that makes it particularly suitable for automation and high throughput analysis, and represents a significant advancement over the present techniques for the IR analysis of samples, is the speed with which a spectrum can be acquired. Multi-pass FTIR-ATR and other IR techniques can require up to 45 minutes for spectrum acquisition, depending on the sample concentration and conditions and instrument configuration. The methods and apparatus of the present invention involve single-pass FTIR-ATR, however, which can reduce data acquisition time to less than 5 minutes. This significant improvement in time greatly enhances the efficiency of data acquisition and consequently an instrument configured as described in the present disclosure can form the centerpiece of a high throughput analysis system. This advance in data acquisition can facilitate the analysis of many more samples than is presently achievable. Such a system can find particular application to projects such as the Human Genome Project, in which a myriad of previously unidentified proteins are being discovered, cloned and characterized every day. The embodiments of the present invention disclosed herein rep- VI.C. Monitoring a Chemical Reaction The apparatus and methods of the present invention can be employed to monitor the progress of a chemical reaction. An embodiment of the present invention can be combined with the automation techniques disclosed herein to facilitate automated monitoring of the progress of a chemical reaction. This ability can find application in a variety of disciplines, including synthetic chemistry, biochemistry and enzymology.

In one embodiment of the present inventive methods and apparatus adapted to monitor a chemical reaction, a reaction vessel, which can be of any size, can be communicatively attached to a sample cell disposed in an FTIR microscope or FTIR bench accessory configured in accordance with the present disclosure. Automated components can be programmed to remove an aliquot from a reaction vessel at given time points on the course of a reaction. The aliquot can be placed in a sample cell and its spectrum acquired. Subsequently, the aliquot can either be returned to the reaction vessel or discarded. Spectra can be analyzed as they are acquired for the appearance or disappearance of spectral features that correspond to an increase in the concentration of the reaction product or, alternatively, a decrease in the concentration of a starting material.

An enzyme-catalyzed reaction can be monitored in a similar fashion. Spectral features attributable to the presence of a substrate can be identified and monitored for a change in intensity; spectral features corresponding to product can be identified and monitored first for appearance and then for a gradual increase or decrease in intensity. The present invention can be of particular use for monitoring enzyme-catalyzed reactions, due to the minimal sample volume necessary to obtain a spectrum. Thus, the present invention facilitates reaction monitoring via analysis of one or more IR spectra acquired over the course of a chemical or enzyme-catalyzed reaction.

VI.D. Characterization of a Protein Sample

The number of proteins being identified and spectroscopically characterized is increasing daily. One benefit of spectroscopically characterizing an identified protein is the attendant ability to identify the protein when it is present in a solution, based on the protein's spectroscopic qualities and features. Spectroscopic identification of a protein can be based on, among other qualities, unique spectroscopic features present in the protein's IR absorption spectrum. The ability to spectroscopically identify a protein can also be facilitated by the characterization of unique structural features of the protein, such as the quantity and quality of the protein's secondary structure. The present invention takes advantage of the ability of spectroscopy in general, and IR spectroscopy in particular, to elucidate the presence of secondary structure that contributes to a protein's IR spectroscopic profile. As noted throughout the present disclosure, regions of the IR spectrum previously inaccessible to researchers are available for the first time and can form the basis for a spectroscopic identification profile.

VI.E. Detection of DNA Binding Interactions

The present invention can also be employed in the detection of DNA-binding interactions of anticancer drugs. The use of arrays of DNA that contain site-specific isotopic labels for use in detection of drug binding permits systematic and cost-effective study of protein and drug interactions with specific DNA sequences. Either drug binding to a specific DNA sequence or drug binding in ternary complexes of proteins such as topoisomerases I can be studied. This application of the present invention, namely the application of an isotope array, can be employed to identify the binding of drugs to DNA in vitro.

VI.E.1. Methodology for the Construction of DNA Arrays

To obtain a locally high concentration of binding sites, a relatively long (200-600 nm) double-stranded DNA molecule comprising repeats of a 10-30 base oligomer can be prepared by hybridization using staggered oligomers. The approximate coverage targeted is preferably $\frac{1}{10}$ of a monolayer. The remainder of the surface is covered with a self-assembled monolayer, preferably comprising C6-hydroxy thiol or C6-carboxy thiol if greater electronic repulsion between DNA and a metal (e.g. gold) surface is required to prevent adsorption of the DNA to the surface. A major thrust of the research is the characterization of surface attached DNA to ensure that a relatively linear DNA is obtained for the binding studies. The procedure for hybridization using staggered oligomers shown in Scheme 7 (see below) provides a route to increasing the effective concentration in the volume of interest while at the same time keeping the amount of sample to a minimum. Surfaces are constructed that have approximately 100 operator sequences per DNA molecule. For a typical operator sequence of 20 bases, this corresponds to construction of DNA molecules of approximately 600 nm in length on the surface. There are two alternative strategies for the construction of surface-attached DNA molecules. First, self-assembly of staggered oligos in solution can be used to create the array. This is illustrated as a three-step hybridization procedure. The choice of a self-complementary sequence is not required for the procedure.

In step 1, the hybridization step, staggered oligomers are hybridized a defined period of time. T4 ligase is added and the hybridization is quenched by adding ethanol to precipitate out DNA. The oligos are then purified to eliminate very short strands using size exclusion chromatography. In step 2, the capping step, long oligomers (greater than 30 repeats or 600 bases) are dissolved in solution. The capping oligomer is then added with an alkane thiol linker and T4 ligase. In step 3, the deprotection by dithiothreitol and surface attachment step, oligomers are placed in a solution containing preferably >90% HS—C6-OH, preferably on a gold substrate and allowed to react for 1-24 hours.

Another strategy, based on synthesis at the surface, can also be employed. Similar to the above-mentioned strategy, the hybridization step and capping step both require addition of T4 ligase in order to fill in the nicks in the DNA. After this is accomplished, the DNA surface will be robust and can be heated to a high temperature as required in the strategy outlined for removal of drugs from the surface once measurements have been made.

A passivating layer of C6 hydroxyl alkane thiol can form a self-assembled monolayer by application to the surface with the deprotected DNA-thiol-linker created in the procedure outlined above. This passivating layer will provide protection against adsorption of the DNA onto the surface, which is preferably a gold surface. The DNA molecules are preferably separated, such that drug molecules and proteins can diffuse to the surface. For example, by spacing the DNA molecules so that they form $\frac{1}{10}$ of a monolayer they will be separated by 40 Å edge-to-edge distance. This space is sufficient for even large proteins to diffuse into the space between the DNA molecules. For analysis of drug molecules alone much higher packing densities are possible.

VI.E.2. Preparation of Patterned Gold Surfaces

Patterned gold surfaces are created by evaporation on a mask. Preferably, the mask has dimensions of 100 µm² gold squares separated by about 1 mm. A mask fashioned of polytetrafluoroethylene (PTFE) is then placed on top of the gold squares. This method of preparing patterned gold surfaces allows the construction of wells for the synthesis or surface attachment strategies. The spacing between wells can be made much smaller for imaging applications. Thus, the spacing between wells can vary and will be dictated, at least in part, by the nature of the application in which the surface is to be applied.

Raman microscopy and infrared microscopy can be used to investigate low density arrays of DNA molecules comprising a given sequence by employing site-specific isotopic labels. Alternatively, high density arrays of double-stranded multiple repeat sequences of a particular DNA operator can serve as the target for drug design efforts. One dimension of the DNA array can comprise a single sequence with a number of site-specific isotopomers and can be used to determine isotopic shifts in spectra. Isotopic labeling of specific $^{13}$C and particularly $^{15}$N positions can be used to determine sites of hydrogen bonding between the drug and DNA. For vibrational spectroscopy it would be desirable to use $^{18}$O labels as well. Both exocyclic amino groups and ring nitrogens are sensitive to the hydrogen bonding environment. N6 amino protons of adenine and N7 of adenine and guanine are affected by hydrogen bonding in the major groove. The N2 amino group of guanine and N3 of both adenine and guanine are affected by the hydrogen bonding in the minor groove. Thus, individual frequency shifts in labeled amino groups that are observed upon drug binding are quantitative indicators of the strength of molecular interaction between the drug and DNA. The effect of hydrogen bonding on ring nitrogens N3 and N7 is complex and has been less studied; however, there a number of ring modes that are affected providing a qualitative indicator of interaction. Comparison of a collection of frequency shifts provides structural and energetic information at the molecular level that permits detection of sequence-specific binding to a known DNA sequence. Thus, in one aspect, the present invention provides a screen that will give structural and thermodynamic information in a single measurement.

VI.E.3. Preparation of Isotope-Labeled DNA Arrays

The creation of isotope-labeled DNA arrays can be achieved by a general strategy for the synthesis or site specifically stable isotope labeled in the constituent nucleobases. A unified synthetic approach is described hereinbelow to incorporate $^{13}$C and $^{15}$N isotopic labels at any position in deoxy-uridine, cytidine, adenosine and guanosine can be synthesized. An advantage of the method described is that a synthetic scheme addresses isotope incorporation into the molecular frame work in all desired combination of atomic positions and isotopes.

VI.E.4. Synthesis of Site-Specifically Labeled Pyrimidines 2' Deoxy-Cytosine and Thymidine A simple approach to chemical synthesis of deoxycytidine is through uridine. Labeled uridine has been synthesized according to Scheme 3 (Lucia Jr. et al., (1995) *Nucl. Acids Res.* 23: 4913-4921) presented below.

Scheme 3

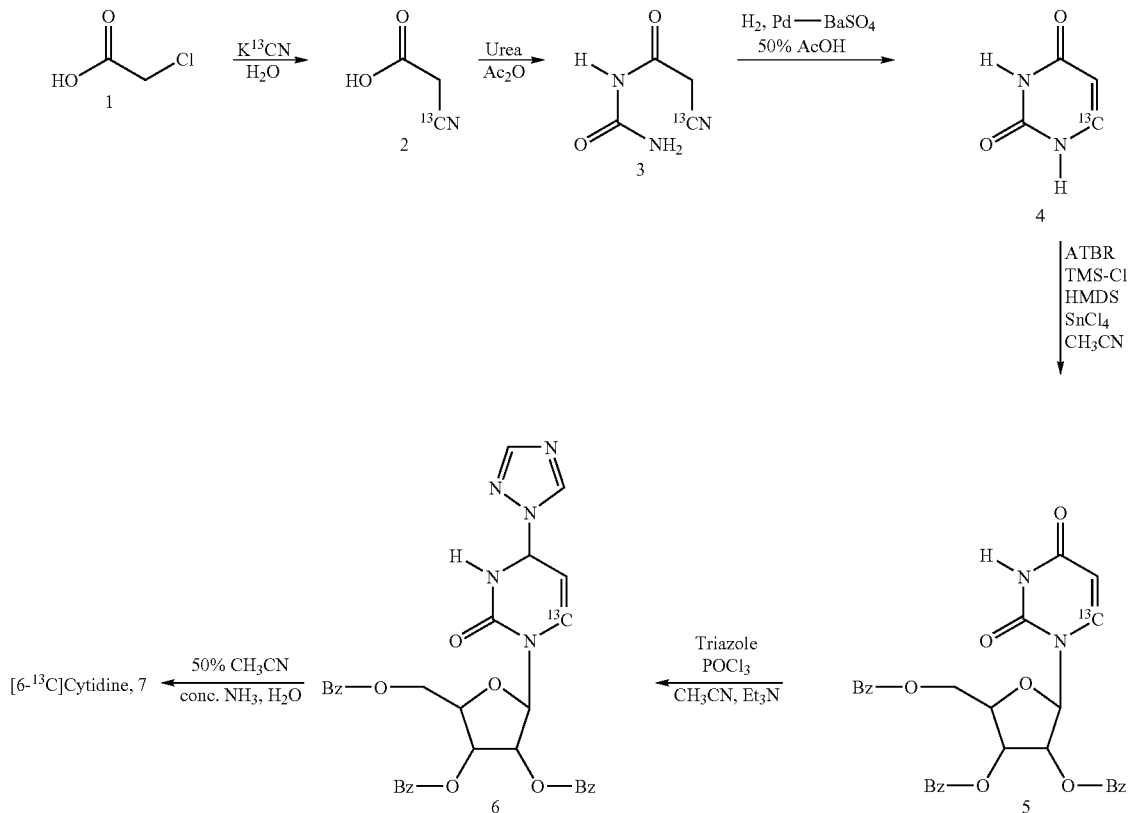

As depicted in Scheme 3, labeled cytidine can be assembled form commercially available labeled reagents through intermediate labeled uridine. This is a simple synthetic path to labeled cytidine.

Scheme 3, however, is not suitable for regiospecific enrichment of N1 and N3 since these are incorporated from the nitrogen atoms of urea. For the regiospecific labeleing of N1 and N3 of uridine, the synthesis of uracil described by Roberts & Larsen (Roberts & Larsen, (1998) *Biochim. Biophys. Acta* 80: 247-254), depicted below as Scheme 4, can be employed.

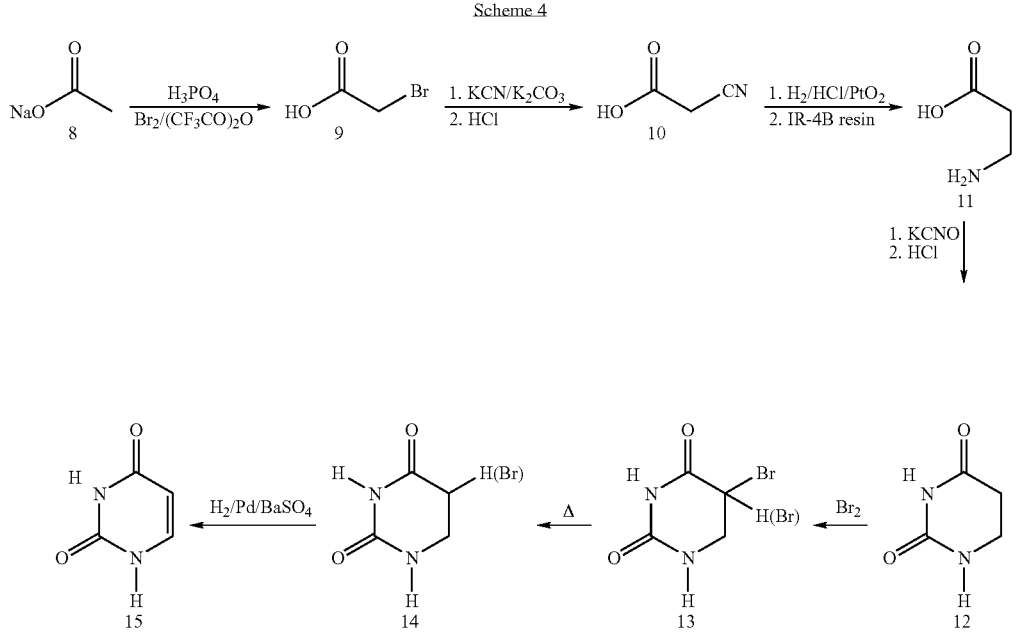

The combination of Scheme 3 and Scheme 4 facilitates site-specific labeling of uridine base moiety in all combinations of $^{13}$C and $^{15}$N. It is noted that the Vorbruggen reaction leading to intermediate 5 in Scheme 3 gives predominantly the desired β-anomer. Any unwanted α-anomer formed is separated at this stage to afford >99% β-cytidine riboside.

A major drawback to the chemical synthesis of 2'-deoxyribonucleosides is that the condensation of the suitably protected 2-deoxyribofuranosyl moiety with nucleobases leads to the formation of anomers. These anomers require very tedious and extensive work for their separation to afford the pure compound. On the other hand, synthesis of the corresponding ribofuranosyl derivatives proceeds very smoothly and gives the β-anomer as almost the exclusive product. For this reason, the synthesis of deoxyribonucleosides by the 2'-deoxygenation of the corresponding ribonucleoside is a preferred approach to the synthesis of deoxyribonucleoside in the context of the present invention. 2'-β-Deoxycytidine can be prepared from the cytidine prepared above by employing methods known in the art. See, Lessor & Leonard, (1981) *J. Org. Chem.* 46: 4300-4301; Robins & Wilson, (1981) *J. Am. Chem. Soc.* 103: 932-933; Robins et al., (1983) *J. Am. Chem. Soc.* 105: 4059-4065; Saito et al., (1986) *J. Am. Chem. Soc.* 108: 3115-3117. The deoxycytidine prepared as outlined above can be made phosphoramidite-ready following known procedures (Bogdan & Chow, (1998) *Tet. Lett.* 39:1897-1900; Scariage et al., (1990) *Nucl. Acids Res.* 18:5433-5441).

Bergstrom et al. have demonstrated high-yield C-5 methylation of protected 5-bromouridine to give thymidine (Ahmadian & Bergstrom, (1998) *Nucleos. Nucleot.* 17: 1183-1190). The 5-bromouridine in this case is readily available in high yields from halogenation of uridine (Asakura & Robins, (1990) *J. Org. Chem.* 55: 4928-4933; Kumar et al., (1994) *Can. J Chem.* 74: 2005-2010). Subsequent deoxygenation and phosphitylation of the thyminidine following protocols known to those of skill in the art provides the phosphoramidite-ready nucleoside for the synthesis of oligomeric DNA.

VI.E.5. Synthesis of Site-Specifically Labeled Purines 2'Deoxy-Adenosine and Guanosine In order to label N1 and N3 positions of adenosine regiospecifically the synthesis developed by Leonard et al. (Barrio et al., (1981) *Proc. Natl. Acad. Sci. U.S.A.* 78: 3986-3988) and adopted by McCloskey et al. (Sethi et al., (1982) *J. Am. Chem. Soc.* 104: 3349-3353) can be employed. This synthesis is depicted below as Scheme 5.

Scheme 5

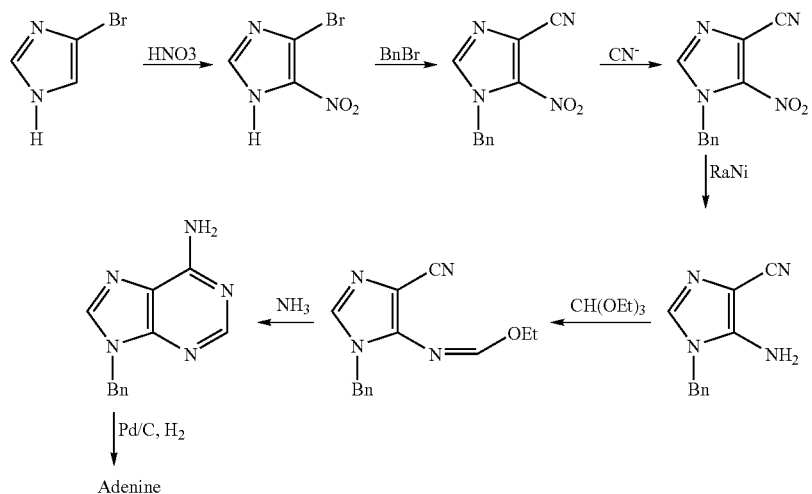

The synthesis shown in Scheme 5 starts with an imidazole ring, onto which a purine ring is built. Although the outlined synthesis allows for regiospecific labeling of N1 and N3 of deoxyadenosine, it is not generally applicable to the synthesis of the deoxyguanosine. Since the labeled deoxyguanosine can be useful in practicing the present invention, a new synthetic route that would permit regioselective N1 and N3 labeling can be employed. A suitable synthetic route is depicted in Scheme 6.

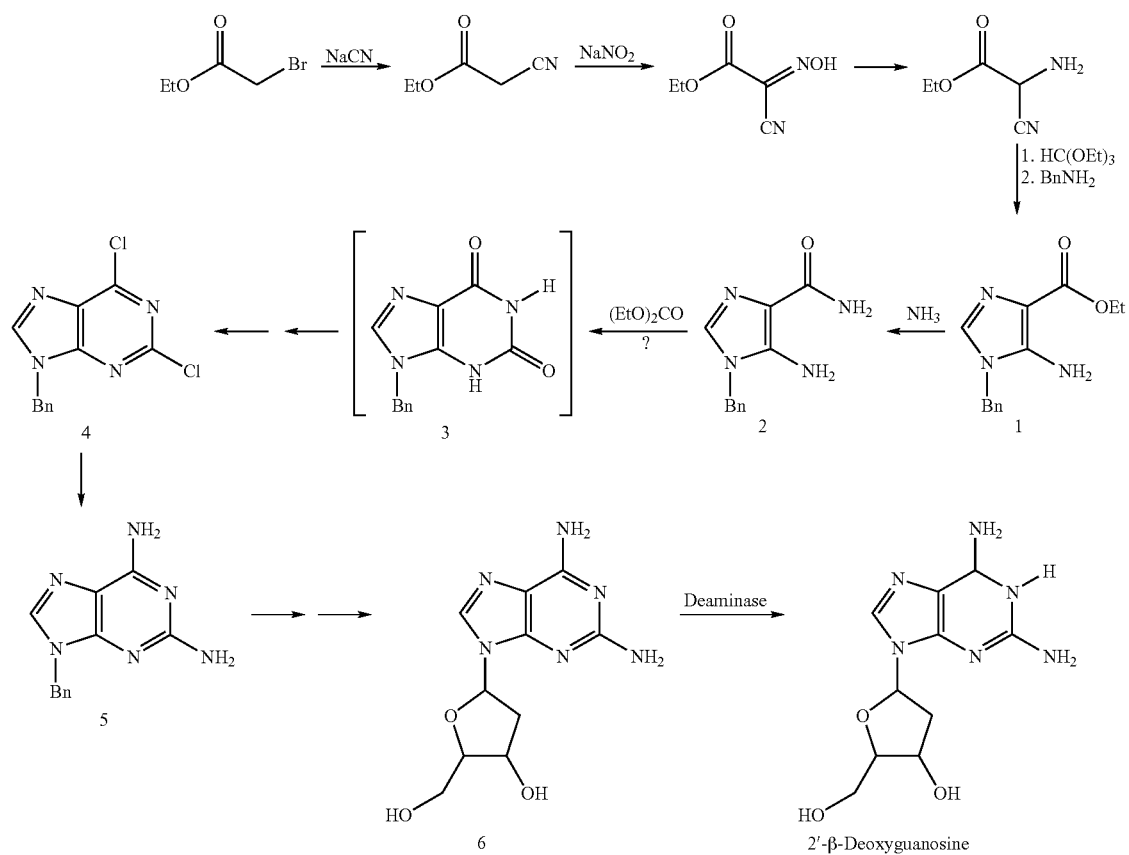

Scheme 6 facilitates the production of site-specific N1 and N3 labeled deoxyguanosine. Shaw et al. (Kadir et al., (1980) *J. Chem. Soc. Perkin Trans.* 1: 2728-2731) have shown that 5-aminoimidazole-4-caboxylate 1 can be prepared as shown. They also prepared intermediate 2 from 1. In Scheme 6 intermediate 2 is reacted with dialky carbonate, which produces intermediate 3. Reaction of intermediate 3 with POCl$_3$ following established protocol affords the dichloropyrimidine 4 from which the diamine 5 is obtained by reaction with aqueous ammonia. Enzymatic ribosylation followed by enzymatic deamination of the diaminodeoxyriboside affords 2'-deoxyguanosine.

VI.E.6. Measurement of Isotope Difference Spectra by Raman and FTIR Spectroscopies Vibrational spectroscopic studies of DNA oligomers, drugs and oligomer-drug complexes can be carried out in buffered solutions by employing the present invention. These are studies in which the FTIR spectrum and Raman spectra of a DNA oligomer and a drug are compared with the spectra of the DNA-drug complex to determine whether there are spectral effects due to the interaction of the drug with DNA. These studies can be conducted with natural abundance DNA and with isotopomers in the exocyclic amino groups of adenine (N6), guanine (N2), and cytidine (N2) and with isotopically labeled purine and pyrimidine rings.

By way of illustrative but non-limiting examples, the spectroscopy of adriamycin is studied using the self-complementary hexamers that have been used for NMR studies (CGTACG, SEQ ID NO: 1) and (CGATCG, SEQ ID NO: 2) (Mazzini et al., (1998) *J. Chem. Soc. Perkin Trans.* 29:1983-1991.). The binding of distamycin is studied using the self-complementary dodecamer (CGCAAATTTGCG, (SEQ ID NO: 3) (Colson et al., (1996) *Biophys. Chem.* 58: 125-140). Topotecan is studied for several different octamers including GGTGCACC. (SEQ ID NO: 4) given its propensity to bind to bind to T (Yao et al., (1998) *Cancer Res.* 58: 3782-2786). Triple helix formation can also be studied as a model of antisense DNA binding.

VI.E.7. Determination of Signal Size Relative to Solution Measurements

There is at least one difference between the repeat sequence oligomers disclosed herein and other surface detection strategies, namely the following. In low salt buffered solutions the DNA will be B-form (C2'-endo conformation of the ribose sugar) and will tend to form a linear strand that rises more or less vertically from the surface. Phased A-tracts or other particular sequences could introduce some bending. A goal of surface attachment strategy is to place DNA molecules sufficiently close to one another that steric repulsion will contribute to their linearity. Since the dimensions of the DNA are of the order 200-600 nm (in the range of the wavelengths of ultraviolet and visible light), the properties of a surface of the present invention are quite different from those of self-assembled monolayers that have been studied extensively. Due in part to the long range order in the substrate-DNA assembly the selection rules for absorption (infra-red) or scattering (visible, Raman) must take into account this orientation. Both the length of DNA strands and the order near the surface present significant advantages for spectroscopic detection.

The Fresnel equations provide surface selection rules (Lorraine & Corson, (1962) *Electromagnetic Fields and Waves*, Freeman, San Francisco). For light polarized parallel to the surface (i.e. s-polarized light) the electric field at the surface will be zero for a conductive surface and there is no absorbance of molecules at the dielectric interface whose transition moments are parallel to the plane of the surface. This selection rule has driven the development of grazing angle techniques for the detection of self-assembled monolayers on gold surfaces. Grazing angle techniques, such as those of the present invention, use p-polarized light that has a component of the electric field perpendicular to the surface. This light can be absorbed because the electric field is not cancelled at the surface for interactions of the perpendicular component with a transition moment normal to the surface. For these and other reasons, a monomer of DNA at the surface gives a very small Raman signal. However, the cancellation of electric fields occurs only at the dielectric interface and, in fact, at distances comparable to the ¼ wavelength of light, the electric field is twice as large as the incident field. For infrared absorption experiments, this results in twice as much change in intensity due to absorption as intuition suggests for an absorption experiment in reflection mode. Since the Raman scattering cross section depends on the fourth power of the frequency this implies an enhancement of a factor $2^4$ or 16 for DNA molecules oriented so that their transition moments are parallel to the surface.

The orientation of surface attached DNA provides enhancement of spectroscopic signals. For DNA perpendicular to the surface, the transition moment of the π-π* transitions of the DNA bases and the in-plane infrared active modes are both be parallel to the surface. This implies that the transition moment responsible for both the resonance Raman effect and infrared absorption will have the same orientation as the radiation field. This is advantageous since instead of measuring the absorption or Raman scattering of an orientation-averaged sample, the present invention facilitates the measurement of a uniaxially oriented sample. The probability for absorption decreases as $\cos^2\theta$, where $\theta$ is the angle between the radiation and the transition moment. For unpolarized infrared light impinging on the surface this results in a factor of three enhancement in the signal for both the incident and reflected electric fields or a factor 9 overall. For the Raman experiment this orientation effect provides a substantial enhancement of $3^4$ or 81 for reflection geometry.

VI.E.8. Estimate of Non-resonant Raman Scattering Signal

Based on the value of 4 nm$^2$ for the surface area of the base of a cylinder that represents B-DNA, the number of DNA molecules in the 1 micron spot size of a typical Raman microscope is approximately 20,000 molecules in the beam. If a repeat sequence with 100 repeat units is created then there are approximately $2\times10^6$ binding sites in the probe volume. For typical non-resonant Raman scattering cross sections of $10^{-30}$ cm$^2$/stearadian and laser powers of 10 mW in focused on this area, corresponding to an intensity of $10^6$ W/cm$^2$, signal count rates of approximately 10 counts per second. This calculation is done for HeNe laser excitation at 632.9 nm where the photon energy is calculated by employing the relationship E=hc/λ, giving a value of $3\times10^{-19}$ J. When the effect of reflection and orientation discussed above in included, the signal size is larger by a factor of 1296. This order of magnitude estimate shows that Raman spectroscopy is feasible. When the techniques of the present invention are employed, the scattering can be measurable in acquisition times of less than ten minutes.

VI.E.9. Estimate of the Fourier-Transform Infrared Signal

The spot size in an FTIR microscope is approximately 30 microns corresponding to a cross-sectional area of about $7\times10^{-6}$ cm$^2$. It is assumed that a similar spot size will be achieved using the same Cassagranian focusing optics in an external bench accessory. Thus, the volume probed when an FTIR microscope is employed is significantly larger than probed when a Raman microscope is employed. For a 1/10 monolayer DNA there are approximately $2 \times 10^7$ molecules in the beam and, when there are 100 repeat units, there are $2 \times 10^9$ identical binding sites in the cross sectional area of the beam. When the infrared absorption cross section is $3 \times 10^{-18}$ cm$^2$/molecule (i.e. 2000 M$^{-1}$cm$^{-1}$), the absorbance of individual groups (amino, carbonyl etc.) are on the order of 1 milliOD. Since the methods of the present invention are carried out in reflection mode, the actual signal size will be larger by a factor of ~20 due to reflection and orientation effects. This order of magnitude estimate indicates that shifts in their frequency will be detectable by FTIR spectroscopy.

VII. Advantages over Prior Art Methods

There are numerous advantages of the disclosed apparatus and methods for protein conformational analysis. These advantages include minimal sample volume and full sample recovery. The single-pass FTIR-ATR techniques disclosed herein permit a spectrum to be acquired in minutes, since the tedious process of loading a demountable sample cell is eliminated. In fact, the simplicity of the sample cell geometry of the present invention can be used to automate data collection for libraries of samples. Finally, the ability to observe the entire FTIR spectrum from 50 cm$^{-1}$ to 3700 cm$^{-1}$, including the amide I, amide II, and amide A bands offers an enormous advantage over current techniques in which these bands are masked by solvent signals.

The fundamental innovations are the design of a delivery and capture method for studying proteins in the FTIR-ATR geometry. While a few studies of proteins and their secondary structure are known by multi-pass FTIR-ATR, the single pass method itself for this application has not been reported to date. The use of single pass FTIR-ATR provides a new approach to consider the capture of proteins using electrostatic properties of a modified chemical surface on the IRE or a pendant monomer or polymeric binding site that captures proteins in solution and effectively concentrates them for viewing by FTIR-ATR spectroscopy. This can be referred to as "filling the active volume". Since that volume is of the order of 1 picoliter a very small amount of material is required to accomplish the chemical modification and very small amounts of sample can be measured spectroscopically. Microfluidic or even nanofluidic delivery of solutions containing proteins can be investigated. The combination of these techniques with spectroscopy provides an aspect of the methods of the present invention. In the following, specific advantages of the method are outlined that are present even without the developments of "filling the active volume" or nanofluidic delivery. These advantages demonstrate the applications provided in accordance with the novel method and apparatus of the present invention.

VII.A. New Spectral Features are Accessible

A library of IR spectra can be generated as described herein and can be centered on the amide I, amide II and amide A bands, which are indicative of various forms of secondary structure as well as the amide III band and the OH stretching region. Protein and other samples can be analyzed by Fourier self-deconvolution, second derivative spectroscopy, and Gaussian band fitting techniques to determine the various individual frequency components present. In addition to these standard techniques, the highly reproducible data obtained by the present invention can be analyzed by employing PCR and PLS methods.

Unlike previous studies, which have been limited to the amide I' band (i.e. the carbonyl stretching band in D$_2$O solution), the present invention facilitates the study of an amide I band, an amide II band, an amide III band, an amide A band, an OH stretching region and other smaller bands in the region from 50 cm$^{-1}$ to 350 cm$^{-1}$. The present invention can be employed to generate additional data from a wider spectral range than previous studies have observed, due to the ability of the present invention to minimize the contribution of water to a sample's IR spectrum.

Construction of prediction vectors (i.e. predictive mathematical algorithms) for α-helical, β-sheets, and random coils can be developed for the amide A region, in addition to amide I and II and other lower frequency modes. The information content of spectra obtained over this spectral range is more complete than that obtained from any previous study because, in part, the contribution of water to the spectrum is minimized and underlying signals are more accessible. A spectral library generated per the present disclosure will preferably comprise the spectra of proteins having secondary structure; these library spectra can be used to determine the correlation between the composition of the FTIR spectra in their entirety and the secondary structure. Stated another way, a spectral library generated using the methods of the present invention can key on the amide I, amide II and amide A bands, but these spectra can be further analyzed to account for other regions of a spectrum, in addition to the amide I, amide II and amide A bands.

The correlation of observed spectral features with known spectral features facilitates an assessment of the relative amounts of α-helix, β-sheet, turn, and random coil regions of proteins of unknown structure. Comparing an acquired spectrum with a library of spectra can form an element of such a correlation. A comparison of secondary structure homology between proteins can be combined with information on the sequence homology to determine, for example, whether the protein belongs to a known family and can be structurally modeled using homology modeling methods.

VII.B. Spectra can be Acquired from Small Sample Volumes

Another advantage of the single-pass FTIR-ATR apparatus and methods of the present invention over multi-pass FTIR-ATR and other IR techniques is that data can be acquired from a minimal sample volume and following data acquisition, the sample can be virtually fully recovered. Turning first to the sample volume, the effective sample volume required for single-pass FTIR-ATR is very small. In fact, the focal spot size of the infrared light in a germanium crystal is only about 30 microns in diameter and thus the probed region is approximated by a cylinder of volume $\pi(30 \times 10^{-6} \text{ m})^2 (600 \times 10^{-9} \text{ m})$, which gives a sample volume $1.7 \times 10^{-15}$ m$^3$=1.7 picoliters. In practice, much larger sample volumes (on the order of 10 to 20 microliters) can be used. In a preferred sample cell embodiment shown in FIG. 1, the sample is fully recoverable, because the sample need not be placed between windows but can instead be injected into a small cup placed directly beneath an IRE, such as a germanium or zinc selenide crystal. This configuration stands in contrast to solution cells where vacuum grease or other adhesive material is often placed on the spacer, rendering sample recovery difficult and greatly enhancing the danger of sample contamination.

VII.C. Instruments can be Automated

Yet another advantage of the present invention is that existent FTIR microscopes, bench accessories, and other equipment can be easily automated to permit them to acquire and analyze spectra in accordance with the methods described in the present disclosure. Specifically, mathematical and statistical operations helpful in analyzing a sample for a quantity and/or quality of secondary structure in accordance with the present invention can be embodied in a software program. The software program can then be installed on a computer or controller that interfaces with an FTIR microscope or other instrument. In one embodiment, software is disposed on a computer that controls the data (i.e. IR spectrum) acquisition process. Such a computer can also be useful for analyzing data and performing data analysis, such as correlating spectral features with a type of secondary structure or subtracting background water signals.

In another embodiment, the software can be disposed on a computer that is integrated into the hardware of the instrument (i.e. an FTIR spectrometer) itself. In other words, the software can reside on the instrument itself. In this embodiment, the software can facilitate data acquisition and optionally data processing, although such processing can also be performed on a separate workstation.

Appropriate software can be installed on an instrument or associated workstation by simply installing the appropriate software program on a suitable device. Automation of the present invention, therefore, simply requires loading the appropriate software, which facilitates an interaction between the software and the instrument. No additional hardware is needed beyond that required for data acquisition. Other hardware can, however, be employed that might be useful for generating output. Such hardware can comprise a printer, a plotter or other output device.

Additionally, there are various approaches to automating the individual steps involved in acquiring an IR spectrum, including the step of sample delivery. To automate this aspect of the data acquisition process, an autosampler can be used to deliver samples via syringe to the sample cell, which can be a cup-like device placed underneath an objective comprising a germanium or zinc selenide crystal. Alternatively, a microfluidic flow system can be employed that is capable of delivering extremely small amounts of sample to the objective. In both of these examples, the sample cell is preferably rinsed between sample measurements. Rinsing can be accomplished by placing a solvent blank in the autosampler, or by the use of a solvent reservoir in conjunction with a valve for switching between sample and rinse solutions in a microfluidic application. Hardware useful for practicing these embodiments of the present invention can be purchased commercially, some of which is available preconfigured to interface with existing systems. Thus, preexisting instruments and equipment can be readily automated.

VII.D. High Quality Spectra can be Rapidly Obtained

Transmission FTIR and traditional FTIR-ATR can be time-intensive. For dilute samples, it can take up to 45 minutes or more to obtain a single spectrum of suitable quality. This is due, at least in part, to the time-consuming step of assembling the multi-pass FTIR-ATR cell. Dilute sample concentrations can also contribute to lengthy data acquisition periods.

The single-pass FTIR-ATR methods of the present invention, however, significantly decrease the time required to obtain a high quality IR spectrum of a sample, even if the sample is very dilute. Good quality spectra can typically be acquired in as little as five minutes or less, even for dilute samples and small quantities of sample.

VII.E. Minimization of Solvent Signal

Another advantage of the single-pass FTIR-ATR spectra of the present invention is the minimization of solvent background. This minimization is an inherent property of the single-pass technique, as opposed to the multi-pass technique. The advantage directly flows from the observation that single-pass ATR requires a single "bounce" or reflection of the incident IR light. Therefore, in single-pass ATR, the light only interacts with the solvent one time. In multi-pass ATR, on the other hand, the light is continually reflected down the length of the IRE (typically 10 or more reflections are involved), and thus the interaction of the IR light with the solvent signal is an additive process and leads to buildup of the solvent-attributable features of the IR spectrum. The single-pass FTIR-ATR techniques of the present invention avoids this problem by limiting solvent interaction to one reflection.

VII.F. Samples can be Recovered

A further advantage of the sample geometry of the single-pass FTIR-ATR configuration of the present invention (an embodiment of which is shown in FIG. 1) is the ease with which a sample can be recovered. In conventional FTIR experiments wherein the sample cell comprises $CaF_2$ windows, the thin path length and the nature of the materials makes it difficult to recover a sample. There are no such constraints on the sample geometry shown in FIG. 1.

In the embodiment shown in FIG. 1, a liquid sample can be placed on a block comprising PTFE or other material that has been milled to fit against a germanium crystal IRE. Following the acquisition of a spectrum, the IRE can be raised (or the sample stage lowered) and the sample can be easily removed by means of an automatic pipetter, syringe or other apparatus useful for transferring a liquid sample. An important aspect of this configuration is the ease with which a liquid sample can be removed from the sample cell. This offers an advantage over the demountable sample cells commonly employed in IR and FTIR spectrum acquisition.

VII.G. Sample Integrity can be Maintained

It is known that the infrared absorption spectrum of a protein sample disposed in $H_2O$ and a spectrum disposed in $D_2O$ are highly temperature dependent. Therefore, comparisons between spectra of a protein sample in aqueous solvent will be flawed if the spectra are acquired at different temperatures. Consequently, a comparison of two or more spectra is preferably made after accounting for temperature differences.

Of equal importance is the desire to maintain sample integrity, which can also be a function of temperature. For example, protein samples can denature and unfold at higher temperatures. Some organic samples can volatize at very low temperatures. It is, therefore, important to offer a mechanism for stabilizing the temperatures to which a sample is exposed at optimal levels.

Temperature effects can have an impact on the quality of IR spectra. When acquiring transmission FTIR measurements of protein amide I bands, the temperature dependence is preferably maintained via a temperature cell that, in a preferred embodiment, comprises a copper sample cell in thermal contact with a thermal reservoir. In order to obtain reliable results that can facilitate quantitative comparisons of secondary structure for FTIR bands, including the amide I band, it is preferable to control the temperatures to which the sample is exposed.

The present invention offers the advantage that by virtue of the small sample volume required, coupled with the absence of windows in the sample cell, the present invention facilitates a much more rapid and effective control over temperature than is possible in a conventional sample cell. Sample volumes can be about 50 picoliters, therefore the term "small sample volumes" contemplates sample volumes of about 50 picoliters. Sample temperature can be controlled, for example, by placing a Peltier chip in thermal contact with an IRE. In this embodiment, the portion of the sample that is interrogated by the evanescent wave is in intimate contact with a germanium crystal and the sample volume is very small, thereby permitting accurate temperature control. Germanium and zinc selenide, preferred IRE materials, do not suffer any significant adverse effects for operating temperatures between 0° and 90° C. The design benefits from a thermally insulated mount for an IRE that permits the temperature of the crystal and protein solution to be modulated, without resulting in heating the mount. There is no need to modify the sample cell if it comprises PTFE or other thermally insulating material. A sample cell can be further modified for temperatures above ambient so as to inhibit the evaporation of a solvent.

Temperature control can be used to maintain the sample temperature near ambient temperature (i.e. for the maintenance of a stable temperature), for the determination of temperature dependent phenomena such as ligand binding, protein folding, and other phenomena. The fact that small sample volumes can be employed permits the temperature cell to be employed for thermodynamic studies of proteins and other samples that are difficult to isolate in large quantities. The small volume of the sample, coupled with the low thermal mass of preferred IRE materials, are advantages for rapid heating and cooling.

VII.H. Reproducibility

Transmission FTIR spectra of proteins can suffer from the appearance of H—O-D bands due to incomplete $D_2O$ exchange. Depending upon the extent of $H_2O/D_2O$ exchange, the presence of varying amounts of $H_2O$, $D_2O$, and H—O-D can cause spectral shifts of the amide I' band from sample-to-sample. Thus, the analysis of proteins in a pure $H_2O$ solution is more reproducible than an analysis performed in an incompletely exchanged $D_2O$ solution.

The use of single-pass FTIR-ATR employing the sample geometry shown in FIG. 1, rather than the demountable sample cell typically employed in transmission FTIR, contributes to a higher degree of reproducibility. A demountable cell has the drawback that the pathlength can change from sample-to-sample. Oberg & Fink, (1998) *Anal. Biochem.* 256: 92-106. This disadvantage is also present in multi-pass FTIR-ATR configurations that use a sample cell to reduce the $H_2O$ pathlength. As shown by the data presented in Table 1, however, the sample-to-sample variability obtained by the single-pass FTIR-ATR methods and apparatus of the present invention is very low. Table 1 indicates that single-pass FTIR-ATR is a highly reproducible technique, and is more reproducible than multi-pass FTIR-ATR techniques.

A complete description of a sample's IR spectrum reproducibility preferably entails calculations of sample-to-sample variance. For example, three trials of ten replicates can be acquired for each protein. A large number of replicates provides sufficient data for a complete chemometric analysis and, by performing the experiment in triplicate, a thorough sample-to-sample reproducibility study is achievable. Studies can be performed to ensure reproducibility from day to day and analyst to analyst.

The accuracy and repeatability of the single-pass FTIR-ATR spectroscopy techniques of the present invention can also be demonstrated by analyzing a plurality of samples at varying concentrations. The acquired data can then be compared to existing FTIR data. In another aspect of the present invention, FTIR spectra of a sample exchanged with $D_2O$ can be acquired and used as a basis for comparison in a validation regimen.

Statistical analysis can be performed to demonstrate the accuracy and reproducibility of the single-pass FTIR-ATR techniques disclosed herein. One measure of the reproducibility of spectral data is based on calculations of variance of fits of the line shape to Gaussian or Lorentzian models. Preliminary studies of sample-to-sample variability along these lines have been performed on six different samples of immunoglobulins (IgG).

A Gaussian fit of these six samples in varying concentrations acquired with the single-pass ATR technique. The Gaussian fitting function used is:

$$L_j(\omega) = \left(\frac{A_j}{\sqrt{2\pi\sigma_j}}\right) \exp\left\{-\frac{(\omega - \omega_{0j})^2}{2\sigma_j^2}\right\} \quad \text{(Eqn. 5)}$$

where j represents each spectral component. $A_j$ represents the amplitude, $\omega_{0j}$, the frequency, and $\sigma_j$ the variance of the jth Gaussian. In the fits below, four Gaussians were used to fit the spectral range from 1500 to 1700 $cm^{-1}$ and includes the amide I and amide II bands.

The data acquired from six samples of IgG appear nearly superimposable. The corresponding frequencies of the five Gaussian fits to the six samples are in excellent agreement. The standard deviations of the frequencies $\omega_{0j}$ for the various bands in multi-Gaussian fit of the six samples are compared in Table 1. The first data set in Table 1 was acquired by incubating the IgG protein in an aqueous solution and subsequently applying a single-pass FTIR-ATR technique, as described herein above. The table represents a fit of the data depicted in FIGS. 2A and 2B.

The second data set in Table 1 was generated by exchanging the IgG protein in $D_2O$, followed by data acquisition using a 12.5 micron spacer in $CaF_2$ windows (a demountable cell) in a transmission FTIR experiment. The data corresponding to the amide II band were not fit for the $D_2O$ sample because of interference from solvent bands and is why differing numbers of Gaussians are presented in the two fits. Summarily, Table 1 demonstrates that the single-pass ATR technique yields more reproducible measurements, as evidenced by the associated fits of the data.

VII.I. Samples can be Concentrated In Situ

Another advantage of the present invention is that the geometry of the systems and methods of the present invention facilitate samples to be concentrated in situ. Samples disposed in a solvent can be concentrated by blowing off solvent from a sample disposed in a sample cell. For example, a steady stream of nitrogen or oxygen gas can be passed over the surface of the sample in order to remove solvent and thus concentrate the sample. Thus, the techniques for concentration of a sample in situ disclosed in the present invention eliminate the need for filter membranes and multiple transfers of the sample, both of which can be sources of lost sample.

VII.J. Solvent Exchange can be Performed In Situ

The present invention facilitates in situ solvent exchange. That is, the present invention facilitates the exchange of a first solvent, water for example, for a second solvent, heavy water for example. This exchange can be effected in situ and can thus greatly reduce the loss of sample in the exchange process.

VII.K. Advantages of Employing Surface-attached DNA for Spectroscopic Applications There are a variety of advantages when surface-attached DNA is employed in spectroscopic applications. For example, measurements with adequate signal-to-noise ratio can be made on very small amount of sample, including levels of only about 3×10⁻¹⁷ moles per square micron of DNA-covered surface. This is approximately 10⁹ times less DNA than would normally be used for a Raman experiment and is 10¹¹ times less DNA than required for a NMR experiment.

Additionally, the orientation effects can be used to determine the mode of binding of a drug using linear dichroism and polarization effects in infrared and Raman spectra. The orientation of the DNA with its helical axis roughly perpendicular to the surface is also advantageous for maximizing signals.

Due to the observation that the surface composition does not significantly change, the methods of the present invention provide a desirable surface for difference spectroscopy. The spectrum of an unbound ligand is preferably acquired independently, however, this can be achieved by employing methods known to those of skill in the art.

Moreover, the specific vibrational information obtained in these experiments can be employed to provide information on ligand binding. This information can subsequently be used to design or modify a ligand (i.e. a DNA-binding agent) and to increase its binding specificity.

Furthermore, the speed of measurement enables the methods of the present invention to be incorporated into high throughput screening applications. Thus, the methods of the present invention circumvent one of the most significant obstacles to high throughput screening, namely data acquisition times.

VII.L. Advantages of Polymeric or Multiple Binding Site Approaches that Fill the Active Volume The use of repeat sequences of DNA is one specific example of an approach for creating a large number of binding sites in the small volume sample by the electromagnetic radiation in a single-pass FTIR-ATR cell. In addition, polymeric molecules containing protein-binding sites can be used. A specific example of this is a polymer with multiple nickel nitrilotriacetic acid (NiNTA) binding moieties. A NiNTA polymer presents numerous protein binding sites for polyhistidine tagged proteins. These proteins can then serve as targets to test for protein-protein interactions. Since the proteins can be added and washed using a fluidic approach, the method permits screening for a large number of protein-protein interactions including the binding of multiple proteins.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

IR Spectrum Acquisition

Mid-frequency and high-frequency ATR-FTIR spectra of a β-sheet forming protein were acquired as seen in FIGS. 2A and 2B. The spectral region shown includes both amide I with a peak at 1636 cm⁻¹ and amide II with a peak at about 1550 cm⁻¹, but also two other peaks at about 1400 and about 1450 cm⁻¹, respectively. Discrepancies between the high and low concentration experiments are observed at about 1750 cm⁻¹ and in the relative intensity of the amide II band. These could be attributable to the hydration state of the protein. In the high frequency region two germanium peaks appear in the low concentration spectrum (shown in blue) as negative spikes at about 2850 cm⁻¹ and about 2910 cm⁻¹. However, the same bands are clearly present in both low concentration and high concentration spectra. The Ge peaks can be removed by a background subtraction procedure.

Example 2

Acquisition of IR Spectra from a Protein Having β-Sheet Structure

Infrared spectra were acquired for immunoglobulin G, a β-sheet forming protein. Acquired spectra are depicted in FIGS. 3A and 3B. Mid-frequency single-pass ATR-FTIR and high-frequency ATR-FTIR spectra of a β-sheet forming protein are depicted in FIGS. 3A and 3B, respectively. The spectral region shown includes both amide I with a peak at 1636 cm−1 and amide II with a peak at 1550 cm⁻¹, but also two other peaks at 1400 and 1450 cm−1, respectively.

TABLE 1

Comparison of Multi-Gaussian Fits For Six Samples of Immunoglobulin G

| ATR 1 | ATR 2 | ATR 3 | ATR 4 | ATR 5 | ATR 6 | Standard Deviation |
|---|---|---|---|---|---|---|
| 1515.8 | 1515.27 | 1515.66 | 1515.04 | 1516.07 | 1517.39 | 0.78024416 |
| 1547.26 | 1546.87 | 1547.62 | 1546.75 | 1547.45 | 1546.97 | 0.36064757 |
| 1620.2 | 1620.62 | 1619.08 | 1619.71 | 1620.39 | 1618.54 | 0.78107679 |
| 1636.6 | 1636.78 | 1637.15 | 1637.05 | 1636.8 | 1635.91 | 0.40453383 |
| 1667.85 | 1669.09 | 1668.67 | 1668.1 | 1668.18 | 1665.71 | 1.09888472 |

| D₂O 1 | D₂O 2 | D₂O 3 | D₂O 4 | D₂O 5 | D₂O 6 | Standard Deviation |
|---|---|---|---|---|---|---|
| 1634.51 | 1602.33 | 1623.63 | 1622.48 | 1622.92 | 1609.29 | 10.5189509 |
| 1638.23 | 1626.34 | 1637.03 | 1637.73 | 1637.12 | 1639.56 | 4.59205421 |
| 1659.92 | 1670.61 | 1684.5 | 1686.44 | 1685.8 | 1686.76 | 10.6347017 |
| 1663.55 | 1646.43 | 1661.59 | 1663.52 | 1661.5 | 1665.97 | 6.60803263 |

Example 3

Evaluation of Methods

The reproducibility of the present inventive method applied to proteins in H₂O solution was compared to transmission FTIR of proteins in H₂O and D₂O solution. By demonstrating the simultaneous observation of amide I, II, III, A and B bands, the results indicated that protein spectra from the single-pass ATR-FTIR technique yielded more information than protein spectra acquired by other FTIR techniques.

To validate the single-pass ATR-FTIR method, the mid-infrared spectra of a representative set of proteins in D₂O solution were acquired using both a conventional transmission FTIR technique and the single-pass ATR-FTIR technique. Comparisons were made for the following proteins: myoglobin, hemoglobin, cytochrome C, ribonuclease A, lysozyme, chymotrypsin, trypsin, and concanavalin. Since the protein studies were performed in D₂O solution, the position of the amide I′ band was compared.

The amide I' bands from the two different techniques were very similar for all of the proteins listed. There were small differences on the left shoulder of the amide I' band due to a small amount of $H_2O$ present in the samples. The presence of $H_2O$ affected the transmission FTIR spectrum due to the pathlength being 12.5 microns. The amide II' bands differed in this comparison; however, careful consideration is needed when analyzing this band. The exchange of N—H with N-D shifts the position of the amide II' band. Thus, varying levels of deuteration rather than differing secondary structure induced discrepancies in the position of amide II'. The amide I' band is the only reliable band for assigning secondary structure for a protein. Moreover, the presence of $D_2O$ (1200 $cm^{-1}$) masked the amide III' region in the transmission FTIR spectra. By contrast, the amide III' region was visible in the single-pass ATR-FTIR spectra since the $D_2O$ can be successfully subtracted from the protein spectrum. In summary, the single-pass ATR-FTIR technique was found to yield the same amide I peak positions as the traditional transmission FTIR method.

Experimental Methods. The proteins were prepared without further purification to a final concentration of approximately 3 mM in $D_2O$, $H_2O$, and/or buffer. The buffer used for all proteins throughout this Example was a 25 mM sodium phosphate solution at a pH of 7.0 with 100 mM NaCl. In the experimental apparatus, the Ge crystal is at the focus of a Cassagranian objective in a UMA500 microscope (BioRad). The sample was injected onto a cylindrical sample well that was milled in a TEFLON® block. More specifically, 10-20 µL of the sample was injected onto the TEFLON® block using a Wheaton automatic pipette. The protein spectra were recorded at ambient temperature and averaged over 64 scans on a Bio-Rad FTS 6000 FTIR spectrometer equipped with a liquid nitrogen-cooled MCT microscope as the detector in ATR mode and a liquid nitrogen-cooled fast TRS wideband MCT detector in the transmission mode. The sample cell consisted of $CaF_2$ windows separated by a 12.5-micron spacer with a partition to yield a compartment for sample and a compartment for solvent. Approximately 10 µL of both sample and solvent were loaded into the cell.

All protein spectra were recorded with a resolution of 2 $cm^{-1}$ in the range of 0-8000 $cm^{-1}$. Background spectra were obtained subsequently. Blowing a steady stream of $N_2$ gas over the TEFLON® block gently dehydrated the protein samples. Spectra were recorded immediately after the sample was deposited onto the TEFLON® block. Spectra were subsequently acquired until a protein gel had formed onto the Ge crystal. The Ge crystal was rinsed with solvent ($H_2O$, $D_2O$, or buffer) and allowed to dry prior to loading another protein sample. The spectral data was acquired using the software package Win-IR-Pro v2.97 manufactured by Bio-Rad. Data analysis was performed using the software package Igor-Pro v3.1. The spectral range of 600-4200 $cm^{-1}$ was used for protein analysis.

Figure 6:
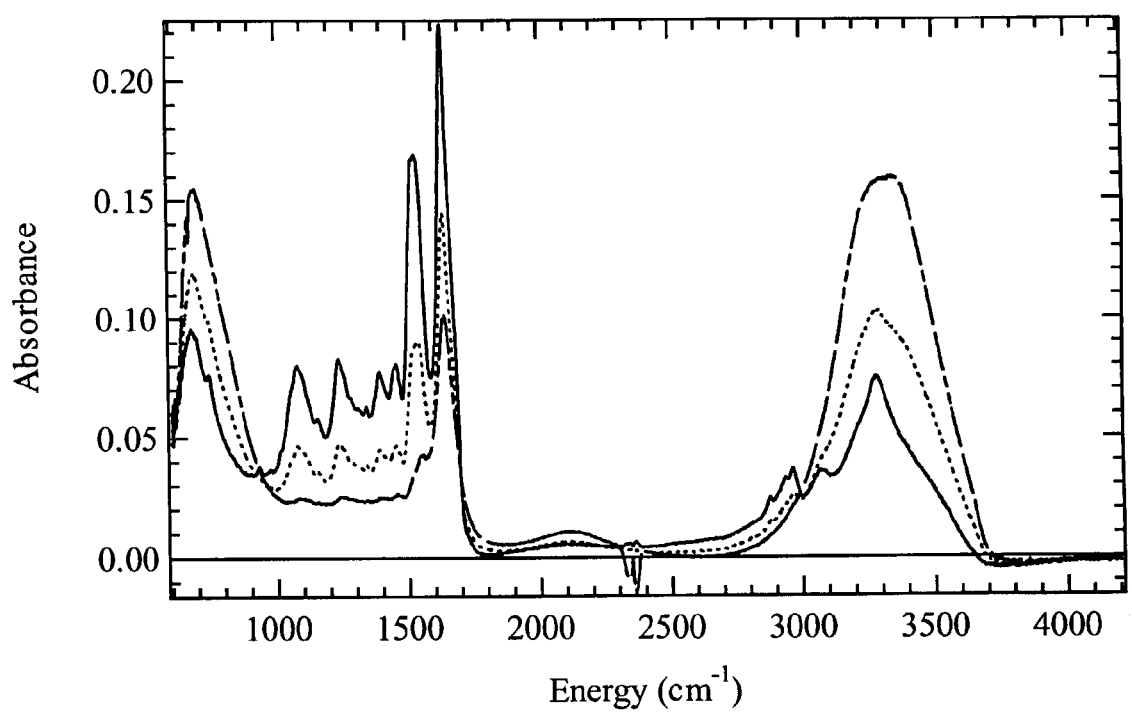
FIG. 6 depicts an example of spectral enhancement upon protein gel formation is displayed. The spectra shown are of the protein chymotrypsin from a liquid sample (dashed), to an intermediate state (dotted), to a gel state (solid).

Gel Sample. FIG. 6 depicts an example of spectral enhancement upon protein gel formation is displayed. The spectra shown are of the protein chymotrypsin from a liquid sample (dashed), to an intermediate state (dotted), to a gel state (solid). Denaturation of a protein due to gel formation or to an interaction with the internal reflection element has been mentioned in the art and is a concern for all ATR-FTIR techniques. In the single-pass ATR method, acquiring protein solution spectra as the protein slowly concentrated onto the Ge crystal enabled any protein denaturation to be observed. Thus, the disadvantage that arose when the sample is concentrated to a gel state was overcome by the fact that protein spectra were observed (albeit with poorer signal-to-noise ratio) at concentrations lower than the gel state. The ability to differentiate those proteins that suffer from denaturation under the conditions of the experiment was demonstrated in this study.

The ideal protein analysis technique would combine the information from a fully hydrated protein sample with that obtained when gentle dehydration was achieved by leaving the sample in a nitrogen environment for a number of minutes. Since the protein sample was exposed in the sample geometry used here, as opposed to being sealed in a sample cell, the protein solution ultimately evaporated and the protein sample formed a gel. Upon formation of the gel state, the spectral features were greatly enhanced as shown in FIG. 6. In addition to the increased information content, it was observed that the signal-to-noise ratio also improved relative to the fully hydrated state.

The ability to observe the transition from a fully hydrated state to a gel state in real time permitted the surveillance of any protein denaturation, thus the crucial distinction between native protein and denatured protein was easily made. For example, no protein denaturation occurred in FIG. 6 since the only spectral change was increased peak intensity for the amide I band. However a frequency shift in this region, evident for several proteins in this study, would have indicated a change in secondary structure. The transition from solvated protein to partially denatured protein was evident for lysozyme, cytochrome C, chymotrypsin, chymotrypsinogen, hemoglobin, myoglobin, papain, pepsin, and trypsin inhibitor. On the other hand, the proteins bovine serum albumin, α-casein, concanavalin, ribonuclease A, trypsin, and trypsinogen did not denature as function of dehydration. For these proteins, there were no shifts in the amide I position. There were spectral changes on the left shoulder of the amide I band but these differences were due to increased protein concentration rather than denaturation.

Thus, protein denaturation did not seem to depend on the type of secondary structure. Rather, protein denaturation was dependent upon the amount of time the protein sample was left in contact with the Ge crystal. There were replicate data sets for all of the proteins in this Example that showed no evidence of denaturation. Denaturation of the protein can thus be controlled, either by not allowing the protein to reach too high a concentration or by controlling the duration of the experiment.

Solution Spectra. Results from the single-pass ATR method made certain that any spectral changes due to protein gel formation were detected. Thus, solution spectra were used for comparison in cases where proteins denatured in the gel state. Protein spectra in both $H_2O$ and phosphate buffer for all of the protein spectra produced in this Example, see e.g. FIG. 10, indicated that water subtraction was not needed since the region from ≈1800-2000 $cm^{-1}$ was relatively flat.

The approach taken in this Example and in accordance with the present invention was holistic in that the spectrum was regarded as that of the protein and associated solvent. For example, the spectrum of hemoglobin in the gel state was compared to a spectrum of hemoglobin in a more hydrated state but with $H_2O$ subtracted from the protein solution spectrum. Both spectra were very similar in the amide I region. The only major difference appeared in amide II, which was more than likely due to a protein/solvent interaction. This finding further validated the idea of a holistic approach that accounts for such interactions, as provided by the present invention.

Figure 10:
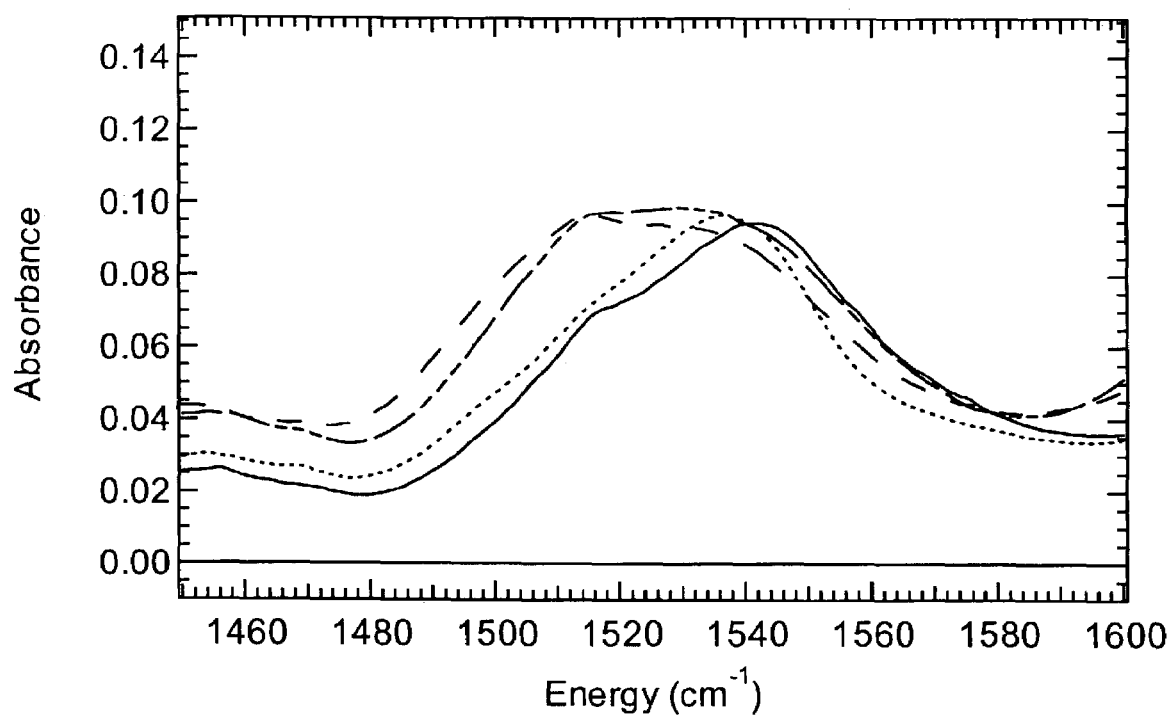
FIG. 10 depicts an enlargement of the amide II region of four protein spectra are shown where myoglobin is represented by the dotted spectrum, cytochrome C is represented by the solid spectrum, ribonuclease A is represented by the dashed spectrum (— —), and chymotrypsin is represented by the second dashed spectrum ( - - - — —).
Figure 11:
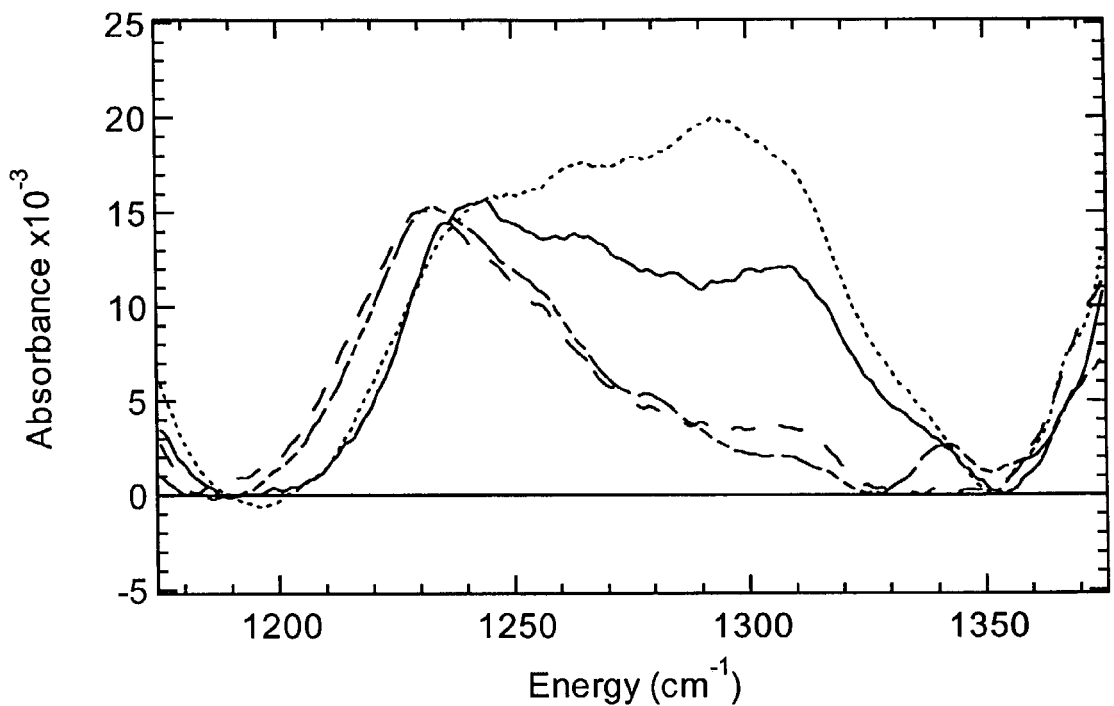
FIG. 11 depicts an enlargement of the amide II region of four protein spectra are shown where myoglobin is represented by the dotted spectrum, cytochrome C is represented by the solid spectrum, ribonuclease A is represented by the dashed spectrum (— —), and chymotrypsin is represented by the second dashed spectrum ( - - - — —).
Figure 12:
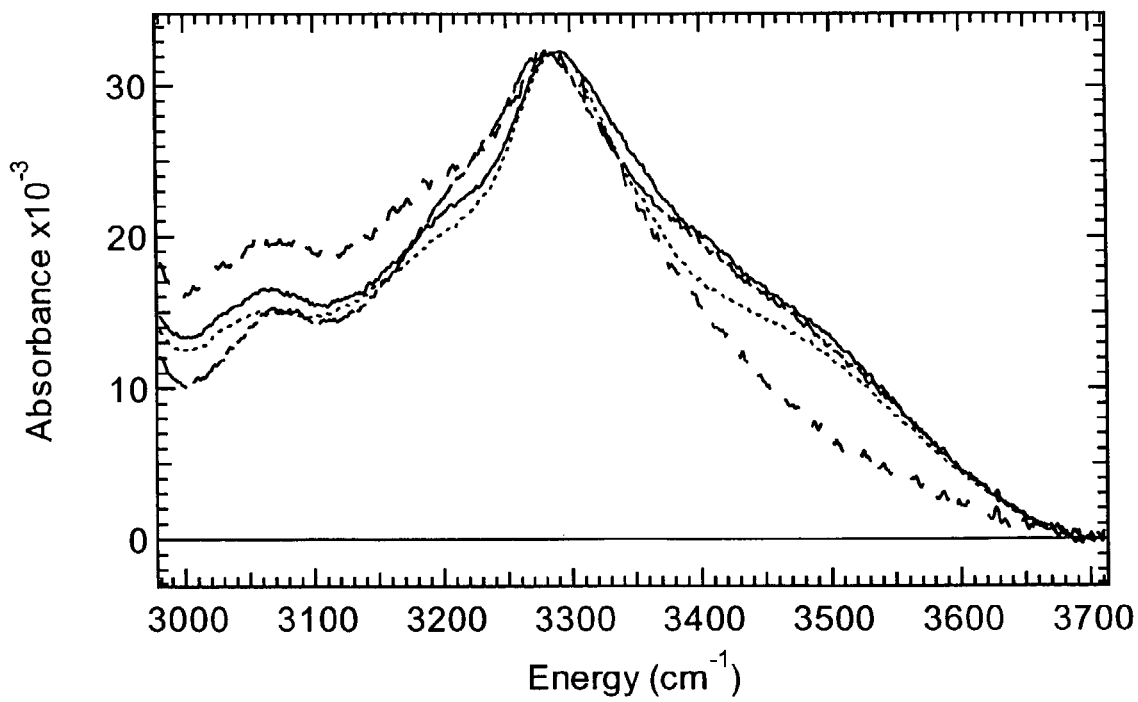
FIG. 12 depicts an enlargement of the amide II region of four protein spectra are shown where myoglobin is represented by the dotted spectrum, cytochrome C is represented by the solid spectrum, ribonuclease A is represented by the dashed spectrum (— —), and chymotrypsin is represented by the second dashed spectrum ( - - - — —).

Representative Spectra. FIGS. 10-12 depict a series of enlargements of the amide II region of four protein spectra, where myoglobin is represented by the dotted spectrum, cytochrome C is represented by the solid spectrum, ribonuclease A is represented by the dashed spectrum (— —), and chymotrypsin is represented by the second dashed spectrum ( - - - — —). FIG. 12 also shows high signal-to-noise ratio amide III bands obtained on the same protein samples shown in FIGS. 10 and 11 for amide I and II, respectively. The increased signal-to-noise ratio achieved by concentrating the protein into a gel state, however, resulted in a stronger amide III band. As with the amide II region, the trend appeared to be that proteins with high β-sheet content yielded strong bands at a lower frequency than proteins with high α-helical content. This is in agreement with the trend that the following secondary structure motifs: turns, β-sheet, α-helix, and random coils, yield bands in respective order in the amide III region.

The enhanced spectral features obtained by single-pass ATR-FTIR allowed for the simultaneous observation of the amide A, B, I, II, and III bands. Trends for each of these bands are reported for four representative proteins. The trend for amide I is that β-sheet structures have a maximum near 1633 cm$^{-1}$ with a shoulder at 1685 cm$^{-1}$ and α-helical structures have a maximum near 1650 cm$^{-1}$. Structures with a mixture of β-sheet and α-helical structure exhibit linear combinations of these two basic spectral forms. Myoglobin and cytochrome C are primarily α-helical in structure and ribonuclease A and chymotrypsin have significant amounts of β-structure.

Surprisingly, from observation of all the amide bands in the ATR-FTIR spectra, the amide II and amide III band shapes showed a significant dependence on secondary structure as well. In the spectra presented in FIGS. 6 and 10-12, enlarged amide II bands for four proteins that have varying secondary structure. The amide II line shape appears to show clear differences between the two primarily α-helical proteins and the primarily β-sheet proteins. In fact the differences observed in the amide II band are as pronounced as those in amide I. The reported trend is that a strong amide II component occurs in the region of 1540-1550 cm$^{-1}$ and a weak component occurs in the region of 1510-1525 cm$^{-1}$. The spectrum for cytochrome C followed this trend and the spectrum of myoglobin was very similar. The strong components for these primarily β-helical proteins were at 1541 cm$^{-1}$ for cytochrome C and at 1536 cm$^{-1}$ for myoglobin. As for the primarily β-sheet proteins, the amide II bands for ribonuclease A and chymotrypsin have a strong component in the region from 1530-1540 cm$^{-1}$. As for the weak component predicted in the region of 1510-1525 cm$^{-1}$, all four amide II bands yielded a component in this region. However for the primarily β-sheet proteins, the component in the region of 1510-1525 cm$^{-1}$ appeared just as strong as the component in the region of 1530 to 1540 cm$^{-1}$.

Amide III bands for the same four proteins unexpectedly exhibited substantial changes in line shape as a function of varying secondary structure as well. The amide III band is usually observed by Raman spectroscopy since the amide III band is so weak in the infrared. However; there are reports of amide III by transmission FTIR including studies of the infrared vibrational circular dichroism (VCD) in thin pathlength cells.

Amide A and B Regions. Single-pass ATR-FTIR is the only IR method that can be used to examine the amide A and B regions. Examination of FIG. 12 revealed trends in the amide A and B bands that correspond to protein secondary structure. The pattern for amide A was similar to that observed in amide I where bands for cytochrome C, myoglobin, ribonuclease A, and chymotrypsin occur in order of decreasing frequencies. The lowest frequency corresponded to the β-sheet structure of chymotrypsin. The intermediate frequency of ribonuclease A reflects a mixed content (21% α-helix, 34.7% β-sheet). Myoglobin, an entirely α-helical protein had a frequency of 3292 cm$^{-1}$. Cytochrome C is also principally α-helical but the amide A band was significantly broader than for myoglobin with nearly the same maximum frequency (3293 cm$^{-1}$). This trend could be due to the fact that there is much greater percentage of turn in the cytochrome C structure than in myoglobin (i.e. the α-helices are shorter in cytochrome c).

Thus, it is clear that the observation of amide A provided information complementary to the amide I band. As for the amide B region, the noticeable trend was that the amide B bands are broader for cytochrome C and myoglobin, the primarily α-helical proteins, than those for ribonuclease A and chymotrypsin, the primarily βsheet proteins. These features, reported here for the first time, demonstrate the utility of the single-pass ATR-FTIR approach, not only for ease of sample preparation, but also for the potential greater spectra range available.

Example 4

Apparatus Configurations

FIG. 13 is a schematic view of a possible bench accessory configuration, which uses the same optical elements as that of the infrared microscope. A removable sample holder with mounted sampling element can be seen. The sampling element is optionally either ZnSe or Ge. An inverted microscope cassegrain objective and objective support base can also been seen, as can infrared beam configuring mirrors and FT-IR bench mounting plate. The path from source to detector is also shown.

Figure 14A:
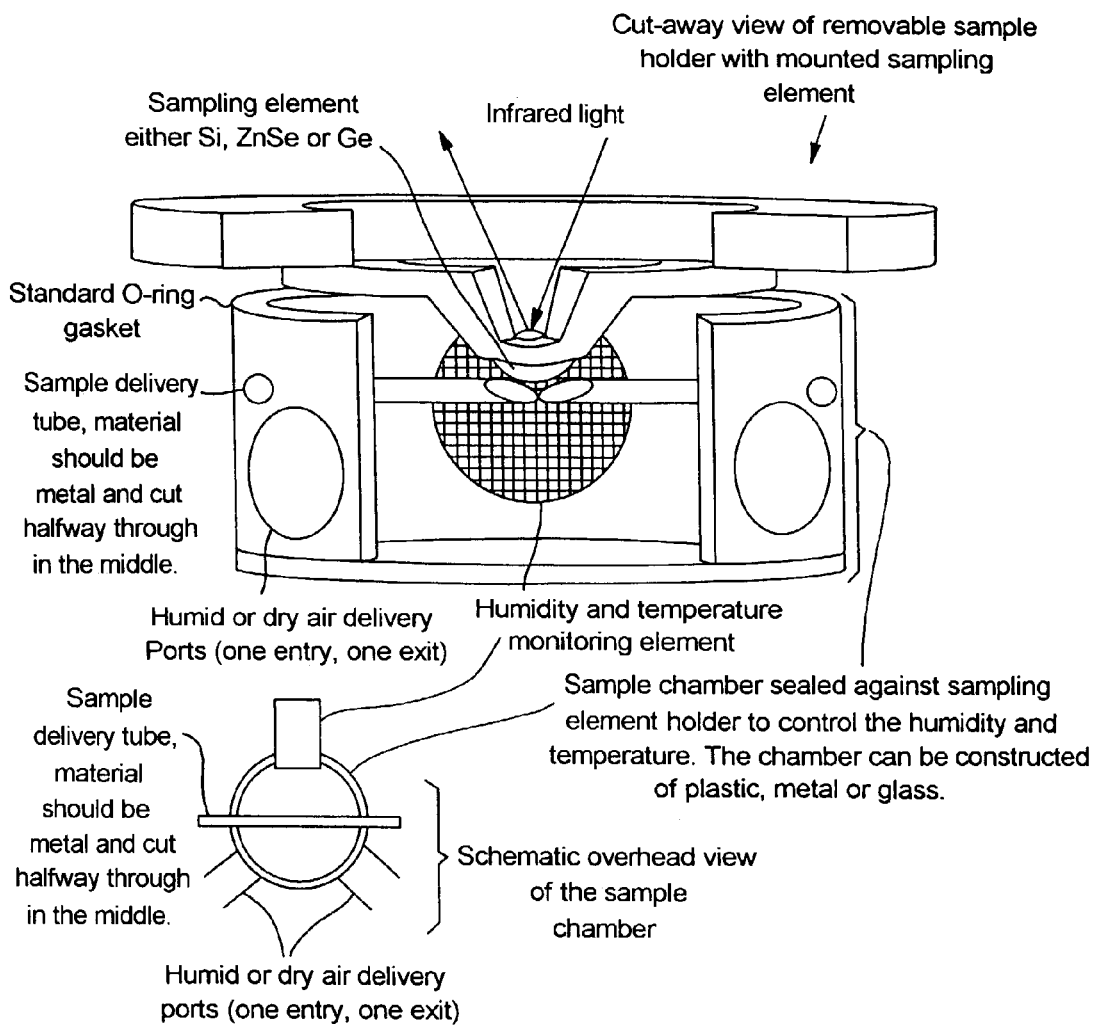
FIGS. 14A and 14B show an ATR-FTIR attachment with humidity control with one option for configuration of a single element humidity and temperature controlled environmental chamber (FIG. 14A) and one option for configuration of humidity and temperature controller (FIG. 14B) for the environmental chamber shown in FIG. 14A. The sample is delivered by a capillary tube to the objective. The droplet that forms is in contact with the objective and can be dried by a stream of nitrogen or re-hydrated by a controlled increase in the ambient humidity inside the chamber. The droplet can be removed by suction and washed away by further application of a washing solution through the capillary tube.
Figure 14B:
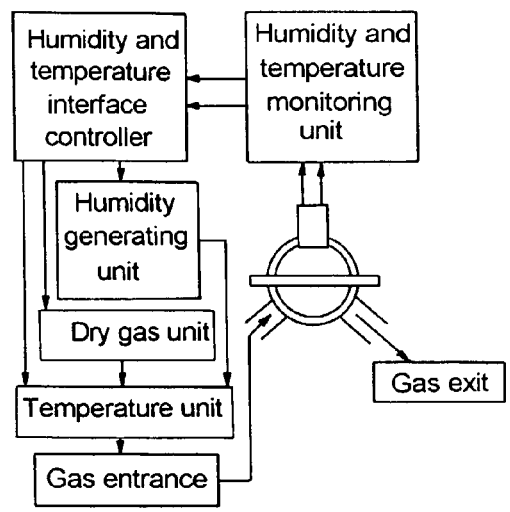

FIGS. 14A and 14B show an ATR-FTIR attachment with humidity control with one option for configuration of a single element humidity and temperature controlled environmental chamber (FIG. 14A) and one option for configuration of humidity and temperature controller (FIG. 14B) for the environmental chamber shown in FIG. 14A. The sample is delivered by a capillary tube to the objective. The droplet that forms is in contact with the objective and can be dried by a stream of nitrogen or re-hydrated by a controlled increase in the ambient humidity inside the chamber. The droplet can be removed by suction and washed away by further application of a washing solution through the capillary tube.

In FIG. 14A, a cut-away view of a removable sample holder with mounted sampling element can be seen, as can a schematic overhead view of the sample chamber. The sampling element can be any of Si, ZnSe or Ge. A humidity and temperature-monitoring element is also shown. The infrared light path is also shown. A standard O-ring gasket is employed, as is a sample delivery tube, wherein the material is optionally metal and optionally cut halfway through in the middle. Humid or dry air delivery ports (one entry, one exit) are also shown. The sample chamber is sealed against sampling element holder to control the humidity and temperature. The chamber can comprise plastic, metal, glass or combinations thereof.

In FIG. 14B, a control scheme for the chamber is depicted, and includes a humidity and temperature interface controller, a humidity and temperature monitoring unit, a humidity generating unit, a dry gas unit, a temperature unit, a gas entrance, and a gas exit.

Figure 15:
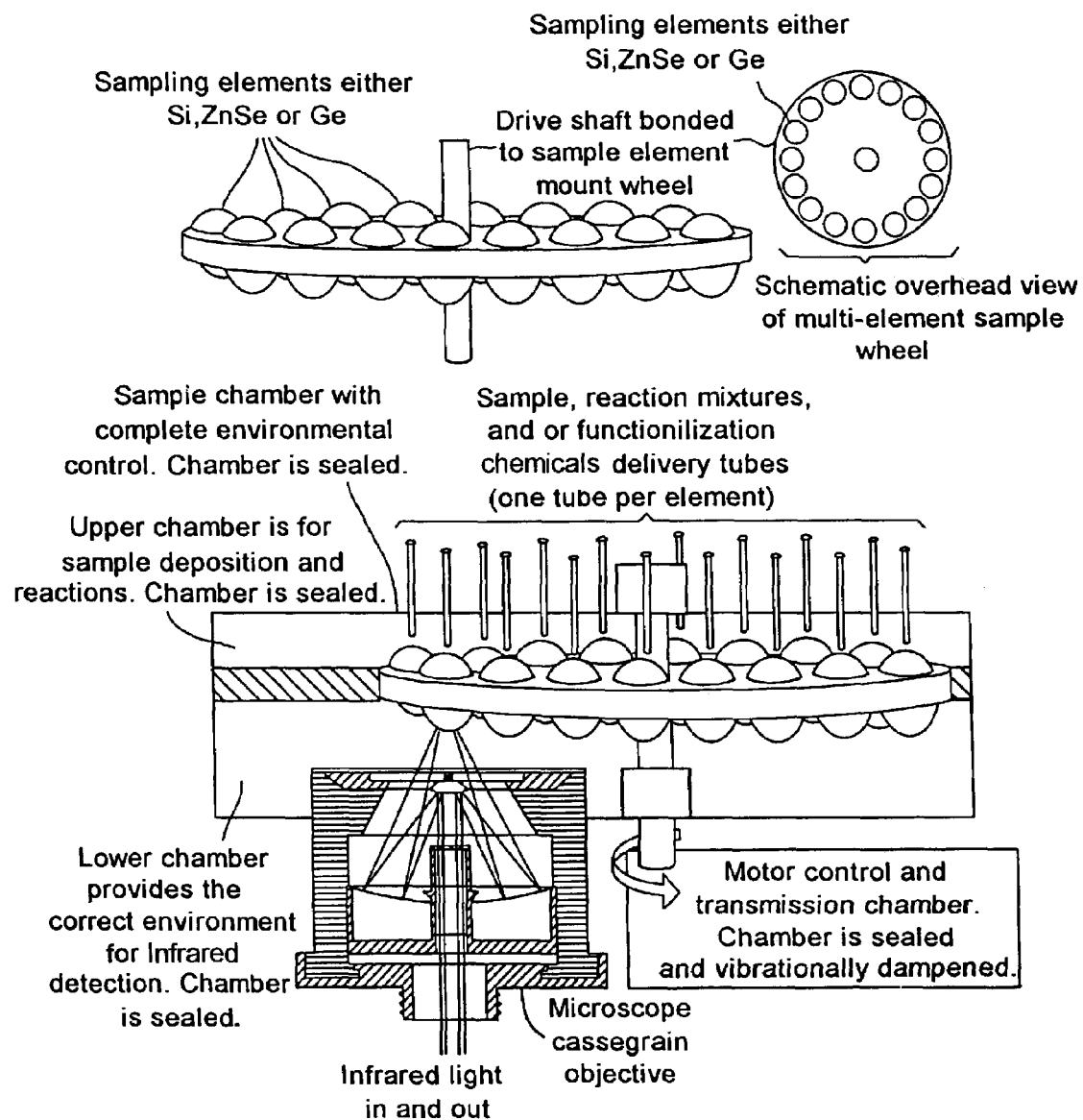
FIG. 15 is a schematic of a method and apparatus for automating ATR-FTIR detection using a wheel that contains multiple ATR objectives that can be placed at the focal plane of an infrared beam in one possible multi-sample element configuration, indicating sample delivery and infrared source arrangement.

FIG. 15 is a schematic of a method and apparatus for automating ATR-FTIR detection using a wheel that contains multiple ATR objectives that can be placed at the focal plane of an infrared beam in one possible multi-sample element configuration, indicating sample delivery and infrared source arrangement.

In FIG. 15, a perspective view, a schematic overhead view, and a schematic cutaway view of multi-element sample wheel and chamber can be seen. A drive shaft is bonded to sample element mount wheel, and the sampling elements can be any of Si, ZnSe or Ge. The lower chamber provides the correct environment for infrared detection and the path of infrared light in and out is shown. The lower chamber is preferably sealed. The upper chamber is for sample deposition and reactions, and is also preferably sealed. The sample chamber with complete environmental control is also shown, and is also preferably is sealed. Sample, reaction mixtures, and or functionlization chemicals delivery tubes (one tube per element) is also shown. A microscope cassegrain objective is also shown, as is a motor control and transmission chamber. The chamber is sealed and vibrationally dampened.

REFERENCES

The references listed below as well as all references cited in the specification are incorporated herein by reference to the extent that they supplement, explain, provide a background for or teach methodology, techniques and/or compositions employed herein.

Byler & Susi (1986) *Biopolymers* 25: 469-87
Chittur, (1998) *Biomaterials* 19: 357-69
Douseeau & Pezolet, (1990) *Biochem.* 29: 8771-79
Dousseau et al., (1989) *Appl. Spectrosc.* 43(3): 538-42
Faber & Kowalski, (1997) *J. Chemometr.* 11:181-238
Gemperline, (1997) *Chemometrics Short Course*, pp. 66-75
Harris & Angal (eds.), (1989) *Protein Purification Applications: A Practical Approach*, IRL Press
Jakobsen et al., (1986) *Biopolymers* 25: 639-54
Janson & Rydéen (eds), (1998) *Protein Purification: Principles, High Resolution Methods, and Applications,* 2nd ed., Wiley-Liss, New York
Jencks, (1986) *Method. Enzymol.* 6 (125): 914-29
Jongh et al., (1996) *Anal. Biochem.* 242: 95-103
Krimm & Abe, (1972) *Proc. Nat. Acad. Sci.* 69 (10): 2788-92
Krimm, (1962) *J. Mol. Biol.* 4: 528-40
Kumosinski & Unruh, (1994) in *ACS Symposium Series 576, Molecular Modeling: From Virtual Tools to Real Problems*, (T. Kumosinski & Liebman, eds.) pp. 71-98
Matsui & Tanaka, (1987) *Appl. Spectrosc.* 41(5): 861-65
Miyazawa (1960) *J. Chem. Phys.* 32(6): 1647-52
Miyazawa et al., (1956) *J. Chem. Phys.* 24(2): 408-18
Nabet & Pezolet, (1997) *Appl. Spectrosc.* 51(4): 466-69
Oberg & Fink, (1998) *Anal. Biochem.* 256: 92-106
Powell et al., (1986) *Appl. Spectrosc.* 40(3): 339-44
Pribic, (1994) *Anal. Biochem.* 223: 26-34
*Protein Purification Applications: A Practical Approach*, (1989) (Harris & Angal, eds.) IRL Press
*Protein Purification: Principles, High Resolution Methods, Applications*, (1989) (Janson & Ryden, eds.) VCH Publishers
Purcell & Susi, (1984) *J. Biochem. Bioph. Meth.* 9: 193-99
Susi, (1972) *Method. Enzymol.* 26 Pt.C: 455-72
Susi & Byler, (1986) *Method. Enzymol.* 130: 290-311
Susi & Byler, (1988) *Appl. Spectrosc.* 42(5): 819-25
Susi et al., (1985) *J. Biochem. Bioph. Meth.* 11: 235-240
Teichmann et al., (2000) *Bioinformatics* 16: 117-24
Wasacz et al., (1987) *Biochem.* 26:1464-70
Yang et al., (1985) *Appl. Spectrosc.* 39(2): 282-87
Zhang & Zhang, (2000) *Biopolymers* 53: 539-49
U.S. Pat. No. 4,602,869
U.S. Pat. No. 3,393,603
U.S. Pat. No. 5,051,551

It will be understood that various details of the invention can be changed without departing from the scope of the invention. Furthermore, the foregoing description is for the purpose of illustration only, and not for the purpose of limitation—the invention being defined by the claims.

---

What is claimed is:

1. A multi-sample infrared (IR) spectrum measuring apparatus for the automated detection of the IR spectra of a plurality of solublized samples, the apparatus comprising:
   (a) an IR radiation source for supplying IR radiation;
   (b) a microscope objective for focusing said IR radiation at a focal plane;
   (c) a sample element mount wheel comprising a plurality of sampling elements, each sample element comprising;
      (i) an internal reflecting element (IRE) comprising a reflection face located on the IRE at a region of intended contact between the IRE and a solubilized sample; wherein when the sample element is placed at the focal plane, the IR radiation is incident on the reflection face, further wherein the IR radiation is reflected from the reflection face once thereby creating an evanescent wave;
      (ii) a sample cell comprising an active sample volume;
      (iii) a functionalized tip comprising a surface-immobilized probe that partially or completely fills the active sample volume exposed to the evanescent wave; and
      (iv) a delivery tube for delivery of one or more of the group consisting of a sample, a reaction mixture, and functionalization chemicals;
   (d) a drive shaft intersecting the sample element mount wheel perpendicularly through the center of the mount wheel and bonded thereto, wherein rotation of the drive shaft around its central axis rotates the sample element mount wheel such that each of the sample elements of the sample element mount wheel can be placed at the focal plane of the IR radiation;
   (e) a motor control and transmission chamber, comprising a motor control element, said motor control element being in contact with the drive shaft and providing rotation to the drive shaft; and
   (f) a detector for detecting the once-reflected IR radiation.

2. The apparatus of claim 1, wherein the IR radiation source is a Fourier transform infrared (FTIR)-based instrument.

3. The apparatus of claim 1, wherein the IRE of each of the plurality of sample elements is an attenuated total reflectance (ATR) objective.

4. The apparatus of claim 1, wherein the IRE of each of the plurality of sample elements comprises a material selected from the group consisting of silicon, zinc selenide, and germanium.

5. The apparatus of claim 1, wherein the IRE of each of the plurality of sample elements is hemispherical.

6. The apparatus of claim 1, wherein the functionalized tip of each of the plurality of sample elements comprises a material selected from the group consisting of a DNA oligomer and repeat sequences thereof, an RNA oligomer and repeat sequences thereof, a protein, a peptide, and a small molecule.

7. The apparatus of claim 6, wherein the material is disposed on a scaffold.

8. The apparatus of claim 7, wherein the material is disposed at a plurality of sites on the scaffold.

9. The apparatus of claim 1, wherein the microscope objective is a cassegrain objective.

10. The apparatus of claim 1, wherein the motor control and transmission chamber is sealed and vibrationally dampened.

11. The apparatus of claim 1, further comprising a sample chamber substantially enclosing the sample element mount wheel, the sample chamber comprising:
   (a) an upper chamber for sample deposition and reactions; and
   (b) a lower chamber for providing an environment for IR detection and into which the IR radiation is directed.

12. The apparatus of claim 11, wherein the lower chamber of the sample chamber is sealed.

13. The apparatus of claim 11, wherein the upper chamber of the sample chamber is sealed.

14. The apparatus of claim 11, wherein the sample chamber can control one or more environmental factor selected from the group consisting of temperature and humidity.

15. The apparatus of claim 1, wherein each of the plurality of solubilized samples has a volume of 50 picoliters or less.

* * * * *